(12) United States Patent
Park

(10) Patent No.: US 11,576,842 B2
(45) Date of Patent: Feb. 14, 2023

(54) PASSAGE DEVICE AND MEDICATION DOSE MANAGEMENT DEVICE

(71) Applicant: COLEDY INC., Seoul (KR)

(72) Inventor: Kyungdo Park, Seoul (KR)

(73) Assignee: COLEDY INC., Seoul (KR)

( * ) Notice: Subject to any disclaimer, the term of this patent is extended or adjusted under 35 U.S.C. 154(b) by 52 days.

(21) Appl. No.: 16/632,336

(22) PCT Filed: Jul. 19, 2018

(86) PCT No.: PCT/KR2018/008170
§ 371 (c)(1),
(2) Date: Jan. 17, 2020

(87) PCT Pub. No.: WO2019/017708
PCT Pub. Date: Jan. 24, 2019

(65) Prior Publication Data
US 2020/0170890 A1    Jun. 4, 2020

(30) Foreign Application Priority Data

Jul. 19, 2017 (KR) .......... 10-2017-0091537
Aug. 17, 2017 (KR) .......... 10-2017-0103918
(Continued)

(51) Int. Cl.
*A61J 7/04* (2006.01)
*A61J 7/00* (2006.01)

(52) U.S. Cl.
CPC .......... *A61J 7/0481* (2013.01); *A61J 7/0076* (2013.01); *A61J 7/0436* (2015.05); *A61J 2200/30* (2013.01); *A61J 2200/70* (2013.01)

(58) Field of Classification Search
CPC ........ A61J 7/0445; A61J 15/001; A61J 1/065; A61J 7/0076; A61J 7/0481; A61J 2200/70;
(Continued)

(56) References Cited

U.S. PATENT DOCUMENTS 3,258,153 A * 6/1966 Morgan .................... G07F 9/02
                                                              221/268
3,369,697 A * 2/1968 Glucksman ........... A61J 7/0472
                                                                221/9
(Continued)

FOREIGN PATENT DOCUMENTS

CN    101257882    9/2008
CN    201352358    11/2009
(Continued)

OTHER PUBLICATIONS

Supplementary European Search Report dated Mar. 5, 2021 for European Patent Application No. 18835656.2.
(Continued)

*Primary Examiner* — Rakesh Kumar
(74) *Attorney, Agent, or Firm* — Ladas & Parry, LLP

(57) ABSTRACT

A contents passing device according to the present invention includes a passing operation part configured to guide movement of contents, a passing movement part rotatably disposed in the passing operation part and configured to move so that the contents are passed, and a sensing part disposed in the passing operation part and configured to sense contents discharged due to free rotation of one end of the passing movement part, wherein the sensing part detects information on the sensed contents.

14 Claims, 47 Drawing Sheets

(30) Foreign Application Priority Data

Oct. 27, 2017 (KR) ........................ 10-2017-0141039
Jan. 15, 2018 (KR) ........................ 10-2018-0005274
Jul. 17, 2018 (KR) ........................ 10-2018-0082941

(58) Field of Classification Search
CPC ............ B65D 80/0409; B65D 83/0445; B65D 83/0454; G07F 17/0092; G07F 11/62; G07F 11/18
USPC ........................................................ 221/12
See application file for complete search history.

(56) References Cited

U.S. PATENT DOCUMENTS

| | | | | |
|---|---|---|---|---|
| 3,677,437 | A * | 7/1972 | Haigler | G06M 7/00 53/500 |
| 4,266,563 | A * | 5/1981 | Fujita | G07D 1/00 453/41 |
| 4,310,103 | A * | 1/1982 | Reilly, Jr. | A61J 7/0481 221/76 |
| 4,573,606 | A * | 3/1986 | Lewis | A61J 7/0481 221/3 |
| 4,872,591 | A * | 10/1989 | Konopka | A61J 7/0481 221/129 |
| 5,148,944 | A * | 9/1992 | Kaufman | G07F 11/10 221/268 |
| 5,197,632 | A * | 3/1993 | Kaufman | A61J 7/04 221/197 |
| 5,329,459 | A * | 7/1994 | Kaufman | A61B 5/4833 221/9 |
| 5,671,262 | A * | 9/1997 | Boyer | G06M 1/101 377/6 |
| 5,752,620 | A * | 5/1998 | Pearson | G07F 17/0092 221/133 |
| 5,755,357 | A * | 5/1998 | Orkin | A61J 7/0084 221/121 |
| 5,768,327 | A * | 6/1998 | Pinto | G06M 1/00 377/7 |
| 6,004,020 | A * | 12/1999 | Bartur | G07F 9/002 700/242 |
| 7,446,302 | B2 * | 11/2008 | Mason | G07F 9/02 250/221 |
| 8,936,175 | B1 * | 1/2015 | Song | A61J 7/0472 221/15 |
| 9,046,403 | B2 * | 6/2015 | Ortenzi | A61J 1/18 |
| 9,113,729 | B2 * | 8/2015 | Righetti | A47F 1/10 |
| 9,682,016 | B1 * | 6/2017 | Balasubramanian | G06M 1/101 |
| 2003/0105554 | A1 * | 6/2003 | Eggenberger | G16H 20/13 700/231 |
| 2005/0113967 | A1 * | 5/2005 | Kim | G07F 11/44 221/6 |
| 2006/0071011 | A1 | 4/2006 | Varvarelis et al. | |
| 2006/0273106 | A1 * | 12/2006 | Kim | B65B 9/02 221/200 |
| 2007/0228065 | A1 * | 10/2007 | Anderson | B65D 83/0409 221/152 |
| 2008/0195247 | A1 * | 8/2008 | Mallett | G07F 11/62 700/231 |
| 2009/0177316 | A1 * | 7/2009 | Schedel | G07F 11/62 700/231 |
| 2010/0138037 | A1 * | 6/2010 | Adelberg | G07F 9/001 700/241 |
| 2011/0060457 | A1 * | 3/2011 | De Vrught | A61J 7/0418 700/231 |
| 2012/0029692 | A1 * | 2/2012 | Owen | G07F 17/0092 356/402 |
| 2013/0116818 | A1 * | 5/2013 | Hamilton | A61J 7/04 221/277 |
| 2013/0200033 | A1 * | 8/2013 | Zonana | A61J 7/0076 215/231 |
| 2013/0304255 | A1 * | 11/2013 | Ratnakar | G07F 17/0092 700/242 |
| 2014/0353327 | A1 | 12/2014 | Bae et al. | |
| 2016/0328535 | A1 * | 11/2016 | Barr | A61J 7/0472 |
| 2017/0095405 | A1 * | 4/2017 | Afsarifard | A61J 7/0472 |
| 2017/0337157 | A1 * | 11/2017 | Rothschild | G16H 20/13 |
| 2017/0363673 | A1 * | 12/2017 | Mukherjee | G06K 19/0717 |
| 2018/0143265 | A1 * | 5/2018 | Nagasaka | G01R 33/34 |
| 2018/0184971 | A1 | 7/2018 | Hong | |
| 2020/0022875 | A1 * | 1/2020 | Park | B65D 83/06 |
| 2020/0170890 | A1 * | 6/2020 | Park | A61J 1/03 |

FOREIGN PATENT DOCUMENTS

| | | | | |
|---|---|---|---|---|
| CN | 102300544 | | 12/2011 | |
| CN | 109843246 | A * | 6/2019 | ............ A61J 1/16 |
| DE | 198 25 298 | | 12/1999 | |
| EP | 2 926 795 | | 10/2015 | |
| EP | 2926795 | A1 * | 10/2015 | ............ A61J 1/03 |
| JP | 3362225 | B2 * | 1/2003 | ............ A61J 7/0084 |
| JP | 2007-319205 | | 12/2007 | |
| JP | 2015-101366 | | 6/2015 | |
| KR | 10-2007-0015244 | | 2/2007 | |
| KR | 10-2010-0055976 | | 5/2010 | |
| KR | 10-2012-0096798 | | 8/2012 | |
| KR | 10-2014-0141277 | | 12/2014 | |
| KR | 10-2015-0005339 | | 1/2015 | |
| KR | 10-2015-0072111 | | 6/2015 | |
| KR | 20160104526 | A * | 9/2015 | |
| KR | 10-2016-0104526 | | 9/2016 | |
| KR | 10-2016-0104557 | | 9/2016 | |
| KR | 10-2016-0126928 | | 11/2016 | |
| KR | 10-2016-0134472 | | 11/2016 | |
| KR | 10-2017-0011039 | | 2/2017 | |
| KR | 102241567 | B1 * | 7/2018 | ............ A61J 1/03 |
| KR | 20200106410 | A * | 4/2019 | ............ A61J 7/04 |
| WO | 2009/080309 | | 7/2009 | |
| WO | WO-2011154018 | A1 * | 12/2011 | ............ A61J 1/03 |
| WO | 2012/002609 | | 1/2012 | |
| WO | 2012/109222 | | 8/2012 | |
| WO | 2015/150240 | | 10/2015 | |
| WO | WO-2015150240 | A1 * | 10/2015 | ............ A61J 1/03 |
| WO | WO-2016059428 | A2 * | 4/2016 | ............ A61B 5/1172 |
| WO | 2016/130815 | | 8/2016 | |
| WO | 2016/137186 | | 9/2016 | |
| WO | 2017/184645 | | 10/2017 | |
| WO | WO-2020021292 | A1 * | 1/2020 | |
| WO | WO-2021020976 | A1 * | 2/2021 | |

OTHER PUBLICATIONS

Office Action dated Apr. 6, 2021 for Japanese Patent Application No. 2020-502575 and its English translation from Global Dossier.
Office Action dated Jun. 21, 2021 for Indian Patent Application No. 202017006973.
International Preliminary Report on Patentability for PCT/KR2018/008170 dated Jan. 21, 2020 and its English translation from WIPO.
Office Action dated Mar. 26, 2020 for Korean Patent Application No. 10-2018-0082941 and its English translation by Google Translate.
International Search Report for PCT/KR2018/008170 dated Nov. 8, 2018 and its English translation from WIPO.
Written Opinion of the International Searching Authroity for PCT/KR2018/008170 dated Nov. 8, 2018 and its English translation from WIPO.
Office Action dated Jun. 29, 2018 for Korean Patent Application No. 10-2017-0091537 and its English translation by Google Translate.
Office Action dated Mar. 6, 2019 for Korean Patent Application No. 10-2017-0091537 and its English translation by Google Translate.
Office Action dated Jul. 19, 2019 for Korean Patent Application No. 10-2017-0091537 and its English translation by Google Translate.
Office Action dated Sep. 2, 2019 for Korean Patent Application No. 10-2017-0091537 and its English translation by Google Translate.
Office Action dated Nov. 21, 2017 for Korean Patent Application No. 10-2017-0141039 and its English translation by Google Translate.
Office Action dated May 14, 2019 for Korean Patent Application No. 10-2018-0082941 and its English translation by Google Translate.

(56) References Cited

OTHER PUBLICATIONS

Office Action dated Jan. 5, 2022 for Chinese Patent Application No. 201880048290.3 and its English translation from Global Dossier.

* cited by examiner

PASSAGE DEVICE AND MEDICATION DOSE MANAGEMENT DEVICE

TECHNICAL FIELD

The present invention relates to a contents passing device, and more particularly, to a passing device and a medication management device capable of sensing discharge of contents discharged from a containing apparatus and allowing a user to take a fixed amount of contents.

BACKGROUND ART

Generally, medicines such as digestive agents, health supplements such as vitamins, and foods such as sweets are produced in the form of solid, powder, or liquid contents, and tools, apparatuses, and the like are manufactured in the form of solid contents (hereinafter referred to as "contents").

Medicine and food contents are taken in a fixed amount or a necessary amount to prevent overuse or addiction as well as to maximize their efficacy.

Such contents are sold in a state of being contained in a predetermined storage container. The conventional contents storage container has a structure including a container main body in which a plurality of contents are contained and a cap that is coupled to an inlet of the container main body so as to be openable and closable.

Therefore, to take or ingest the contents, the cap is opened from the container main body, and then the contents contained in the container main body are withdrawn on a palm or a lid so as to be taken.

The above-described technical configuration is a background art for assisting the understanding of the present invention and does not indicate a widely known related art in the technical field to which the present invention belongs.

A fixed amount discharging container has been proposed in Korean Unexamined Patent Application Publication No. 10-2012-0096798 (Title of Invention: A cap for discharging constant rate of pills).

DISCLOSURE

Technical Problem

The fixed amount discharging container is inconvenient to take out contents one by one or by a necessary demand amount because the contents are poured out when the user takes out the contents by tilting a containing apparatus such as a container apparatus every time to acquire the contents.

Accordingly, a device that allows a fixed amount to be discharged from a containing apparatus has been disclosed conventionally, but an amount of contents discharged from the containing apparatus cannot be accurately sensed, and as a result, it is difficult to guide accurate medication taking.

Therefore, there is a need for improvement.

The present invention has been devised to solve the above-described problems and is directed to providing a contents passing device and a medication management device capable of accurately sensing contents discharged from a containing apparatus and allowing a user to take a fixed amount of contents on the basis of the accurately sensed contents.

Technical Solution

A passing device according to the present invention includes a passing operation part configured to guide movement of contents, a passing movement part rotatably disposed in the passing operation part and configured to move so that the content is passed, and a sensing part disposed in the passing operation part and configured to sense contents discharged due to free rotation of one end of the passing movement part, wherein the sensing part detects information on the sensed contents.

Advantageous Effects

A passing device according to one aspect of the present invention accurately senses discharge of contents and allows a user to take a fixed amount of contents on the basis of the accurately sensed discharge of the contents.

MODES OF THE INVENTION

Figure 1:
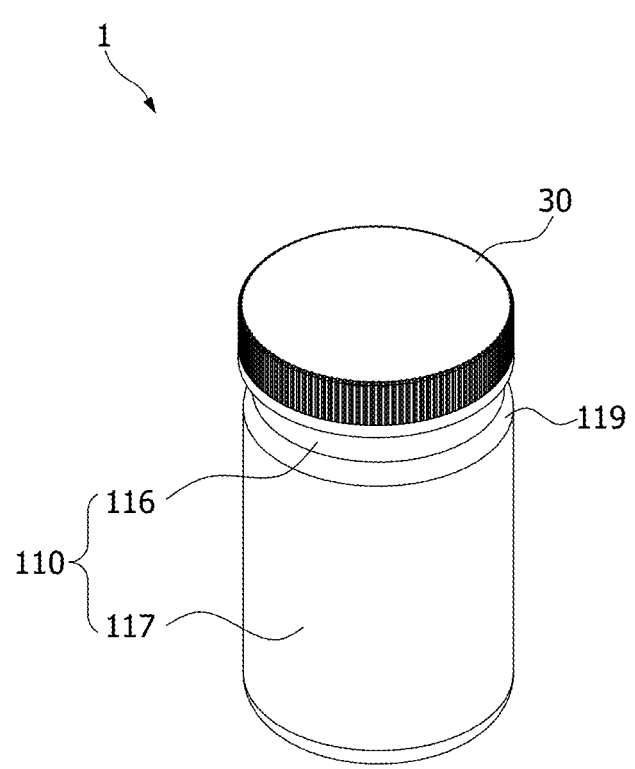
FIG. 1 is a perspective view of a contents moving apparatus including a passing device according to a first embodiment of the present invention.

According to an embodiment of the present invention, a passing device includes a passing operation part configured to guide movement of contents, a passing movement part rotatably disposed in the passing operation part and configured to move so that the contents are passed, and a sensing part disposed in the passing operation part and configured to sense contents discharged due to free rotation of one end of the passing movement part, wherein the sensing part detects information on the sensed contents.

An additional embodiment according to the present invention can be briefly described as follows. The passing movement part may further include a blocking member configured to obstruct passage of contents beyond a predetermined amount. The sensing part may include at least one light emitting part configured to emit light toward contents discharged due to rotation of the passing movement part, at least one light receiving part configured to receive the light emitted from the light emitting part, and a sensing control part configured to sense the contents discharged through the passing operation part by using the light emitted from the light emitting part and then received by the light receiving part.

The present invention may further include a storage part configured to store information on contents detected by the sensing part and further include a measuring part configured to calculate a cumulative discharge amount of contents by period on the basis of the information stored in the storage part. The present invention may further include a display part configured to output the information on the contents detected by the sensing part, the information stored in the storage part, or information calculated by the measuring part.

The present invention may further include a communication part configured to transmit the information on the contents detected by the sensing part, the information stored in the storage part, or the information calculated by the measuring part to an external device through wired or wireless communication.

The sensing control part of the present invention may determine, on the basis of the information stored in the storage part, whether the cumulative discharge amount of the contents by period exceeds or is less than a predetermined amount by period.

The sensing control part of the present invention may determine that the content has been discharged by the passing operation part when reception of light reflected by the content is stopped.

The sensing part of the present invention may further include a tilt sensor configured to sense a slope of the passing device. The sensing control part may determine that the content has been discharged by the passing movement part according to whether a slope of a container sensed by the tilt sensor is within a predetermined slope.

The sensing control part of the present invention may determine that the content has been discharged when radio waves reflected by the content are not received by a receiving part in a state in which a slope of a housing sensed by the tilt sensor is within the predetermined slope and determine that the content has not been discharged when the radio waves reflected by the content are not received by the receiving part in a state in which the slope of the housing sensed by the tilt sensor is beyond the predetermined slope.

The light emitting part and the light receiving part of the present invention may be respectively installed at both sides of the passing movement part.

The sensing control part of the present invention may determine that the content has been discharged by the passing operation part according to a change in a quantity of light that is emitted by the light emitting part, reflected by the content, and then received by the light receiving part.

The sensing control part of the present invention may determine that the content has been passed by the passing operation part when an amount of change in the quantity of light received by the light receiving part is a predetermined amount of change or larger.

The sensing control part of the present invention may determine that the content has been discharged by the passing operation part when the amount of change in the quantity of light received by the light receiving part reaches a state of being the predetermined amount of change or larger and then returns to a state before changing to the predetermined amount of change or larger.

The present invention may further include a tilt sensor configured to sense a slope of a housing, and the sensing control part may determine that the content has been discharged by the passing operation part according to whether the slope of the housing sensed by the tilt sensor is within a predetermined slope.

The sensing control part of the present invention may determine that the content has been discharged when the amount of change in the quantity of light reaches the state of being the predetermined amount of change or larger in a state in which the slope of the housing sensed by the tilt sensor is within the predetermined slope and determine that the content has not been discharged when the amount of change in the quantity of light reaches the state of being the predetermined amount of change or larger in a state in which the slope of the housing sensed by the tilt sensor is beyond the predetermined slope.

The sensing control part of the present invention may determine that the content has been discharged by the passing operation part when the quantity of light received by the light receiving part reaches a state of being a predetermined light quantity or larger and then reaches a state of being less than the predetermined light quantity.

The present invention may further include a tilt sensor configured to sense a slope of a housing, and the sensing control part may determine that the content has been discharged by the passing operation part according to whether the slope of the housing sensed by the tilt sensor is within a predetermined slope.

The sensing control part of the present invention may determine that the content has been discharged when the quantity of light reaches the state of being less than the predetermined light quantity in a state in which the slope of the housing sensed by the tilt sensor is within the predetermined slope and determine that the content has not been discharged when the quantity of light reaches the state of being less than the predetermined light quantity in a state in which the slope of the housing sensed by the tilt sensor is beyond the predetermined slope.

According to an aspect of the present invention, a medication management device includes an output part and a medication guidance terminal control part which is configured to receive medication state information from a sensing part and medication schedule information from a medication management server, generate medication guidance information on a user by using the medication schedule information and the medication state information, and then output the generated medication guidance information to the output part, wherein the output part outputs the medication guidance information by an image or sound.

A passing movement part of a passing device according to still another embodiment of the present invention may include an opening member configured to rotate in a passing direction of contents and form a passing space of the contents. The passing movement part may rotate in the passing direction of the contents due to a self-weight of the contents and allow the passage of a predetermined amount of contents.

The passing operation part may include a fixing member configured to form an opening to pass contents and a movement guide part configured to extend from the fixing member to guide introduction of the contents into a contents passing means.

The passing operation part may be detachably disposed in a housing in which the contents are stored, and the movement guide part may include a contents leading part configured to extend from the movement guide part so as to come in contact with or come close to an inner side surface of the housing that is adjacent thereto and guide the content toward the opening.

The contents leading part may be formed along an inner circumferential surface of the housing.

The movement guide part may include a cover part formed along the inner circumferential surface of the housing and configured to extend from the fixing member to guide movement of the contents stored in the housing toward the opening.

A passing device according to the present invention may include a housing configured to store contents and a passing operation part disposed at an inner side of the housing to guide movement of the contents.

The passing device may include a contents leading part formed in the housing to set a moving direction and a moving state of the contents so that, when the housing is tilted, the contents stored in the housing are guided to be discharged toward the passing operation part one by one or by a fixed amount.

The passing operation part may include a contents passing means configured to allow the contents to move, and the contents passing means may include a passing movement part configured to open by movement and allow the contents to pass.

The passing movement part may include an opening member configured to move in a passing direction of the contents and form a passing space of the contents and a blocking member configured to interlock with the opening member and block at least a portion of an opening to prevent passage of the contents or allow only a portion of the contents to pass. By interlocking with the opening member and blocking at least a portion of the opening, the blocking member may prevent the passage of contents exceeding a fixed amount through the opening.

The passing operation part may include a fixing member configured to form an opening to pass contents and a movement guide part configured to guide introduction of the contents into the contents passing means. The housing may have the fixing member mounted thereon, and movement of the contents toward the movement guide part may be guided through the contents leading part.

The housing may have the fixing member mounted thereon and may include a small diameter part formed so that the movement of the contents toward the movement guide part is guided and a large diameter part having a larger inner space than the small diameter part so that a predetermined amount of contents may be stored therein at an initial stage.

The fixing member may be detachably coupled to the movement guide part.

The contents leading part may be formed in the housing so as to be convex inward and have a curvature along a circumferential trajectory of the housing.

The contents leading part may be formed in the large diameter part or the small diameter part and guide movement of the contents.

The passing operation part may form an opening configured to guide the passage of contents. The passing operation part may form a supply guiding entry part so that the opening is formed to be open toward the contents leading part. The contents stored in the housing may be moved toward the opening through the supply guiding entry part along the contents leading part.

The passing operation part may include a contents passing means configured to allow the contents to move, and the contents passing means may include a passing movement part configured to open by rotation and allow the contents to pass. The passing movement part may open or close the opening by rotating back and forth in the opening with respect to a movement member by using the principle of the lever.

The passing movement part may include a movement control member for setting center-of-gravity balance of lever motion.

The housing may form a passing apparatus neck part so that the contents moving along the contents leading part are guided to be introduced into the passing operation part by a predetermined amount.

The passing movement part may include an opening member configured to move in a passing direction of the contents and form a passing space of the contents, and the passing apparatus neck part may be formed in the housing to guide movement of the contents toward the opening member.

In the housing or the passing operation part, the contents passing means may be rotated while weight balance is adjusted, and a passing apparatus extension part configured to secure a space so that the passage of the contents is guided may be formed.

The passing operation part may include a fixing member configured to form an opening to pass contents and having, in the opening, a contents passing means that allows the movement of a predetermined amount of contents and an inner cap detachably coupled to the fixing member, detachably coupled to a content discharging side of the housing, and configured to allow the discharge of the contents. When the inner cap is detached from the housing, the fixing member may be detached from the housing while being coupled to the inner cap.

The inner cap may be formed in a ring shape, and the fixing member may form an edge part so as to be detachably coupled to an inner side surface of the inner cap.

The inner cap or the housing may have an outer cap detachably disposed therein.

The inner cap or the housing may be hinge-connected to the outer cap.

A passing device according to the present invention may include a passing operation part having an opening and configured to guide movement of contents. The passing operation part may include a contents passing means configured to allow the contents to move. The contents passing means may include a passing movement part configured to open by movement and allow the contents to pass. The passing operation part may form a supply guiding entry part so that the contents may enter the opening from a circumferential surface of the passing operation part along an inner side surface of the housing.

The passing movement part may be disposed in the opening so as to be capable of a seesaw motion, and when the passing operation part is tilted within a predetermined angle due to the seesaw motion, the passing operation part may maintain its initial state so that the opening is not opened.

The predetermined angle may be set as a tilt angle that does not exceed 180° from the initial upright state of a contents moving apparatus having the opening formed therein.

The passing movement part may include an opening member configured to move in a passing direction of the contents and form a passing space of the contents. When the contents moving apparatus having the opening formed therein is tilted within the predetermined angle, the weight of the passing movement part may be leaned toward the opposite side of the direction of tilting, and the opening member may keep the opening blocked.

The passing movement part may perform the seesaw motion due to the weight leaning leftward or rightward with respect to a movement member, which is the center of rotation, according to the principle of the lever.

In a standby state in which the contents moving apparatus having the opening formed therein is tilted, the weight of the passing movement part may be leaned toward the blocking member with respect to the movement member, which is the center of rotation, and the blocking member may get caught in a stopper, and thus the blocking member may keep the opening open without blocking the opening.

Due to a force of the contents pushing the passing movement part or due to the force of the contents pushing the passing movement part and the self-weight of the passing movement part, the opening may be opened, and the passage of a predetermined amount of contents may be guided.

When the contents moving apparatus having the opening formed therein is tilted, the weight of the contents introduced into the opening may be added to the passing movement part, and the passing movement part may be rotated about the movement member, which is the center of rotation, and open the opening.

The passing movement part includes the blocking member configured to interlock with the opening member and block at least a portion of the opening to prevent passage of the contents or allow only a portion of the contents to pass.

When the passing operation part rotates within the predetermined angle, the passing movement part may maintain an initial state due to the stopper when the contents do not come in contact with the passing movement part.

In a state in which the blocking member opens the opening, when the predetermined amount of contents enters between the blocking member and the opening member, the self-weight of the contents may be added to the passing movement part, and the passing movement part may rotate.

The passing movement part may move together with the contents due to friction with the contents that come in contact with a bottom member between the opening member and the blocking member or due to a force of the contents pushing the opening member.

A passing device according to the present invention may include a passing operation part having an opening and configured to guide movement of contents. The passing operation part may include a contents passing means configured to allow the contents to move. The contents passing means may include a passing movement part configured to open by rotation and allow the contents to pass. The passing movement part may open or close the opening by rotating back and forth in the opening with respect to a movement member by using the principle of the lever.

The passing movement part may keep the opening closed by the self-weight when the passing operation part rotates within the predetermined angle and may sequentially open or close the opening by a pushing force of the contents or by a force of the contents pushing the passing movement part and the self-weight of the passing movement part and guide the passage of a predetermined amount of contents.

The passing movement part may include a balance part configured to suppress the passing movement part from tilting beyond a slope of the passing operation part due to the self-weight of the passing movement part when the passing operation part is tilted.

The passing movement part may include an opening member configured to move in a passing direction of the contents and form a passing space of the contents.

The passing movement part may include a blocking member configured to interlock with the opening member and block at least a portion of an opening to prevent passage of the contents or allow only a portion of the contents to pass.

The passing operation part may have a shape such that rotation due to the self-weight of the passing movement part does not occur due to weight balancing before a predetermined amount of contents come into contact with the opening member.

The passing movement part may further include a movement control member for setting center-of-gravity balance of lever motion.

A valve according to the present invention, which is a passing device configured to lead passage of contents, includes a passing operation part configured to pass the contents, wherein the passing operation part includes a contents passing means configured to allow the contents to move.

A contents moving apparatus according to the present invention includes a passing device disposed in the contents moving apparatus, which holds contents, and configured to lead passage of the contents and a housing having at least one open side, wherein the passing device includes a passing operation part configured to allow the contents to pass, and the passing operation part includes a contents passing means configured to allow the contents to move.

A contents moving apparatus according to the present invention includes a housing configured to store contents and a passing operation part configured to guide movement of the contents in the housing.

The passing operation part may include a contents passing means configured to allow the contents to move.

The contents passing means may include a passing movement part configured to open by movement and allow the contents to pass.

The passing movement part may include an opening member configured to move in a passing direction of the contents and form a passing space of the contents.

The passing movement part may rotate in the passing direction of the contents due to a self-weight of the contents coming in contact therewith and allow passage of a predetermined amount of contents.

The passing operation part may include a fixing member configured to form an opening to pass contents and detachably disposed in the housing and a movement guide part configured to guide introduction of the contents in the housing into the contents passing means.

The movement guide part may include a contents leading part configured to extend from the movement guide part so as to come in contact with or come close to an inner side surface of the housing that is adjacent thereto and guide the content toward the opening.

The contents leading part may be formed along an inner circumferential surface of the housing.

The passing operation part may be detachably disposed in the housing, and the movement guide part may be formed in the housing.

A containing apparatus according to the present invention includes a passing device disposed in the containing apparatus, which holds contents, and configured to lead the passage of the contents and a housing having at least one open side, wherein the passing device includes a passing operation part configured to pass the contents, and the passing operation part includes a contents passing means configured to allow the contents to move.

A contents apparatus according to the present invention, which includes contents, includes a passing device configured to lead the passage of the contents and a housing having at least one open side, wherein the passing device includes a passing operation part configured to pass the contents, and the passing operation part includes a contents passing means configured to allow the contents to move.

Hereinafter, a passing device and a medication management device according to an embodiment of the present invention will be described with reference to the accompanying drawings. In this process, the thicknesses of lines, the sizes of elements, or the like illustrated in the drawings may have been exaggerated for clarity and convenience of description. Also, the terms used herein are those defined in consideration of functions in the present invention and may be changed according to an intention or practice of a worker or an operator. Therefore, such terms should be defined on the basis of the contents throughout the present specification.

Figure 2:
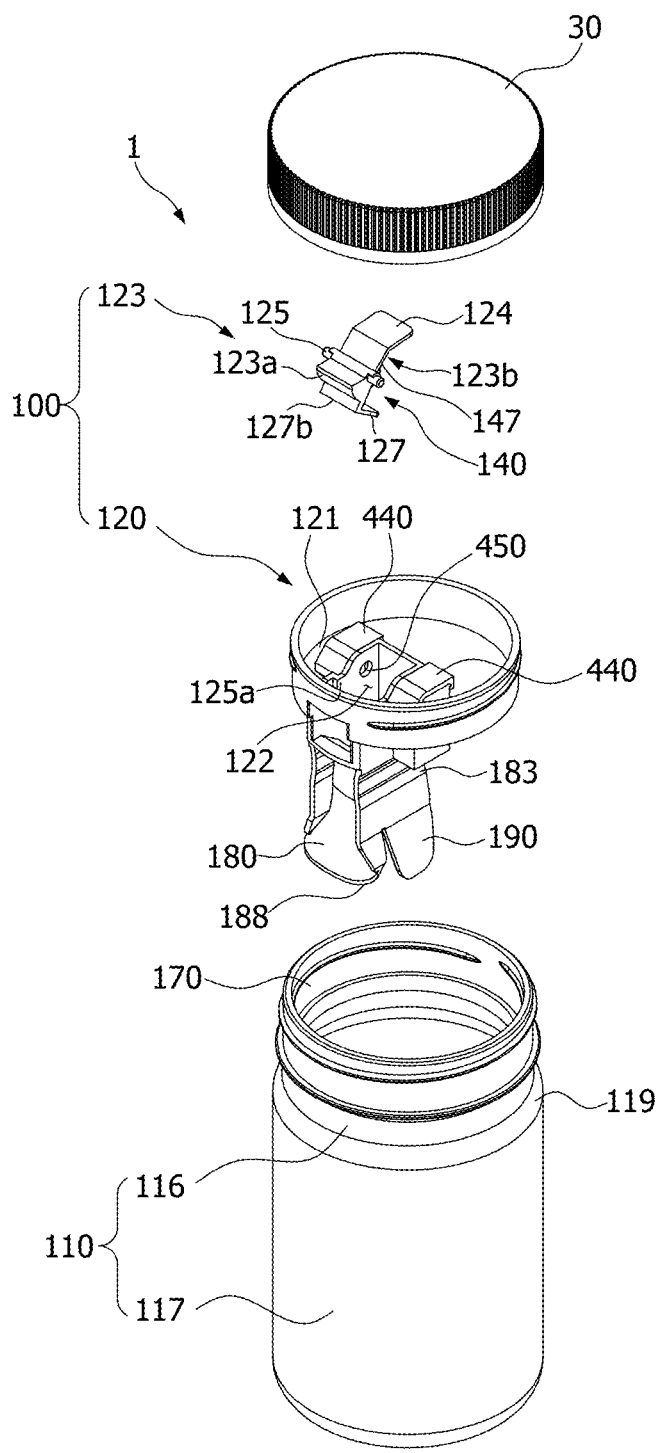
FIG. 2 is an exploded perspective view of the contents moving apparatus including the passing device according to the first embodiment of the present invention.

FIG. 1 is a perspective view of a contents moving apparatus including a passing device according to a first embodiment of the present invention, and FIG. 2 is an exploded perspective view of the contents moving apparatus including the passing device according to the first embodiment of the present invention.

Figure 3:
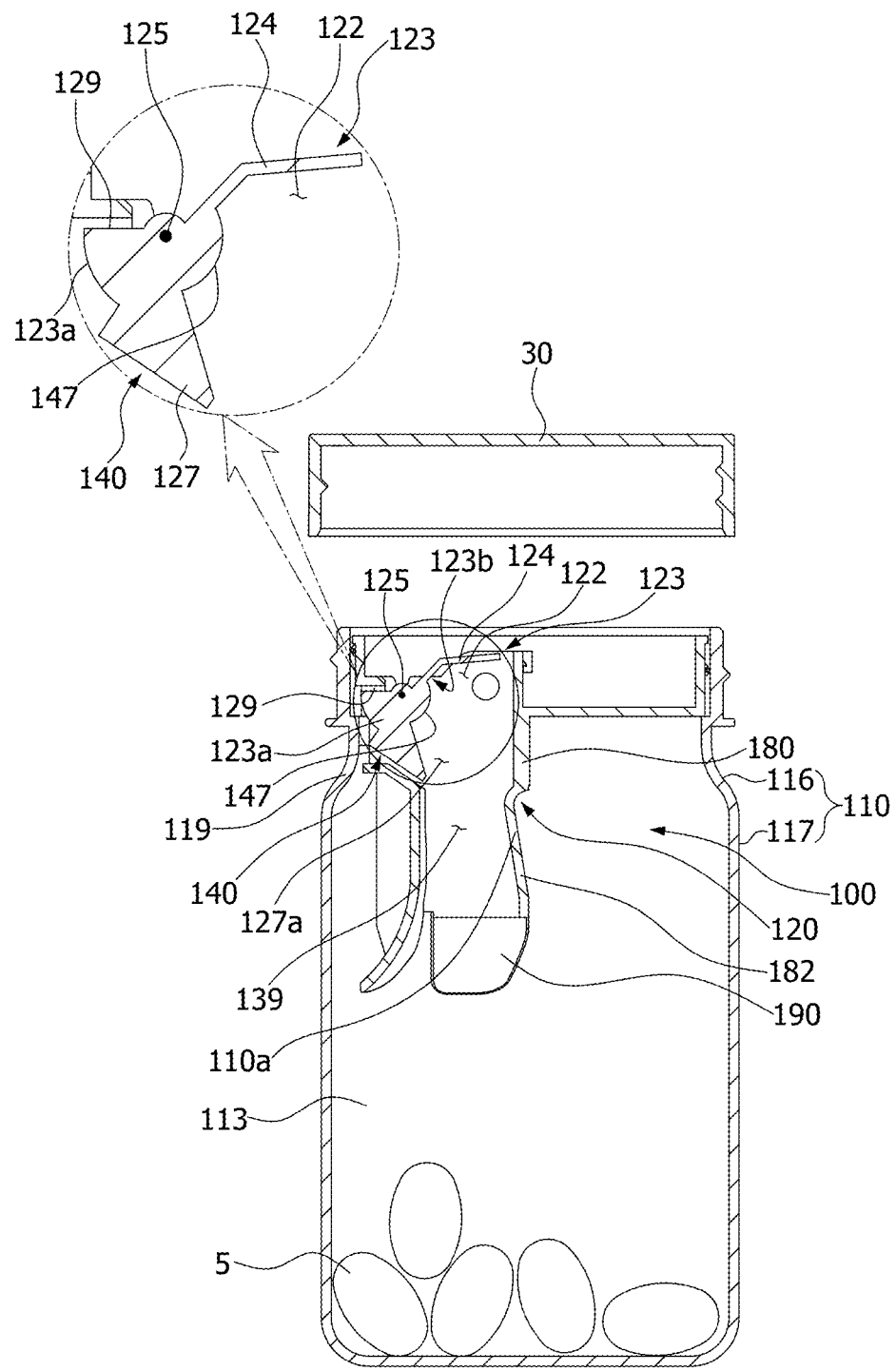
FIG. 3 is a side cross-sectional view of the contents moving apparatus including the passing device according to the first embodiment of the present invention.
Figure 4:
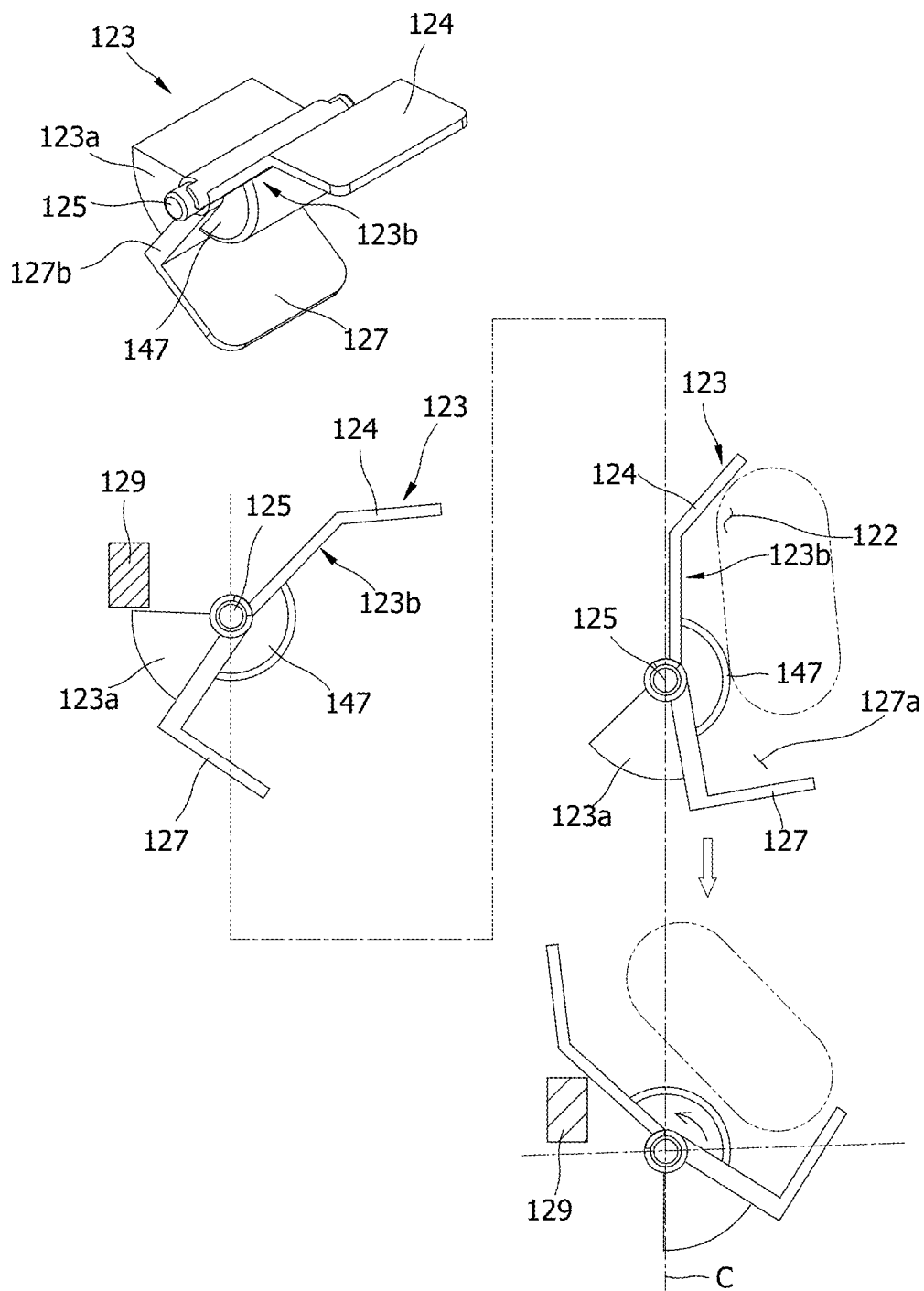
FIG. 4 is a main part view illustrating a tilted state of the passing device according to the first embodiment of the present invention.
Figure 5:
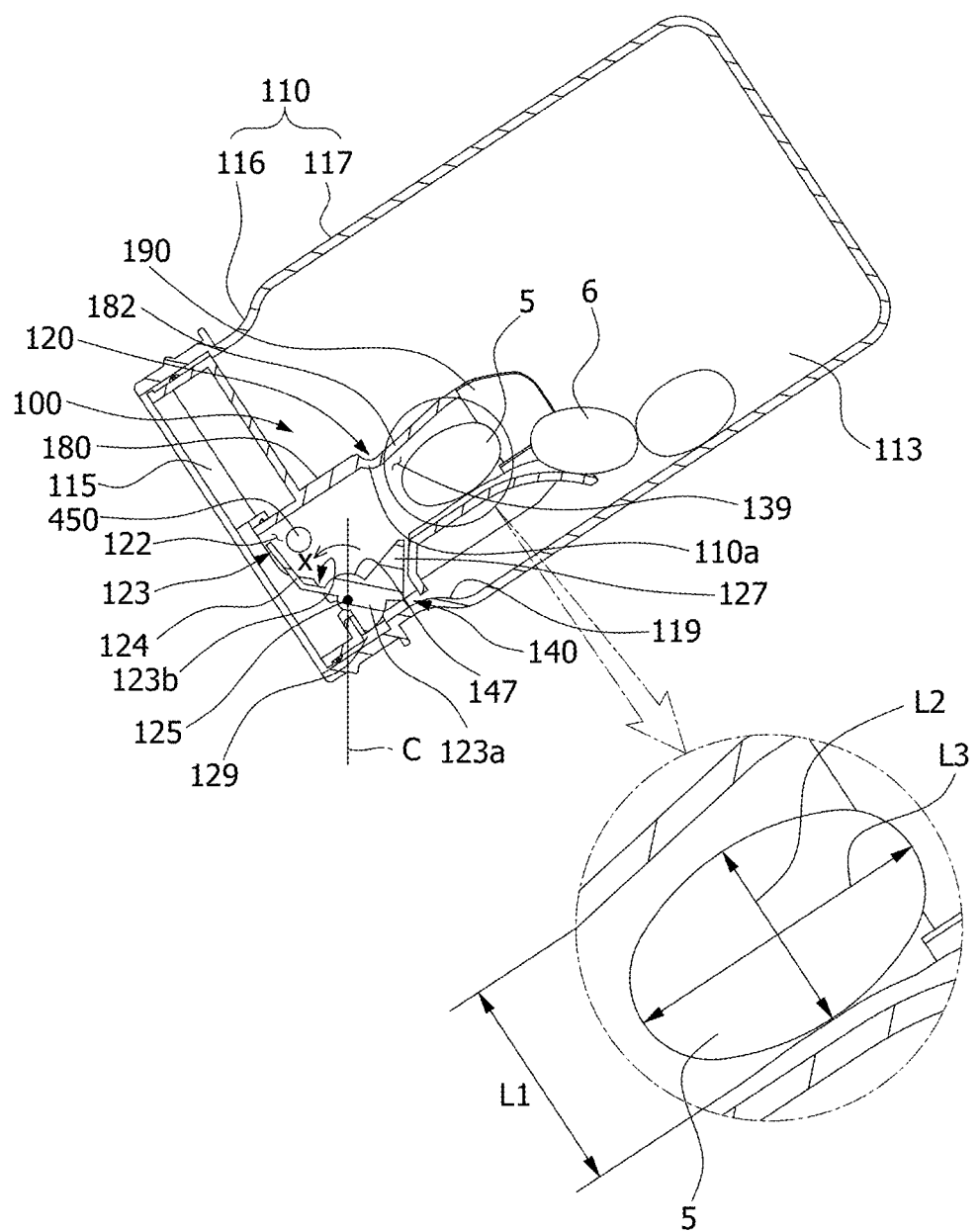
FIG. 5 is a cross-sectional view of a state in which a contents passing means maintains an initial state when a housing of the contents moving apparatus including the passing device according to the first embodiment of the present invention is tilted.
Figure 6:
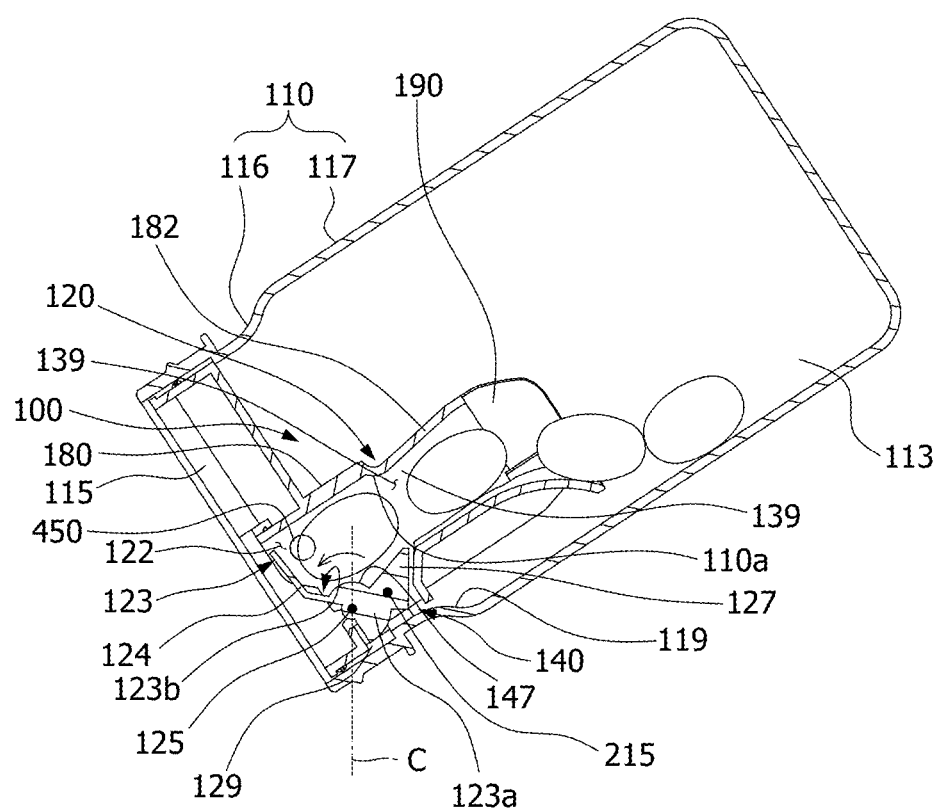
FIG. 6 is a cross-sectional view illustrating a state in which the contents passing means according to the first embodiment of the present invention starts moving due to a pushing force of contents.

FIG. 3 is a side cross-sectional view of the contents moving apparatus including the passing device according to the first embodiment of the present invention, FIG. 4 is a main part view illustrating a tilted state of the passing device according to the first embodiment of the present invention, FIG. 5 is a cross-sectional view of a state in which a contents passing means maintains an initial state when a housing of the contents moving apparatus including the passing device according to the first embodiment of the present invention is tilted, and FIG. 6 is a cross-sectional view illustrating a state in which the contents passing means according to the first embodiment of the present invention starts moving due to a pushing force of contents.

Figure 7:
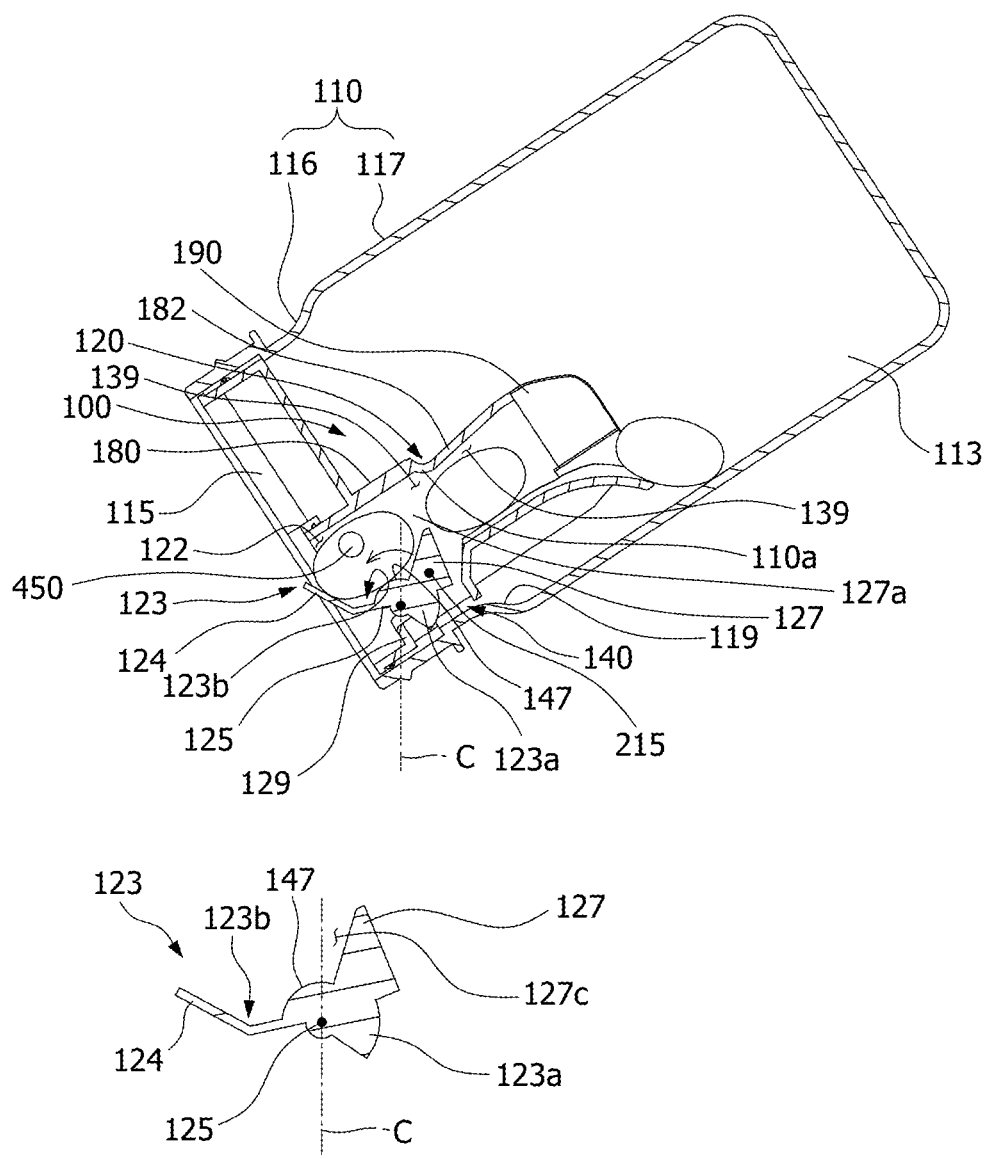
FIG. 7 is a cross-sectional view illustrating a state in which the contents passing means according to the first embodiment of the present invention moves due the pushing force of the contents.
Figure 8:
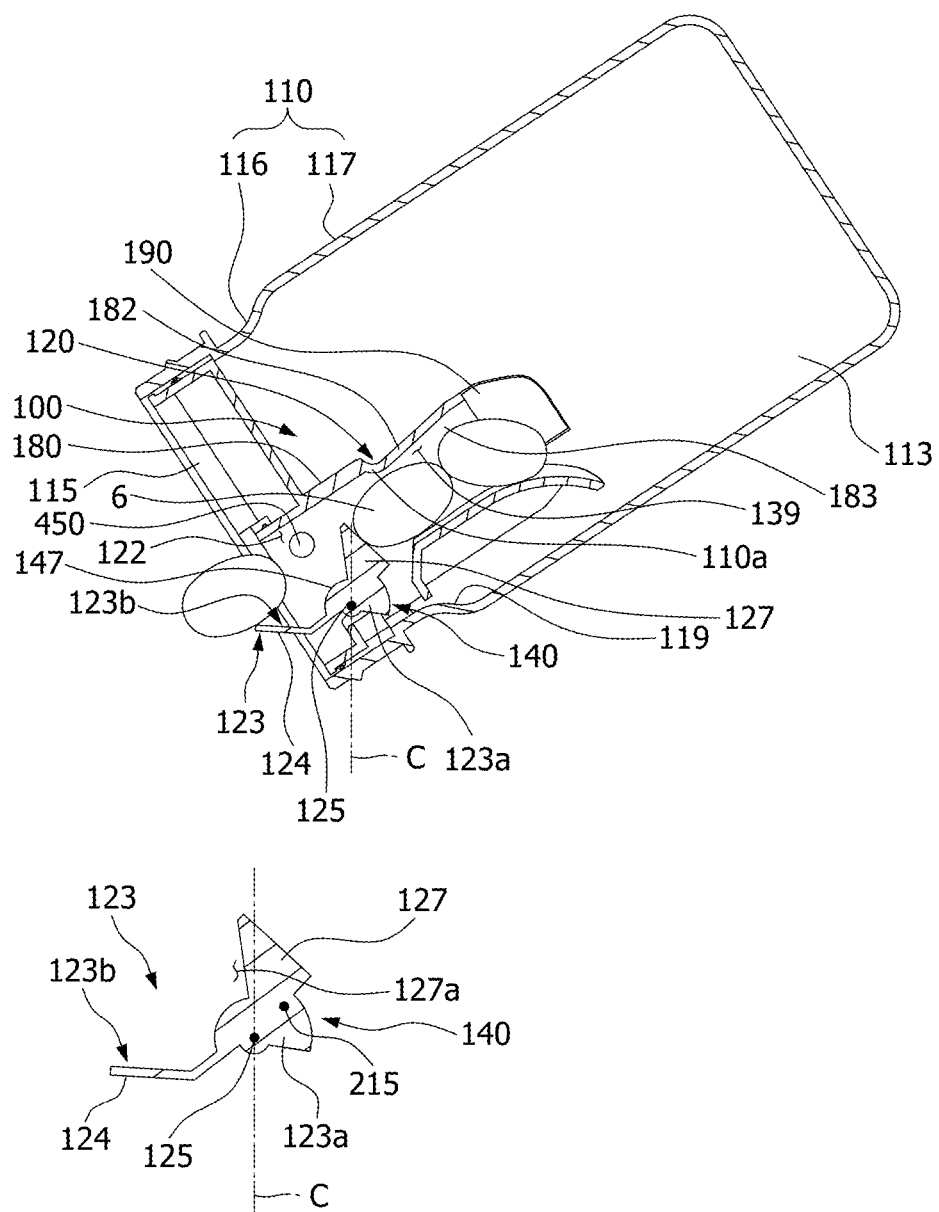
FIG. 8 is a cross-sectional view illustrating the state in which the contents passing means according to the first embodiment of the present invention moves due the pushing force of the contents.
Figure 9:
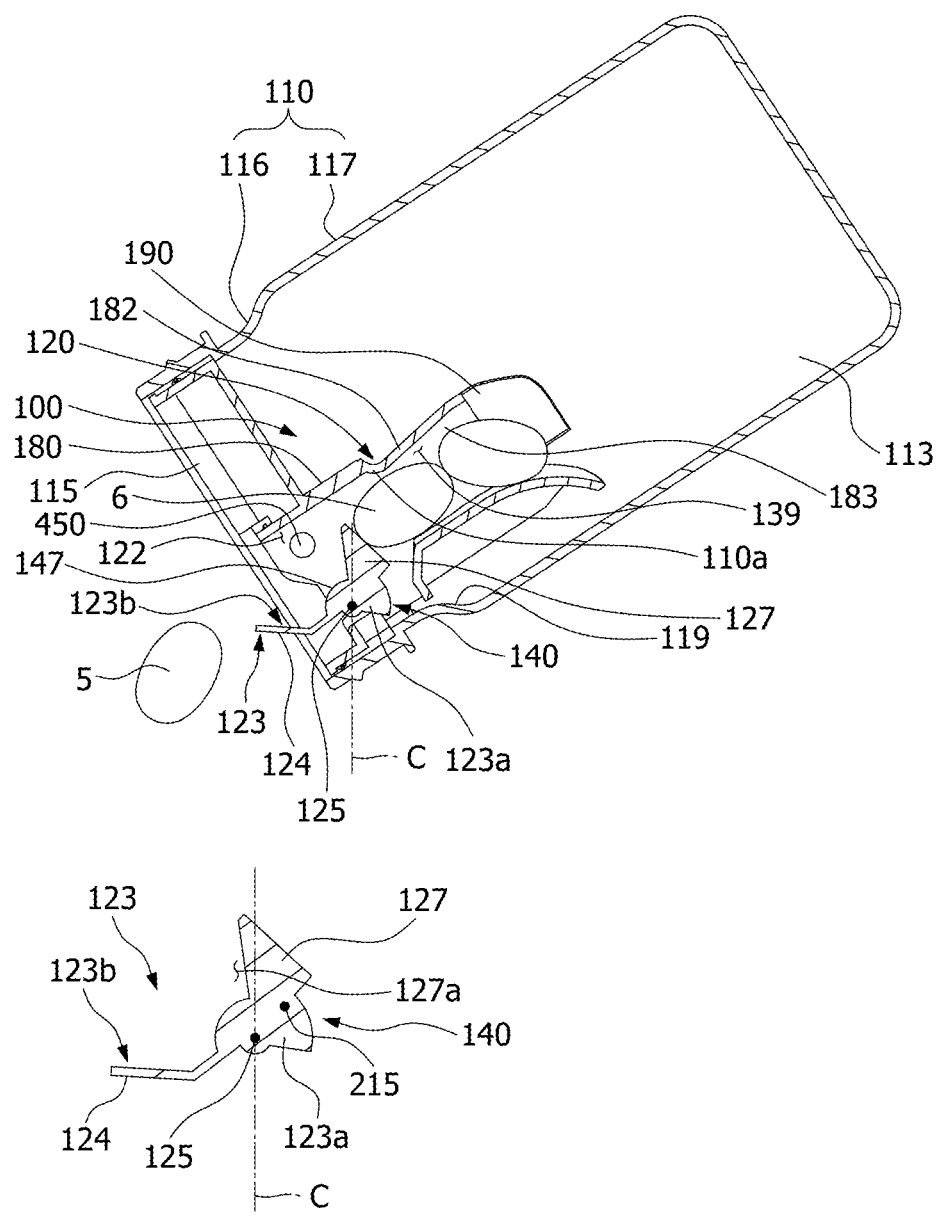
FIG. 9 is a view illustrating a state in which the contents are discharged from the contents passing means according to the first embodiment of the present invention.
Figure 10:
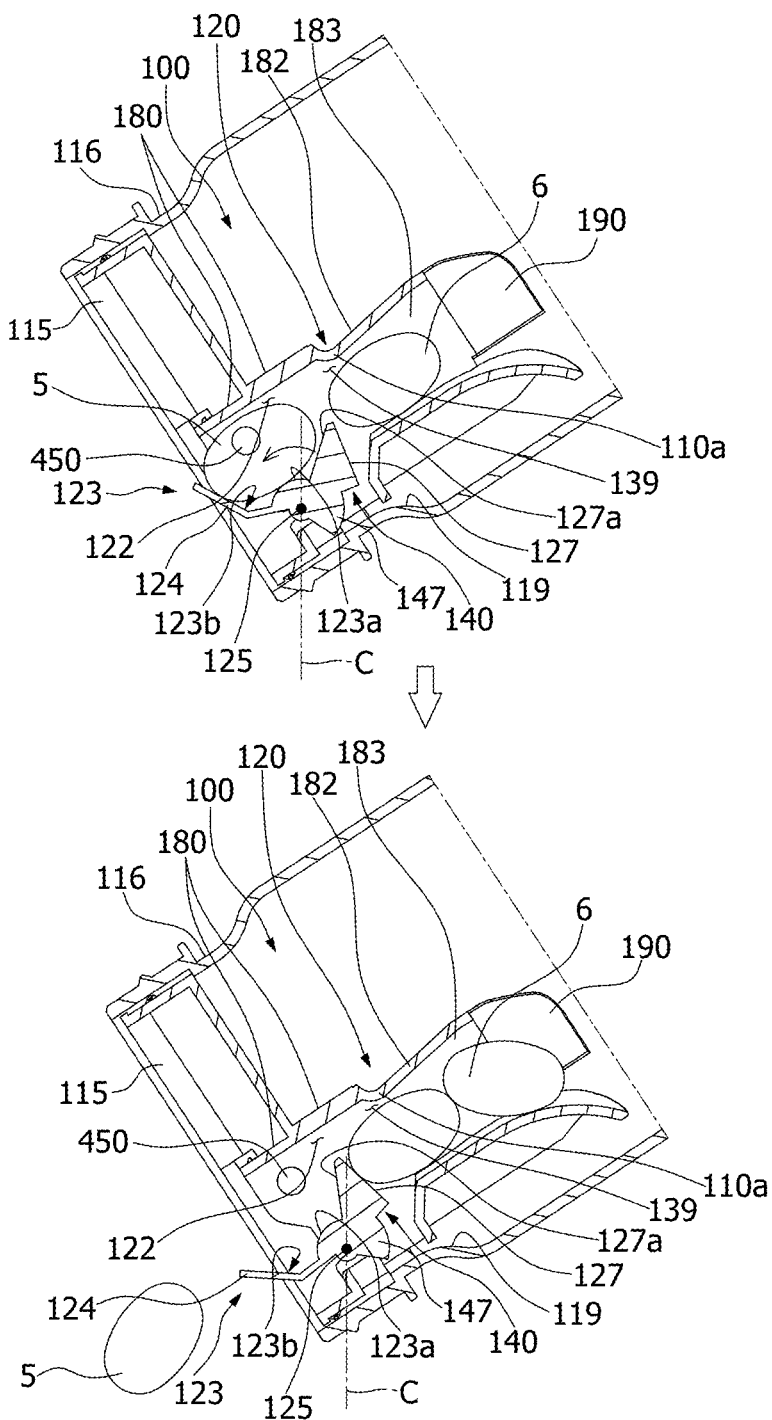
FIG. 10 is a cross-sectional view illustrating a use state of the contents moving apparatus including the passing device according to the first embodiment of the present invention.
Figure 11:
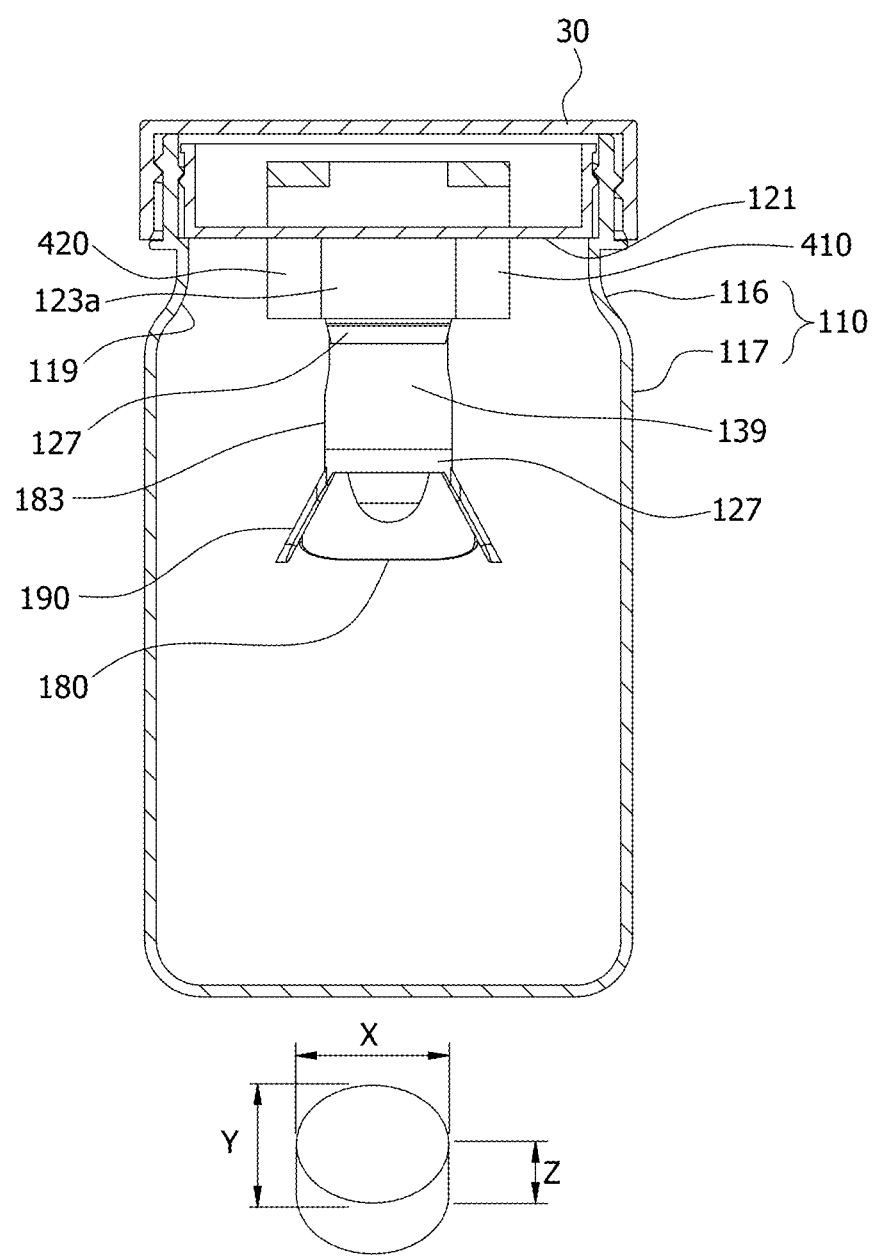
FIG. 11 is a front cross-sectional view of the contents moving apparatus including the passing device according to the first embodiment of the present invention.
Figure 12:
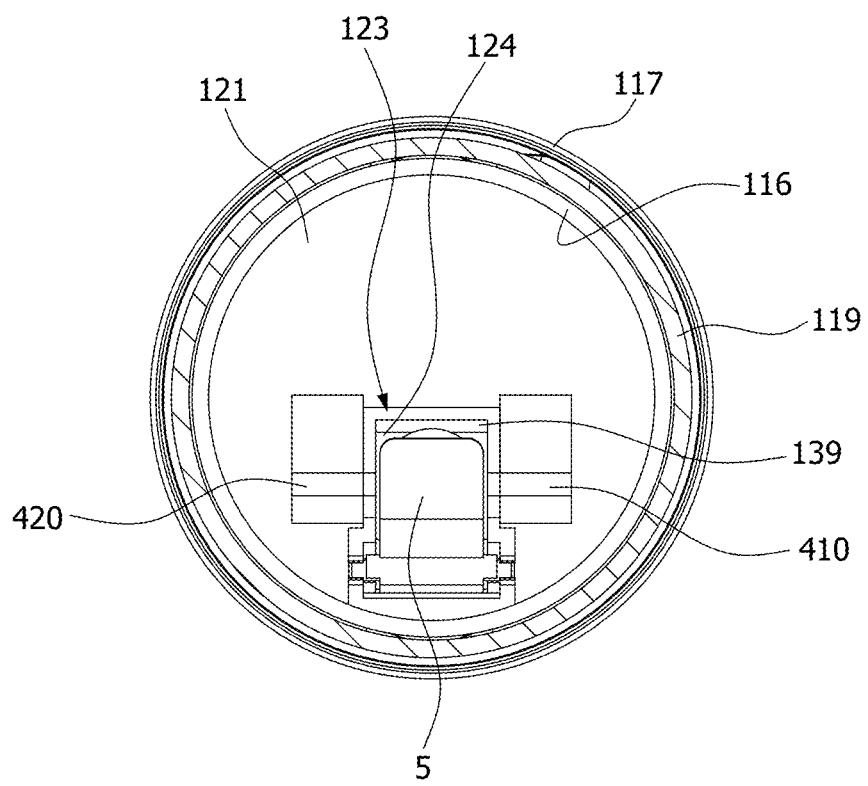
FIG. 12 is a bottom cross-sectional view of the contents moving apparatus including the passing device according to the first embodiment of the present invention.
Figure 13:
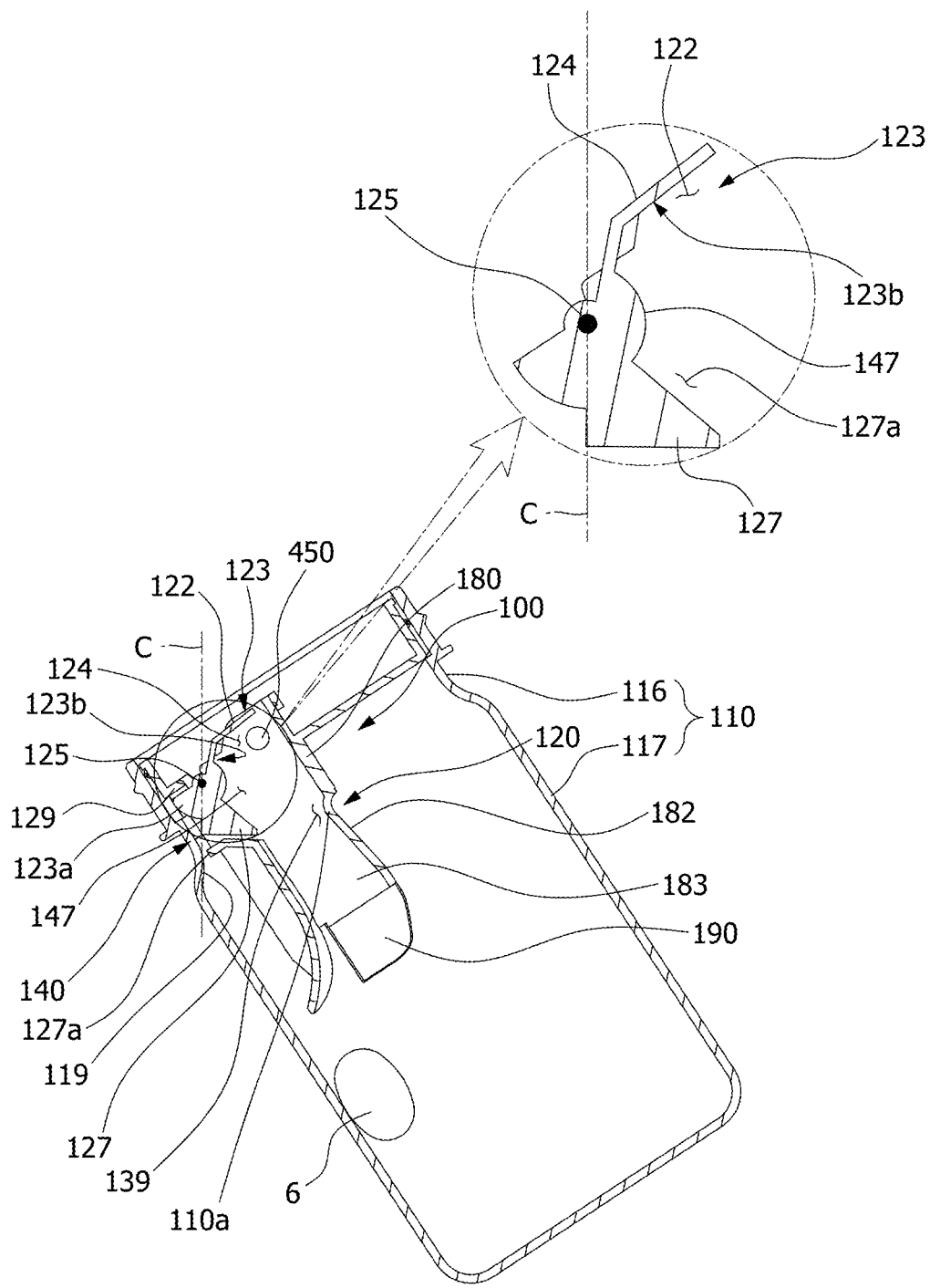
FIG. 13 is a cross-sectional view illustrating a state in which the contents moving apparatus including the passing device according to the first embodiment of the present invention is returned to its initial state after use.
Figure 14:
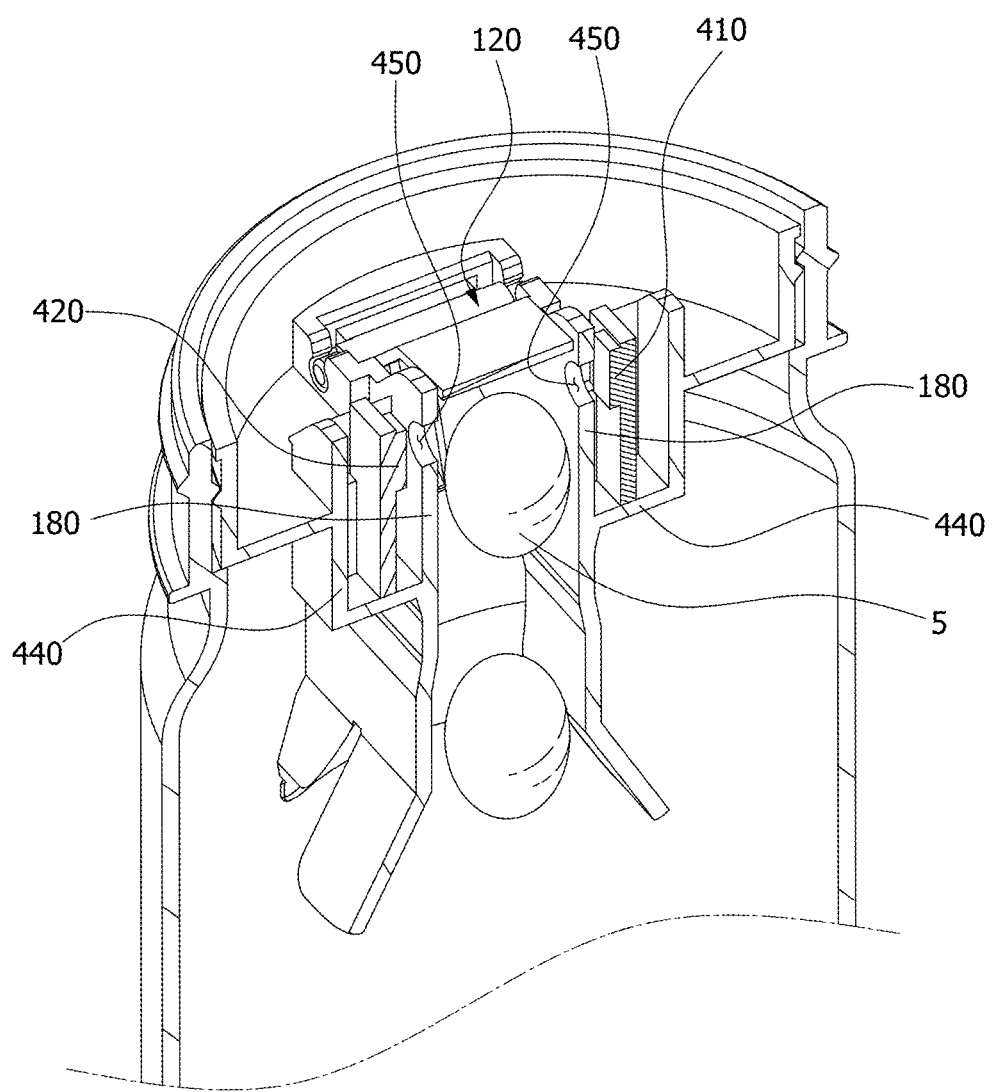
FIG. 14 is a cross-sectional view illustrating an example of an installation structure of a sensor part according to the first embodiment of the present invention.

FIG. 7 is a cross-sectional view illustrating a state in which the contents passing means according to the first embodiment of the present invention moves due the pushing force of the contents, FIG. 8 is a cross-sectional view illustrating the state in which the contents passing means according to the first embodiment of the present invention moves due the pushing force of the contents, FIG. 9 is a view illustrating a state in which the contents are discharged from the contents passing means according to the first embodiment of the present invention, FIG. 10 is a cross-sectional view illustrating a use state of the contents moving apparatus including the passing device according to the first embodiment of the present invention, FIG. 11 is a front cross-sectional view of the contents moving apparatus including the passing device according to the first embodiment of the present invention, FIG. 12 is a bottom cross-sectional view of the contents moving apparatus including the passing device according to the first embodiment of the present invention, FIG. 13 is a cross-sectional view illustrating a state in which the contents moving apparatus including the passing device according to the first embodiment of the present invention is returned to its initial state after use, and FIG. 14 is a cross-sectional view illustrating an example of an installation structure of a sensor part according to the first embodiment of the present invention.

As illustrated in FIGS. 1 to 14, a contents moving apparatus 1 including a passing device 100 according to the first embodiment of the present invention includes a housing 110, a passing operation part 120, and a passing apparatus entry part 119.

The housing 110, which is a container for storing contents 5, includes the passing operation part 120 therein and forms the passing apparatus entry part 119.

Here, the contents 5 are in the form of solid, powder, or liquid that can pass through a contents passing means 123.

In this case, the housing 110 forms a before-passing part 113 which is a portion in which the contents 5 are stored before reaching the passing operation part 120. Further, the housing 110 may form a standby containing part 115 in a space in which the contents 5 are located after passing the passing operation part 120.

That is, the before-passing part 113 refers to a space inside the housing 110 in which the contents are stored, and the standby containing part 115 refers to a space or an open side in which the contents 5 stand by for withdrawal.

The before-passing part 113 and the standby containing part 115 may partially communicate with each other through an opening 122 formed in the passing operation part 120, and the contents 5 in the before-passing part 113 may be moved to the standby containing part 115 through the opening 122.

Therefore, the passing operation part 120 is disposed at an inner side of the housing 110 and serves to guide movement of the contents 5. The passing operation part 120 serves to lead movement of the contents 5 by a fixed amount or a demand amount. Here, "fixed amount" refers to the same number or amount or the amount or number varying within an error range. "Demand amount" is an amount (number) required by a user and belongs to the category of "fixed amount."

Particularly, the passing operation part 120 includes the contents passing means 123 and a passing passage part 139.

The contents passing means 123 serves to allow passage of the contents 5 from the before-passing part 113 to the standby containing part 115.

Particularly, the contents passing means 123 includes a passing movement part 140.

The passing movement part 140 serves to open by movement and allow the contents 5 to pass.

That is, the passing movement part 140 serves to interlock with an opening member 124 and close the opening 122 that is open. Here, the passing movement part 140 includes a blocking member 127 and the opening member 124.

For example, in an embodiment in which a single content is a fixed amount, when a single content 5 passes through a front portion of the passing passage part 139, another single content 5, which is behind and adjacent to the content 5 that passed through the front portion of the passing passage part 139, passes through a rear portion of the passing passage part 139, and the content 5 that passed through the rear portion of the passing passage part 139 moves and comes into contact with the blocking member 127.

Here, the blocking member 127 may be bent, and a blocking member bending part 127b of the blocking member 127 may be linearly bent or formed as a curved surface.

A slope of the blocking member bending part 127b at which the blocking member 127 is bent may be steep and be close to the right angle so that contents beyond a demand amount cannot enter the passing operation part 120. Bending is possible at various other angles.

Then, the blocking member 127 blocks at least a portion of the opening 122 and prevents the contents 5 beyond a fixed amount from being introduced into the opening 122.

Particularly, in an initial state in which the housing 110 stands upright on a floor as in FIG. 3, a state in which the opening member 124 blocks the opening 122 may be maintained by action of a weight balancing force on the passing movement part 140 or by the passing movement part 140 using a stopper 129.

That is, as illustrated in FIG. 3, although a force attempting to rotate clockwise with respect to a movement member 125 due to a self-weight of the opening member 124 acts on the passing movement part 140, the stopper 129 prevents clockwise rotation of the passing movement part 140.

By the opening member 124 blocking the opening 122 while the housing 110 stands upright as in a general container storage state, foreign substances such as air or dust are suppressed from entering the housing 110 through the opening 122.

Further, as in FIG. 3, in the initial state in which the housing 110 stands upright (0° rotation state), a rightward weight leaning action of the passing movement part 140 attempting to rotate clockwise is suppressed by the stopper 129 due to action of a force attempting to move to a weight balanced state, and thus the weight balanced state (standstill state) is maintained. Particularly, when the passing movement part 140 is in the rightward weight leaning state, the stopper 129 at an upper left end suppresses clockwise rotation of the passing movement part 140.

The stopper 129 may be changed to have various shapes and be located at various positions.

In the initial state in which the container stands upright as in FIG. 3, a sensor part 510, which will be described below, may be caused not to operate. Because power loss occurs when the sensor part 510 continuously operates, in order to reduce power consumption, a separate tilt sensor 530 may be mounted and the sensor part 510 may be switched from a standby state to an operating state when the tilt sensor 530 operates.

The sensor part 510 and the tilt sensor 530 will be described below.

FIG. 4 illustrates a state of the passing movement part 140 as the housing 110 is tilted to guide passage of the contents 5. Particularly, the passing movement part 140 is rotated (moved) in both directions with respect to the movement member 125 (indicated by "C").

Also, FIG. 5 illustrates a state of the passing movement part 140 when the housing 110 is tilted 135° counterclockwise from the initial state.

That is, when the housing 110 is tilted 135° counterclockwise, although the housing 110 is tilted leftward (with respect to the movement member 125), which is a direction in which the passing movement part 140 is located, the contents 5 do not slide because the housing 110 is not tilted beyond horizontal (−90°).

Particularly, a tilt angle of the housing 110 is not limited. Further, a downward direction along a vertical axis of the rotation axis 125 of the passing movement part 140 indicates the direction of gravity. Although a force of the passing movement part 140 attempting to rotate rightward is generated because a right-side weight is larger with respect to a vertical axis C, actual rotation thereof is prevented by the stopper 129.

That is, while the housing 110 is in a horizontal state (−90°), although the force of the passing movement part 140 attempting to rotate rightward clockwise is generated because the right-side weight with respect to the vertical axis C is larger, actual rotation thereof is prevented by the stopper 129. Therefore, the housing 110 moves as much as rotation about an axis of a wrist without rotation of the passing movement part 140 itself.

The passing movement part 140 moves corresponding to movement of the contents due to the gravitational action and opens the passing operation part 120 so that the contents pass. When the passing operation part 120 is tilted or moved, the passing movement part 140 may move due to one or more of a self-weight of the passing movement part 140, an inertia of the passing movement part 140, and a force of the contents pressing the passing movement part 140.

Rotation of the passing movement part 140 that allows the contents to pass may be performed by gravitational motion of the contents or transmission of movement force of the contents to the passing movement part 140 that is due to tilting, flipping, or shaking of the passing operation part 120 while a movement part center-of-rotation 210, which is a central axis of rotation of the passing movement part 140, is located in the downward direction, which is the direction of gravity, as illustrated in FIGS. 6 to 8.

Also, the rotation of the passing movement part 140 may be performed by movement force caused by pressing the contents passing means 123 by the self-weight of the contents.

When a position of a movement part center-of-gravity 215 of the passing movement part 140 is disposed in the opposite direction of an outside passing direction of the passing device 100, which is behind the position of the movement part center-of-rotation 210 of the passing movement part 140, and, as illustrated in FIG. 5, the movement part center-of-rotation 210, which is the center of rotation of the passing movement part 140, is located in the downward direction, which is the direction of gravity, and the passing operation part 120 is tilted, rotation of the passing movement part 140 may be restrained or delayed due to a difference between the position of the movement part center-of-gravity 215 and the position of the movement part center-of-rotation 210.

Further, the passing passage part 139 serves to limit a movement amount of the contents 5 moving to the contents passing means 123.

Specifically, when a length of one end of a single content 5 passing through the passing passage part 139 is different from a length of the other end thereof, because a passage-width minimal inner diameter L1, which is a minimal inner diameter length of an inner space of the passing passage part 139, is less than or equal to two times a content short-direction maximal outer diameter L2, which is a maximal outer diameter length in the short direction of the single content 5, two or more contents 5 cannot simultaneously enter or pass through the passing passage part 139, and the contents 5 can enter or pass through the passing passage part 139 only one at a time.

Also, when the length of one end of a single content 5 passing through the passing passage part 139 is different from a length of the other end thereof, the passing passage part 139 guides the contents 5 to pass through the passing passage part 139 along a long-direction end length L3.

The contents passing means 123 includes the blocking member 127 configured to interlock with the opening member 124 and close the opening 122 that is open. When a single content 5 passes through the front portion of the passing passage part 139, another single content 5, which is behind and adjacent to the content 5 that passed through the front portion of the passing passage part 139, passes through the rear portion of the passing passage part 139, and the content 5 that passed through the rear portion of the passing passage part 139 moves and comes into contact with the blocking member 127 so that the blocking member 127 blocks at least a portion of the opening 122 and prevents contents beyond a fixed amount from being introduced into the opening 122.

In the case of the present embodiment, for a fixed amount of contents 5, which is a single content 5, to enter up to a position at which the opening member 124 is placed, due to a weight balancing force of the passing movement part 140, the opening member 124 is closed and the blocking member 127 is open as illustrated in FIG. 5 before the contents come into contact with the opening member 124. Such a standby state is maintained before the fixed amount of contents enters the passing operation part 120.

Also, when the fixed amount of contents 5 comes into contact with the opening member 124, as illustrated in FIGS. 7 and 8, the opening member 124 and the blocking member 127 rotate by interlocking with each other, and the opening member 124 is opened while the blocking member 127 is closed. In this case, due to the closed state of the blocking member 127, contents beyond the fixed amount is continuously prevented from entering the opening 122.

The passing movement part 140 is rotatably disposed at a fixing member 121 which corresponds to an inner side surface of the opening 122. When the opening 122 is opened in the order from FIGS. 6 to 8 by an operation of tilting the passing operation part 120 in the order from FIGS. 3 to 5, the contents 5 are withdrawn, and then the passing operation part 120 is returned to an upright position as illustrated in FIG. 12, due to the weight balancing force of the passing movement part 140, the passing movement part 140 is returned to a state in which the blocking member 127 is opened with respect to the movement member 125 as illustrated in FIG. 3 or 12.

Therefore, when the passing operation part 120 is tilted again in the order from FIG. 3, which indicates the returned position, to FIG. 5, for the contents to be withdrawn again, the fixed amount of contents that approaches the passing movement part 140 for the first time may enter without being blocked by the blocking member 127 and come into contact with the opening member 124. By such a rotation operation of the passing movement part 140, all of the contents in the container main body 110 may be withdrawn by the fixed amount at a time.

A movement guide part 180 configured to introduce the contents 5 into the passing passage part 139 is disposed below the passing passage part 139.

Particularly, at least a portion of the movement guide part 180 is formed to be inclined so that the contents 5 are guided along an inclined surface to a position at which the passing passage part 139 is located.

That is, when the housing 110 including the passing operation part 120 is tilted, the contents 5 move along the inclined surface in a direction of gravity of the movement guide part 180.

Particularly, the passing operation part 120 has the opening 122 and is formed so that the opening 122 protrudes to a predetermined height.

Further, because at least a portion of the inclined surface of the movement guide part 180 is curved and formed to be gradually narrowed, the contents 5 are guided to move toward the passing operation part 120 through the narrowing curved surface.

Also, a movement angle of the opening member 124 may be limited by one or more of the stopper 129 disposed in the contents passing means 123 and a cover 30 connected to the housing 110 including the passing operation part 120.

Further, the stopper 129 extends from the movement member 125 and serves to maintain a state in which the blocking member 127 completely blocks the opening 122 while the opening member 124 does not move further. That is, the stopper 129 is formed in the contents passing means 123 or the housing 110 and serves to limit an angle of rotation of the opening member 124.

A contents containing apparatus 1 including the passing device 100 may be a container apparatus.

More specifically, the contents passing means 123 includes the passing movement part 140 configured to open by movement and allow the contents 5 to pass.

Also, the passing movement part 140 includes the opening member 124 configured to move in a passing direction of the contents 5 and form a passing space of the contents 5 and the blocking member 127 configured to interlock with the opening member 124 and block at least a portion of the opening 122 to prevent passage of the contents 5 or allow only a portion of the contents 5 to pass.

Because the blocking member 127 interlocks with the opening member 124 and blocks at least a portion of the opening 122, the blocking member 127 may prevent contents 5 beyond a fixed amount from passing through the opening 122.

Also, the passing operation part 120 includes the fixing member 121 forming the opening 122 to pass the contents, and the movement guide part 180 configured to guide introduction of the contents 5 into the contents passing means 123.

In this case, the contents 5 pass due to deformation of the contents passing means 123, particularly, due to rotation of the opening member 124.

That is, the passing operation part 120 forms the opening 122 communicating with the before-passing part 113 in which the contents 5 are located before passing and allows passage of the contents 5 located in the before-passing part 113. Particularly, the contents passing means 123 moves the contents 5 through the opening 122.

In other words, the passing space of the contents 5 may be formed due to movement of an unfixed free end of the opening member 124 caused by at least one of pressing by the weight of the contents 5, shaking of the housing 110 including the passing operation part 120, and the self-weight of the opening member 124.

Meanwhile, the passing device 100 may be an opening-closing apparatus that is applied to the contents moving apparatus 1 or containing apparatus and can be opened and closed from a main body of the contents moving apparatus 1 or containing apparatus.

Also, the passing device 100 includes the passing operation part 120. Further, the passing operation part 120 guides movement of the contents 5 in the before-passing part 113 of the main body of the contents moving apparatus 1 or containing apparatus toward the passing device 100. Here, the main body of the contents moving apparatus 1 or containing apparatus may refer to the housing 110.

Further, the passing movement part 140 includes the movement member 125. The movement member 125 may movably connect the opening member 124.

The passing operation part 120 includes the passing passage part 139 formed to extend from a passing discharge side, which is a side at which the contents 5 come into contact with the contents passing means 123, to a passing entry side, which is a side at which the contents 5 enter.

Also, the passing passage part 139 serves to guide movement of the contents 5 to the contents passing means 123.

Further, the passing movement part 140 may include a balance part 123b configured to suppress the passing movement part 140 from being tilted together with the passing operation part 120 at a slope exceeding the slope of the passing operation part 120 when the passing operation part 120 is tilted.

The passage of the contents 5 is guided through the opening 122 according to whether the passing space formed by movement of the opening member 124 is open. In this case, the opening member 124 may be directly or indirectly connected to the fixing member 121.

In other words, when the passing operation part 120 is tilted toward the passing device 100, which is a direction in which the contents 5 slide, a weight leaning force in the opposite direction of the direction in which the passing operation part 120 is tilted acts on the passing movement part 140, and the opening member 124 is suppressed from being tilted due to the self-weight of the opening member 124 by a tilt angle of the passing operation part 120 or more in the direction in which the passing operation part 120 is tilted.

Further, the balance part 123b is configured so that a force attempting to rotate in the opposite direction of tilting of the passing operation part 120 that is tilted to pass the contents 5 is generated in a weight balanced state of the balance part 123b. Therefore, by weight balancing of the balance part 123b, the opening member 124 is not leaned back in the direction in which the passing operation part 120 is tilted, and the force attempting to rotate in the opposite direction of tilting of the passing operation part 120 acts on the opening member 124.

In this case, the fixing member 121 may be disposed at an inner circumferential surface of an inner through-hole space of the passing device 100 connected to the opening member 124 or may be a member of the housing 110 included in the passing device 100.

Particularly, when the contents move in contact with an outer curved surface of the movement member 125 or an outer surface of the opening member 124 in a passing direction of the contents or an opposite direction of the passing direction, the contents move by being resisted outward from a circumference of a movement fixing part 125a.

In this case, passage of contents beyond a demand amount is prevented because an available passing space of the opening 122 is narrowed due to the contents moving outward from the circumference of the movement fixing part 125a.

That is, when the contents 5 come into contact with the opening member 124 as the passing operation part 120 is tilted, the weight of the contents 5 is at least partially or entirely added to the balance part 123b, and the weight of the balance part 123b is leaned in the direction in which the passing operation part 120 is tilted. In this case, the balance part 123b rotates in the direction in which the passing operation part 120 is tilted when weight leaning toward the direction in which the passing operation part 120 is tilted that occurs due to the weight of the contents 5 added to the opening member 124 of the balance part 123b exceeds a balance maintaining force attempting to reach a position at which only the balance part 123b, which attempts to rotate in the opposite direction of tilting of the passing operation part 120, is balanced.

Further, because contents move by being pushed in an opposite axial direction along an outer surface, which is the curved surface of the movement member 125, an available passing space through which other contents pass together is not present.

In this case, a protruding configuration formed by a curved surface or the like along the outer surface of the movement member 125 to reduce the available passing space through which other contents pass together is a bottom-height changing member 147. The bottom-height changing member 147 serves to narrow a space of the opening 122, which is opened so that the contents pass, by relatively increasing a height of a bottom of the movement member 125 with which the contents come into contact while passing.

Also, the shape of the passing movement part 140 may be formed or members constituting the passing movement part 140 may be coupled so that, when the housing including the passing operation part 120 is tilted, the weight or the center-of-gravity of the passing movement part 140 or the balance part 123b, which at least includes the opening member 124, does not cause rotation due to the self-weight of the passing movement part 140 before required contents come into contact with the opening member 124.

Also, the contents passing means 123 includes the movement member 125, and the movement member 125 rotatably connects the opening member 124.

Particularly, the passing operation part 120 includes the fixing member 121 including the opening 122 to pass the contents 5.

The contents passing means 123 includes the opening member 124 and the movement member 125.

The opening member 124 is connected to the fixing member 121. Thus, the opening member 124 may move and guide reception of the contents 5 according to whether the opening 122 is opened.

Also, the movement member 125 movably connects the opening member 124.

Therefore, when the contents 5 press the opening member 124, the contents 5 are introduced as the opening member 124 is leaned back, and the blocking member 127 interlocks with the opening member 124 and blocks at least a portion of the opening 122, and thus passage of the contents 5 beyond a demand amount is prevented.

In this case, when the contents moving apparatus or containing apparatus 1 is tilted, due to a force attempting to maintain balance of the center of gravity of the passing movement part 140 or attempting to rotate in the opposite direction of tilting of the contents moving apparatus or containing apparatus 1 to reach the balance, the passing movement part 140 is tilted beyond a slope of the contents moving apparatus or containing apparatus 1 and becomes the balance part 123b that is not tilted further.

In this case, as illustrated in FIG. 5, a direction of the force of the passing movement part 140 or the balance part 123b attempting to maintain balance or attempting to rotate to reach balance is generated by a force of the passing movement part 140 or the balance part 123b attempting to rotate in the opposite direction of tilting of the contents moving apparatus or containing apparatus 1. Particularly, the passing movement part 140 may include a separate movement control member 123a to balance the center of gravity of the passing movement part 140.

When the passing operation part 120 is tilted, the movement control member 123a may prevent the opening member 124 from being tilted by a slope exceeding the slope of the passing operation part 120 by a force attempting to maintain a center-of-gravity position in the direction of gravity by action of a weight balancing force to the center of gravity of the balance part 123b due to weights of the opening member 124 and the movement control member 123a or weights of the opening member 124, the movement control member 123a, and a separate member moving together with the opening member 124.

When the passing operation part 120 is tilted in a direction in which the contents slide toward the passing device 100, a weight leaning force in the opposite direction of the direction in which the passing operation part 120 is tilted acts on the passing movement part 140, and thus the opening member 124 is suppressed from being tilted due to the self-weight of the opening member 124 by the tilt angle of the passing operation part 120 or more in the direction in which the passing operation part 120 is tilted.

In the balance part 123b including the opening member 124, before the contents slide down due to tilting of the passing operation part 120 and come into contact with the opening member 124 such that the weight of the contents is added in the direction in which the passing operation part 120 is tilted and weight leaning occurs in the direction in which the passing operation part 120 is tilted, the opening member 124 is suppressed from moving due to the self-weight of the opening member 124 in a direction in which the opening member 124 is opened for discharge of the contents, and an opening standby state is maintained before the contents come into contact with the opening member 124.

In this way, the passing movement part 140 becomes the balance part 123b, and the balance part 123b may be configured so that a force attempting to rotate in the opposite direction of tilting of the passing operation part 120 that is tilted to pass the contents 5 is generated in a weight balanced state of the balance part 123b. Therefore, by weight balancing of the balance part 123b, the opening member 124 is not leaned back in the direction in which the passing operation part 120 is tilted, and the force attempting to rotate in the opposite direction of tilting of the passing operation part 120 acts on the opening member 124.

Also, the force of the balance part 123b attempting to rotate in the opposite direction of tilting of the passing operation part 120 may be resisted by a member of a contents apparatus such as the fixing member 121 or the housing 110, and rotation in the opposite direction of tilting of the passing operation part 120 may be suppressed from occurring. Therefore, the balance part 123b is not leaned back in the direction of tilting of the passing operation part 120 due to the force attempting to maintain a balanced state or rotate in a balancing direction of the balance part 123b, and rotation in the opposite direction of tilting of the passing operation part 120 is resisted by the fixing member 121 or the housing 110 and suppressed by the force attempting to maintain the balanced state or rotate in the balancing direction of the balance part 123b.

When the contents come into contact with the opening member 124 as the passing operation part 120 is tilted, the weight of the contents is at least partially or entirely added to the balance part 123b, and weight leaning of the balance part 123b occurs in the direction of tilting of the passing operation part 120, which is a leftward direction in FIGS. 7 and 8. In this case, when the weight leaning in the direction of tilting of the passing operation part 120 that occurs due to the weight of the contents added to the opening member 124 of the balance part 123b exceeds a balance maintaining force attempting to reach a position at which only the balance part 123b, which attempts to rotate in the opposite direction of tilting of the passing operation part 120, is balanced, the balance part 123b rotates in the direction of tilting of the passing operation part 120. In this case, due to the rotation of the balance part 123b having contact resistance with a member of the contents apparatus such as the fixing member 121 or the housing 110, the balance part 123b may be suppressed from rotating more than necessary in the direction of tilting of the passing operation part 120.

When the passing operation part 120 is tilted together with the contents moving apparatus or containing apparatus 1, the balance part 123b or the passing movement part 140 is not tilted beyond the slope of the passing operation part 120 due to action of a force attempting to balance the weight around the center of gravity of the balance part 123b or the passing movement part 140, and the balance part 123b or the passing movement part 140 may maintain its position and slope in the passing operation part 120.

That is, the passing movement part 140 may be disposed in the opening 122 so as to be capable of a seesaw motion, and when the passing operation part 120 is tilted within a predetermined angle due to the seesaw motion, the passing operation part 120 may maintain its initial state so that the opening member 124 does not open the opening 122.

Due to a force of the contents pushing the passing movement part 140 or due to the force of the contents pushing the passing movement part 140 and the self-weight of the passing movement part 140, the opening 122 is opened, and the passage of a predetermined amount of contents is guided.

A predetermined angle may be set as a tilt angle that does not exceed 180° from the initial upright state of the contents moving apparatus or containing apparatus 1 having the opening 122 formed therein.

The passing movement part 140 may perform the seesaw motion due to weight leaning leftward or rightward with respect to the movement member 125, which is the center of rotation.

In a standby state in which the contents moving apparatus or containing apparatus 1 having the opening 122 formed therein is tilted, the weight of the passing movement part 140 may be leaned toward the blocking member 127 with respect to the movement member 125, which is the center of rotation, and the blocking member 127 may get caught in a stopper and keep the opening 122 open without blocking the opening 122.

When the contents moving apparatus or containing apparatus 1 having the opening 122 formed therein is tilted within the predetermined angle, the weight of the passing movement part 140 may be leaned toward the opposite side of the direction of tilting, and thus the opening member 124 may keep the opening 122 blocked.

When the contents moving apparatus or containing apparatus 1 having the opening 122 formed therein is tilted, the weight of the contents introduced into the opening 122 may be added to the passing movement part 140, and the passing movement part 140 may be rotated about the movement member 125, which is the center of rotation, and open the opening 122.

In this way, the passing movement part 140 may open or close the opening 122 by rotating back and forth in the opening 122 with respect to the movement member 125 by a weight balancing principle of a seesaw lever.

The passing movement part 140 may keep the opening 122 closed by the self-weight when the passing operation part 120 rotates within the predetermined angle and may sequentially open or close the opening 122 by the pushing force of contents or by the force of the contents pushing the passing movement part 140 and the self-weight of the passing movement part 140 and guide passage of a predetermined amount of contents.

The passing movement part 140 may include the balance part 123b configured to suppress the passing movement part 140 from being tilted beyond the slope of the passing operation part 120 due to the self-weight of the passing movement part 140 when the passing operation part 120 is tilted.

The passing movement part 140 may include the opening member 124 configured to move in the passing direction of the contents and form a passing space of the contents.

The passing movement part 140 may include the blocking member 127 configured to interlock with the opening member 124 and block at least a portion of the opening 122 to prevent passage of the contents or allow only a portion of the contents to pass.

The passing operation part 120 or the contents passing means 123 may have a shape such that rotation due to the self-weight of the passing movement part 140 does not occur due to weight balancing before a predetermined amount of contents come into contact with the opening member 124.

The passing movement part 140 may further include the movement control member 123a for setting center-of-gravity balance of lever motion.

The passing operation part 120 includes a resistive member 110a disposed therein, and the resistive member 110a limits passage of contents passing inside the passing operation part 120.

The passing operation part 120 includes the resistive member 110a disposed therein. The resistive member 110a may limit passage of contents passing inside the passing operation part 120 and resist passage of the contents in conjunction with the blocking member 127.

The resistive member 110a may protrude toward the inside of the passing operation part 120 so that entry of contents beyond a demand amount is not easy. Also, the resistive member 110a may more effectively block entry of contents beyond the demand amount in conjunction with the blocking member 127 that moves.

The resistive member 110a may be formed in various ways. For convenience, the resistive member 110a is illustrated as being formed by a portion of a resistive upper plate member 182 being concavely recessed inward.

Also, the passing movement part 140 includes a containing member 127a.

The containing member 127a interlocks with the opening member 124, moves toward the opening member 124, and moves together with the opening member 124 while containing a demand amount of contents.

Further, the contents 5 come into contact with any one of the resistive upper plate member 182 and a resistive side plate member 183, and a remaining amount of contents that passed through the opening 122 is limited.

The resistive upper plate member 182 may be disposed at the movement guide part 180, and the resistive side plate member 183 may be connected to the resistive upper plate member 182 or the fixing member 121.

Particularly, the resistive side plate member 183 may be formed at a surface of the fixing member 121 toward the passing direction of the contents 5, but, when the cover 30 that is open is disposed, the resistive side plate member 183 is formed at the cover 30 so that, when the cover 30 is opened, the resistive side plate member 183 moves together with the cover 30 and does not interfere when the contents are picked up.

Of course the resistive upper plate member 182 and the resistive side plate member 183 may be changed to have various other shapes in the passing direction of the contents 5 and a side direction of passing.

Also, the movement guide part 180 has a contents leading part 188 formed at an entry side for the contents 5. The contents leading part 188 divides a height difference generated during movement of the contents to the contents passing means 123 into a plurality of stages or configures the height difference as an inclined surface to prevent the height difference from blocking movement of contents and lead movement of the contents so that contents in the before-passing part 113 are led to stably move to the passing passage part 139. Of course the contents leading part 188 may be changed to have various other shapes.

Meanwhile, the passing device 100 further includes the passing apparatus entry part 119.

The passing apparatus entry part 119 is formed in the housing 110 to set a moving direction and a moving state of the contents 5 so that the contents 5 moving to a discharge side of the passing operation part 120 are guided to be discharged one by one or by a fixed amount.

Particularly, the housing 110 includes a small diameter part 116 and a large diameter part 117.

The small diameter part 116 mounts the fixing member 121 and is formed to have a small diameter so that the contents 5 are guided to move toward the movement guide part 180. In this case, the diameter of the small diameter part 116 is similar to or same as a circumferential trajectory formed along the contents leading part 188, a guide member 190, and the resistive upper plate member 182.

Also, the large diameter part 117 is formed to have a larger inner space than the small diameter part 116 to initially store a predetermined amount of contents. Of course the diameter of the large diameter part 117 is not limited.

Also, the passing apparatus entry part 119 is formed at a connecting portion between the small diameter part 116 and the large diameter part 117 of the housing 110 and formed to be convex inward and have a curvature along the circumferential trajectory. Thus, the contents 5 are moved along the passing apparatus entry part 119 and guided to be introduced into the contents leading part 188 and the guide member 190 by a fixed amount each time.

Of course the passing apparatus entry part 119 may be changed to have various other shapes.

A sliding start end of the contents leading part 188 that leads the contents to the passing passage part 139 is located in the vicinity of or in contact with an inner diameter of the small diameter part 116, which is a neck portion of the housing 110, which is the container main body of the present embodiment. Therefore, the sliding start end of the contents leading part 188 is disposed to be connected to the passing apparatus entry part 119, which has a curved shape, so that contents smoothly move and slide and are guided to move from the large diameter part 117 to the passing passage part 139.

In an injection blow container, because a pneumatic pressure is applied to an opening of the housing 110 of the container, the small diameter part 116 which is the neck portion narrower than the large diameter part 117, which is a body of the container, is formed.

Therefore, in the case of the injection blow container, an end portion of the contents leading part 188 disposed in the passing device 100 has an inclined, bent, or stepped shape and allows an inner diameter of the container neck (the small diameter part 116) and an inner diameter of the container body (the large diameter part 117) to be entirely or partially connected so that, when the housing 110 is tilted and the contents slide, the contents can smoothly move to the passing passage part 139.

Of course when a step is formed between a contents entry portion of the contents leading part 188 and the large diameter part 117 as in the present embodiment, a shape changing part 119 configured to connect the step between the contents entry portion of the contents leading part 188 and the large diameter part 117 may be disposed. In the case of the present embodiment, the shape changing part 119 is the passing apparatus entry part that connects the step between the small diameter part 116 and the large diameter part 117 and guides supply and movement of contents at the step in the housing.

Also, even in the case of an injection container in which an inlet is not narrower than a container body in addition to the case of the injection blow container of the present embodiment in which the inlet is narrower than the container body, because an operation position of a rotation shaft of the opening member 124 of the passing movement part 140 is disposed to be spaced apart inward from the inner diameter of the housing 110 of the container, there may be a difference between the operation position and a position of solid contents that slide and move, and to connect the step therebetween, the contents entry portion of the contents leading part 188 facing a bottom of the container may have an inclined, bent, or stepped shape.

In the cases of both the injection blow container and the injection container, an operation position of the opening member 124 is disposed inward of an inner diameter of the container, a step difference is formed between the operation position and a position of contents approaching from the container body 117, and the contents leading part 188 having an inclined, bent, or stepped shape to connect the step therebetween is included.

In the container main body (the housing 110) of the present embodiment, which is the injection blow container, because a pneumatic pressure is applied to an upper opening of the body, the small diameter part 116 narrower than the large diameter part 117 is formed.

In the present embodiment, the contents leading part 188 configured to connect the step between the opening member 124, which is disposed to be spaced apart from the inner diameter of the small diameter part 116, and the inner diameter of the small diameter part 116 is disposed.

In the case of the injection blow container as in the present embodiment, the step connecting part 188 connects the inside of the small diameter part 116 of the container and the inside of the container body 117 so that contents slide smoothly.

Also, the passing apparatus entry part 119, which is an inclined portion that connects the small diameter part 116 narrower than the container body 117 and the large diameter part 117 in which contents are stored to stand by for movement, is included. The passing apparatus entry part 119 may serve to connect a step that is generated when the housing 110 is tilted and the contents in the large diameter part 117 move to the contents leading part 188.

Unlike in the present embodiment, when a step start point, which is a step start end of the contents leading part 188 facing the bottom of the container, is larger than the inner diameter of the small diameter part 116, in order to insert the passing device 100 into the housing 110, a lower portion of the passing device 100 that includes the start point of the contents leading part 188 facing the bottom of the container, which is the step start point of the contents leading part 188, has to be first inserted in a vertical direction, the position of the passing device has to be moved in a horizontal direction, and then the passing device 100 has to be inserted again in the vertical direction. Therefore, three steps including vertical movement at the time of assembly, horizontal movement which is an intermediate step, and vertical movement after the horizontal movement are required.

Meanwhile, as in the present embodiment, the start point of the contents leading part 188, at which the contents leading part 188 of the passing device 100 is in the vicinity of the inner diameter of the housing, and the guide member 190 may be disposed inside the small diameter part 116, and thus the passing device 100 may be directly inserted into the housing 110 in one direction at the time of assembly to the housing 110.

Particularly, this is shown in a characteristic of the blow container in which a portion of the container neck 116, which is the small diameter part 116, is produced to be smaller than the container body 117, which is the large diameter part 117, as in the present embodiment. The housing 110, which is the injection blow container, includes a convex body and the small diameter part 116 in which a main portion of the passing device 100 is disposed.

Therefore, when an entire outer diameter of the lower portion of the passing device 100 including the contents leading part 188, which is toward the large diameter part 117, is formed to be smaller than the inner diameter of the small diameter part 116 of the container, at the time of assembling the passing device 100 to the container main body, the passing device 100 is inserted into the housing 110, which is the container main body, at once in one direction without the horizontal movement which is the intermediate step.

Meanwhile, an upper end of the small diameter part 116 may be widely formed or a step may be formed in the small diameter part 116 so that the passing device 100 is assembled to the container main body and supported from top to bottom of the ground.

Also, a protrusion may be formed at an outer diameter of the upper portion of the passing device 100 so that the passing device 100, which is a contents passing dispenser, is prevented from being separated to the outside due to the weight of contents coming into contact with the passing device 100 when the container is tilted, a groove corresponding to the protrusion may be formed at an upper end of the small diameter part 116 of the housing 110, and the protrusion and the groove may be engaged with each other when the passing device 100 is inserted into the housing 110.

A cover of various shapes may be coupled to the upper end of the small diameter part 116.

Of course the housing 110 may be connected in a straight line without differentiation of the large diameter part 117 and the small diameter part 116 or may be formed in other various shapes. That is, the housing 110 may be manufactured in various shapes such as the shape of a container having an equal diameter throughout.

As a result, in the initial upright state, the opening member 124 keeps the opening 122 blocked by the weight balancing force of the passing movement part 140. That is, when a force attempting to rotate toward one side (rightward) is acted, the stopper 129 prevents rotation of the passing movement part 140 toward the one side.

Also, the contents 5 do not slide because the housing 110 is tilted toward the other side (leftward), which is the direction in which the passing movement part 140 is disposed, and is not tilted beyond horizontal. Further, when the container 110 is tilted within a predetermined angle (within 90°), gravity acts downward along the vertical axis of the center of rotation of the passing movement part 140. Thus, even when a weight at one side is larger with respect to the vertical axis and a force attempting to rotate toward the one side is generated, actual rotation is prevented by the stopper 129.

When the housing 110 is horizontal, although a weight at one side with respect to an arbitrary vertical axis becomes larger and a force attempting to rotate toward the one side is generated, actual rotation is prevented by the stopper 129. Therefore, rotation of the passing movement part 140 itself does not occur.

Further, when the housing 110 is tilted beyond horizontal, a standby state without movement of the passing movement part 140 is reached in a state in which the blocking member 127 is open. In this case, the contents 5 slide and move in the direction of gravity along the slope of the inside of the housing 110.

Particularly, even when a step is formed between the housing 110 and the guide member 190, a single content 5 in the form of a tablet may be laid down without being stood upright and enter the guide member 190.

In this case, a state in which a first content 5 of the contents 5 in the housing 110 does not enter a passing compartment part 124*a* disposed between the opening member 124 of the passing movement part 140 and the blocking member 127 is reached.

Further, the contents 5 in a rectangular shape instead of a flat shape stably slide along the slope of the guide member 190 without being stood upright.

In this case, the contents 5 do not come into contact with the passing movement part 140 before the housing 110 is tilted beyond 90°.

Meanwhile, when the housing 110 is tilted beyond 90°, the passing movement part 140 moves (rotates) together with the contents 5 in a space of the passing compartment part 124*a* due to friction between the contents 5 and the bottom-height changing member 147 or the force of the contents 5 pushing the opening member 124.

In this case, because a weight at the left side with respect to the vertical axis, which is the direction of load and gravity of the contents 5, becomes larger than a weight at the right side and the weight leans toward the left side (see FIG. 9), the passing movement part 140 rotates leftward counterclockwise with respect to the center of rotation 125 and passes the contents 5 to the outside.

Although a fixed amount of the contents 5 is discharged to the outside and does not come into contact with the passing movement part 140, the weight at the right side becomes larger, and a force of the passing movement part 140 attempting to rotate rightward is generated, the remaining contents 5 come into contact with the blocking member 127 due to gravity and the state without rotation is maintained.

Particularly, FIG. 5 illustrates a state in which the housing 110 is tilted beyond horizontal (−90° or more). In this case, an initial state without movement (rotation) of the passing movement part 140 is maintained in a state in which the blocking member 127 is opened. The contents 5 slide and begin moving along the slope of the inside of the housing 110 due to a force in the direction of gravity (indicated by "C").

Even when a step is formed between the housing 110 and the guide member 190, a single content 5 in the form of a tablet may be laid down without being stood upright and enter the guide member 190. A state in which the first content (pill 5) has not yet entered the passing compartment part 124*a* disposed between the opening member 124 of the passing movement part 140 and the blocking member 127 is reached.

The contents 5 in the form of a tablet instead of the form of a flat pill stably slide along the slope of the guide member 190 without being stood upright.

Although the passing movement part 140 is in a state of being tilted beyond 90° counterclockwise with respect to the initial state due to the slope of the housing 110, the contents 5 are not in contact with the passing movement part 140. Although the passing movement part 140 attempts to rotate clockwise, which is rightward, due to the weight leaning rightward with respect to the movement member 125, the rotation is suppressed by the stopper 129, and the standby state is maintained.

In FIG. 5, when the housing 110 is tilted by a predetermined slope, e.g., 90° or more, counterclockwise, the contents 5, such as pills, slide and move toward the passing device. In this case, the opening member 124 and the passing movement part 140 maintain the same posture and state without separate self-rotation. In FIG. 5, a quantity of light detected by a light receiving part 420 of the sensor part 510 in a state in which the contents 5 are not moved toward an inside of the blocking member and the contents 5 do not block the light receiving part 420 of the sensor part 510 is large. In this case, the quantity of light received by the light receiving part 420 may be calculated as, for example, about 80%.

FIG. 6 illustrates a state in which the contents 5 enter the inner space of the passing movement part 140 in a state in which the blocking member 127 is open.

Because the self-weight of the contents 5 is added to the balance part 123*b* of the passing movement part 140, and the weight leaning toward the left portion with respect to the vertical axis of gravity (indicated by "C"), which is toward the opening member 124, is relatively increased, due to resistance between the balance part 123*b* and the contents 5, the passing movement part 140 may be tilted beyond the slope of the housing 110 and rotate counterclockwise as the contents 5 approach to come into contact with the opening member 124 or come into contact with the opening member 124.

In this case, the passing movement part 140 moves together with the contents 5 in the space of the passing compartment part 124*a* due to friction between the contents 5, which move in the direction of gravity along a tilted inclined surface, and the balance part 123*b* or the force of the contents 5 pushing the opening member 124.

FIG. 6 shows a state in which the contents 5 are moved to come into contact with the opening member 124 of the passing device. In this case, the quantity of light received by the light receiving part 420 of the sensor part 510 is relatively smaller than that received in the state of FIG. 5 in which the contents 5 are not moved toward the inside of the blocking member, and may be calculated as, for example, 20%.

FIG. 7 illustrates a state in which the passing movement part 140 is further rotated counterclockwise with respect to the movement member 125 from the initial state, and the blocking member 127 begins to block contents 6 that enter after the fixed amount of contents (pills 5).

In this case, the weight leans leftward due to the load of the contents 5, which are in the form of a pill, as well as the left-side weight of the passing movement part 140 becoming larger than the right-side weight thereof with respect to the vertical axis of gravity (indicated by "C"), and the passing movement part 140 may rotate leftward counterclockwise with respect to the center of rotation of the movement member 125 and pass the contents 5 to the outside.

FIG. 7 illustrates a state in which the pills move to be discharged to the outside and the blocking member 127 does not completely block passage of the pills. When a light emitting part 410 transmits a predetermined quantity of light in a state in which the passage of the pills is blocked, the light receiving part 420 receives and measures a small quantity of light in a state in which the pills block transmission of a medium such as light moving from the light emitting part 410 to the light receiving part 420. In this case, the quantity of light received by the light receiving part 420 may be calculated as, for example, about 20%.

When the passing movement part 140 is further rotated counterclockwise with respect to the movement member 125 from the initial state as in FIG. 8, a fixed amount of the contents 5 that was pushing the passing movement part 140 begins to be discharged to the outside and does not come into contact with the opening member 124 of the passing movement part 140 anymore, the right-side weight of the passing movement part 140 becomes larger with respect to the central axis (indicated by "C"), and a force of the passing movement part 140 attempting to rotate clockwise, which is rightward, is generated. However, as the remaining contents 6 come into contact with the blocking member 127 due to gravity, the valve 100 maintains the current state without being restored rightward and does not allow any more contents 5 to enter the space of the passing compartment part 124*a*.

FIG. 8 illustrates a state in which a pill is coming out while pushing the opening member 124 but is not completely discharged to the outside. In this state, the blocking member blocks a second pill from entering.

Although most pills are completely discharged to the outside, an error in which a pill is stuck in a container inlet portion and not completely discharged to the outside may occur. In this case, the quantity of light received may be calculated as, for example, about 50%.

Even in this case, when the pill is stuck with a majority thereof already discharged, a majority of the quantity of light transmitted from the light emitting part 410 may be sensed by the light receiving part 420. The quantity of light received in this case may be calculated as, for example, about 75%.

When the second pill also passes through the blocking member unlike in FIG. 8, two pills may come out, or both the first pill and the second pill may be jammed and not come out.

FIG. 9 illustrates a state in which a pill is completely discharged.

When the light emitting part 410 emits a predetermined quantity of light in a state in which there is no pill, the light receiving part 420 receives and measures a received quantity of light in a state in which the passage of light is not blocked by pills. In this case, an amount of change in the quantity of light received by the light receiving part that occurs due to a change in movement of the passing movement part 140 may be considered as a compensation value. For example, the quantity of light received in this case may be calculated as, for example, about 80%.

When the single content 5 has the form of a tablet in which a length X is the same as or similar to a width Y and a height Z as in FIG. 11 or has any shape that is not flat, a space of the passing passage part 139 may be formed as a space having a horizontal width that exceeds a width of a single content and is less than or equal to two times the width of the single content when a fixed amount of contents 5 is a single content 5.

When the single content is passed as the fixed amount, the passing space of the passing passage part 139 may have a passing space limit in a range in which a length of the shortest width in the horizontal direction exceeds a cross-sectional axial length of the content 5 and is less than or equal to two times the cross-sectional axial length. This prevents the contents 5 beyond a single content from simultaneously passing through the passing passage part 139. When a plurality of contents 5 are simultaneously passed, the passing space limit may be adjusted to be larger than two times the cross-sectional axial length.

In FIG. 12, when the fixed amount of contents 5 is a single content and the single content is passed as the fixed amount through a space whose vertical height exceeds one times the maximal length of a height or a width of the single content 5 and is less than two times the maximal length, the passing space of the passing passage part 139 may have a passing space limit in which a length of the shortest width in the vertical direction is less than or equal to two times the cross-sectional axial length of the content 5. This prevents the contents 5 beyond a single content from simultaneously passing through the passing passage part 139.

FIG. 13 illustrates a process in which the passing movement part 140 is being returned to the state before tilting or a case in which the passing movement part 140 is being stood upright. When the housing 110 is moved clockwise and returned to its initial state after the fixed amount of the contents 5 is passed to the outside, the content 5 does not come into contact with the blocking member 127 as the content 6 that was in contact with the blocking member 127 and pressing the blocking member 127 moves downward due to gravity (indicated by "C"), and the passing movement part 140 rotates clockwise, which is rightward, due to the weight leaning rightward with respect to the movement member 125, rotates to a point resisted by the stopper 129, and is returned to its initial state. When the blocking member 127 is returned to the state of being open, when the passing movement part 140 is tilted leftward again, a passing standby state in which the passing movement part 140 does not rotate before the content 5 initially comes into contact with the passing movement part 140 is reached.

Then, when the housing 110 is tilted toward the opening 122, as illustrated in FIG. 5, a preparation step is satisfied such that it is possible to lead the fixed amount of contents 5.

In FIG. 14, the light emitting part 410 is installed in the vicinity of the passing movement part 140 in the passing operation part 120 or the container main body 110 and emits light in an axial direction of the movement member 125 disposed in the passing movement part 140 that guides discharge of the contents 5. The quantity or data of light emitted by the light emitting part 410 that is reflected from the contents 5 varies according to whether the contents 5 are discharged through the passing movement part 140.

Here, an installation position of the light emitting part 410 is not particularly limited to the above, and the light emitting part 410 may be installed at various positions at which discharge of the contents 5 can be sensed.

Particularly, the light emitting part 410 may be installed in a support part 440 protruding from the movement guide part 180. In this case, a penetrating part 450 may be formed in the passing operation part 120 so that light emitted from the light emitting part 410 can be emitted to the passing movement part 140.

The light receiving part 420 is installed at the movement guide part 180 at the other side of the light emitting part 410 and receives light emitted from the light emitting part 410.

The light receiving part 420 is not limited to being installed at the movement guide part 180 as described above and may be installed at various positions at which discharge of the contents 5 can be sensed.

In this case, the penetrating part 450 is formed in the passing operation part 120 so that light emitted from the light emitting part 410 can be emitted to the passing movement part 140. Thus, light emitted through the light emitting part 410 may be received by the light receiving part 420 through the penetrating part 450.

Therefore, light emitted from the light emitting part 410 may be reflected by the contents 5 or received by the light receiving part 420 according to whether the contents 5 block the penetrating part 450 or are discharged through the penetrating part 450.

A signal medium transmitted from a transmitting part, which is the light emitting part 410 of the present embodiment, and received by a receiving part, which is the light receiving part 420, is not limited to light of the present embodiment. The signal medium may include magnetism, radio waves, temperature, pressure, vibration, gas, and the like, and a sensor part may include a transmitting part configured to transmit the signal medium and a receiving part configured to receive the signal medium, or a sensor part may include only a receiving part, which is configured to receive a signal generated from the signal medium, without a transmitting part.

The passing operation part 120 serves to lead movement of the contents 5 by a fixed amount or a demand amount. Here, "fixed amount" refers to the same number or amount or the amount or number varying within an error range. "Demand amount" is an amount (number) required by a user and belongs to the category of "fixed amount."

Figure 15:
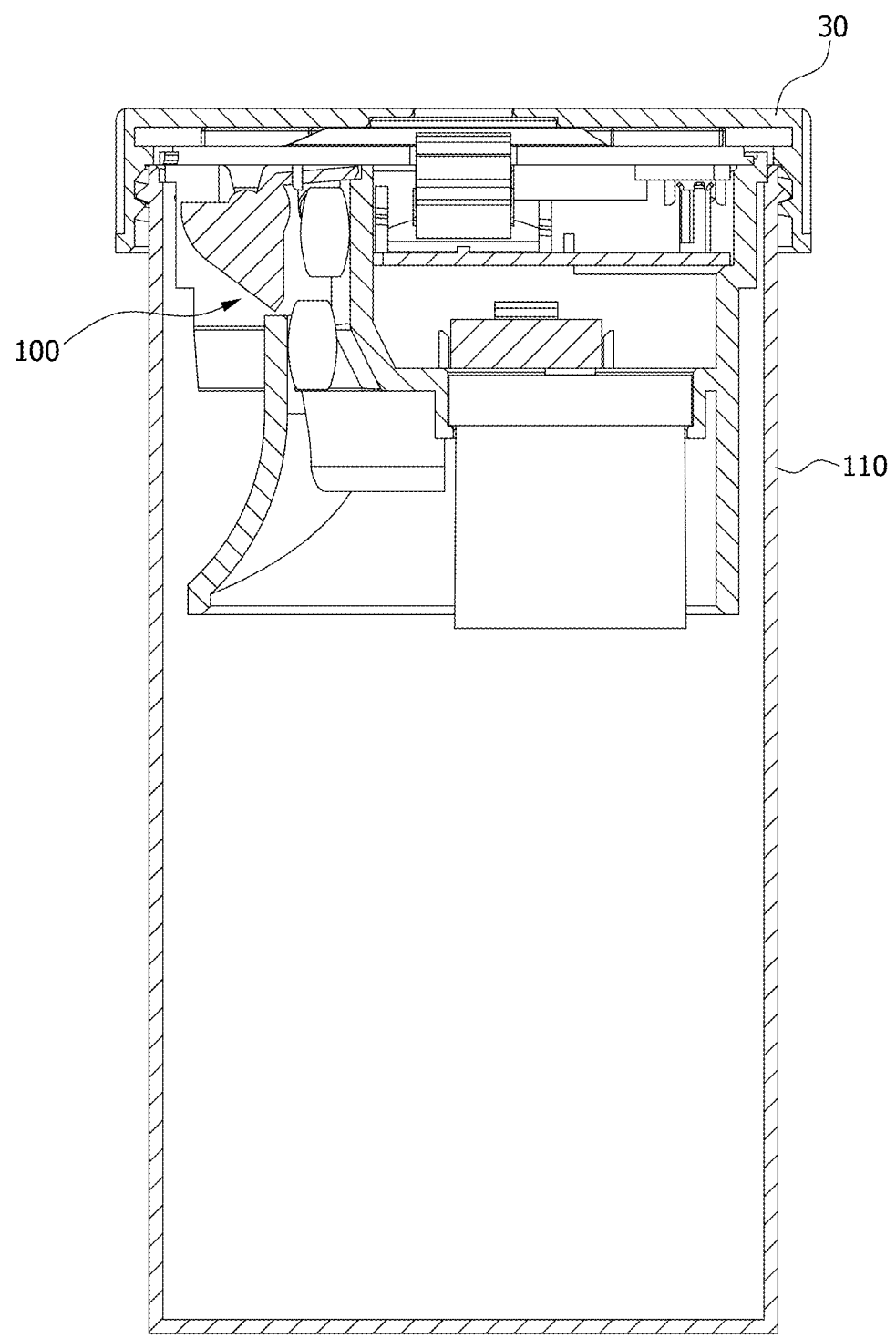
FIG. 15 is a cross-sectional view of a contents conveying apparatus including a passing device according to a second embodiment of the present invention.

FIG. 15 is a cross-sectional view of a contents conveying apparatus including a passing device according to a second embodiment of the present invention.

Referring to FIG. 15, in the contents conveying apparatus including the passing device, at the upper portion, i.e., the inlet, of the housing 110, the passing device 100 and a sensor part, which will be described below, may be inserted into the upper portion of the housing 110 while being detachably installed therein.

In this case, the passing device 100 may be installed to be seated on the upper portion of the housing 110, and the cover 30 may be coupled to the housing 110 through screw threads.

That is, because the passing device 100 and the sensor part are detachably installed in the housing 110 and the cover 30 is rotatably coupled to the housing 110 through the screw threads, the user may easily couple the passing device 100 and the sensor part.

In this case, heights of upper end portions of the passing device 100 and the sensor part may be similar to the height of the upper end portion of the housing 110, and the user may easily detach the corresponding passing device 100 and sensor part while holding a handle (not illustrated) disposed at the passing device 100.

Figure 16:
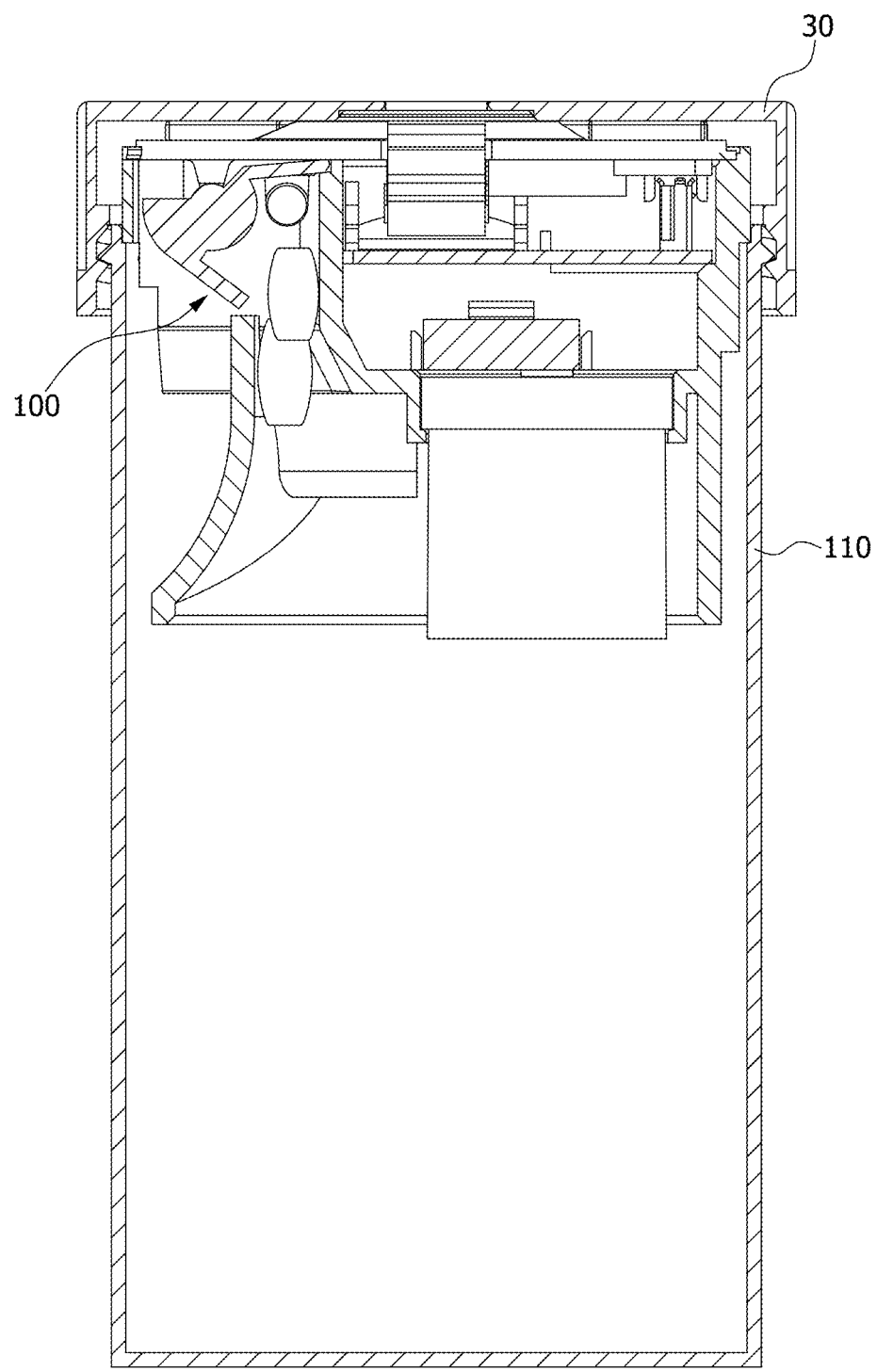
FIG. 16 is a cross-sectional view of a contents conveying apparatus including a passing device according to a third embodiment of the present invention.

FIG. 16 is a cross-sectional view of a contents conveying apparatus including a passing device according to a third embodiment of the present invention.

Referring to FIG. 16, in the contents conveying apparatus including the passing device, at the upper portion, i.e., the inlet, of the housing 110, the passing device 100 and a sensor part, which will be described below, may be inserted into the upper portion of the housing 110 while being detachably installed therein.

In this case, the passing device 100 may be installed to be seated on the upper portion of the housing 110, and the cover 30 may be coupled through screw threads.

That is, because the passing device 100 and the sensor part are detachably installed in the housing 110 and the cover 30 is rotatably coupled to the housing 110 through the screw threads, the user may easily couple the passing device 100 and the sensor part.

In this case, heights of upper end portions of the passing device 100 and the sensor part are relatively higher than the height of the upper end portion of the housing 110. Thus, the user may easily detach the passing device 100 and the sensor part while holding the corresponding passing device 100.

Figure 17:
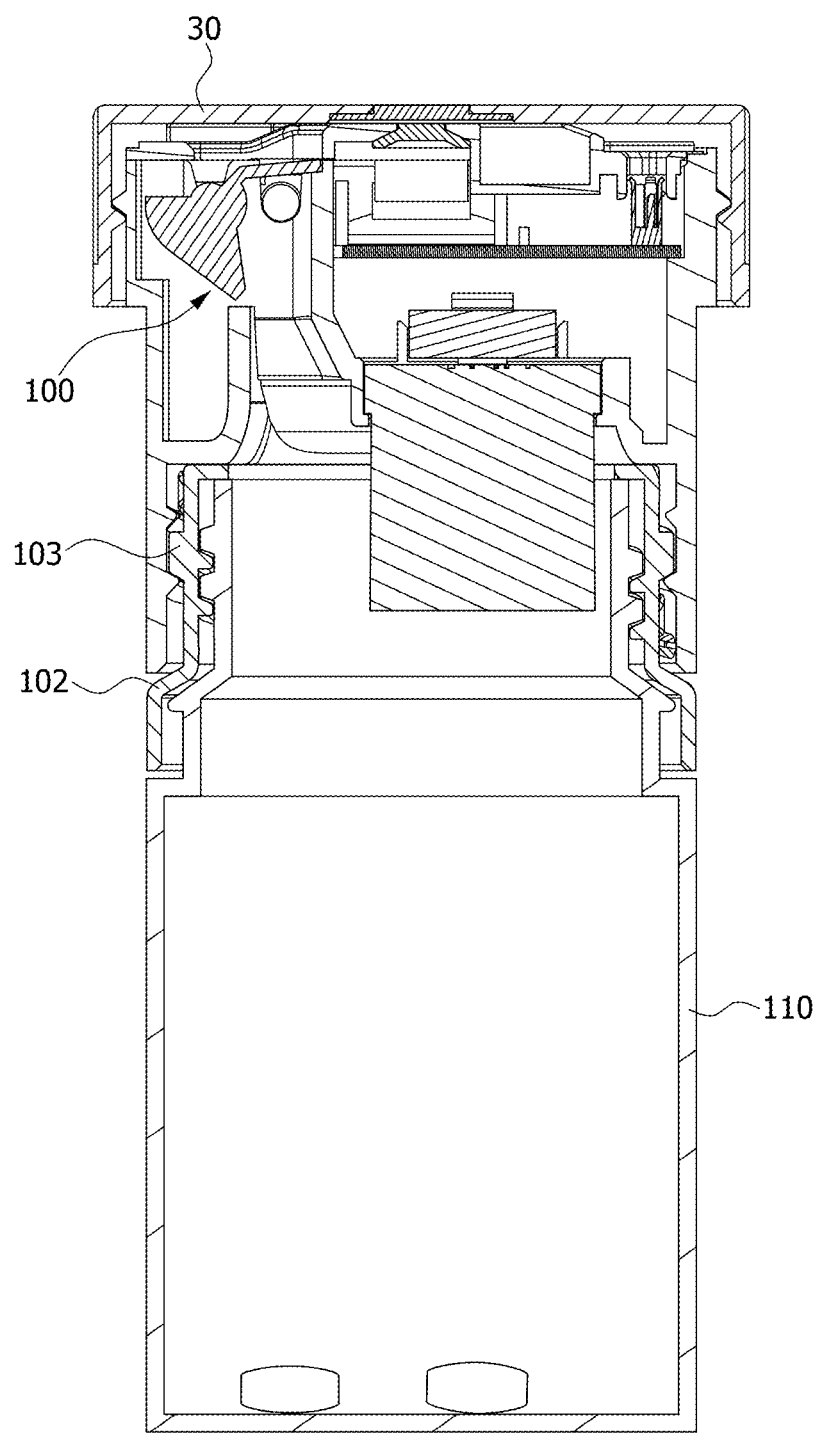
FIG. 17 is a cross-sectional view of a contents conveying apparatus including a passing device according to a fourth embodiment of the present invention.

FIG. 17 is a cross-sectional view of a contents conveying apparatus including a passing device according to a fourth embodiment of the present invention.

Referring to FIG. 17, in the contents conveying apparatus including the passing device, unlike in the second embodiment and the third embodiment described above, the passing device 100 and a sensor part, which will be described below, are coupled to the upper portion of the housing 110 through screw threads instead of being inserted into the upper portion of the housing 110 at the upper portion, i.e., the inlet, of the housing 110, and the cover 30 is coupled through screw threads formed at an outer portion of the passing device 100.

That is, because the passing device 100 and the sensor part are separately disposed and screw-coupled to the housing 110 and the cover 30 is coupled through the screw threads formed at the outer portion of the passing device 100, the housing 110, the passing device 100, and the cover 30 are detachable independently of each other.

In this case, the passing device 100 may further include a sealing part 102 configured to seal the housing 110. In this case, the sealing part 102 may be coupled to the passing device 100 and the cover 30 through screw threads, and a sealing protrusion part 103 may be formed to protrude to an outer side of the sealing part 102 and come in surface contact with an inner side of the passing device 100 so that the sealing performance is further improved.

In this way, because the passing device 100 may be coupled to the housing 110 in the form of being added thereon, the passing device 103 and the cover 30 may be manufactured according to the size and shape of the housing 110, and, in this case, the passing device 100 and the cover 30 may be easily coupled to the housing 110 of various shapes and sizes.

Figure 18:
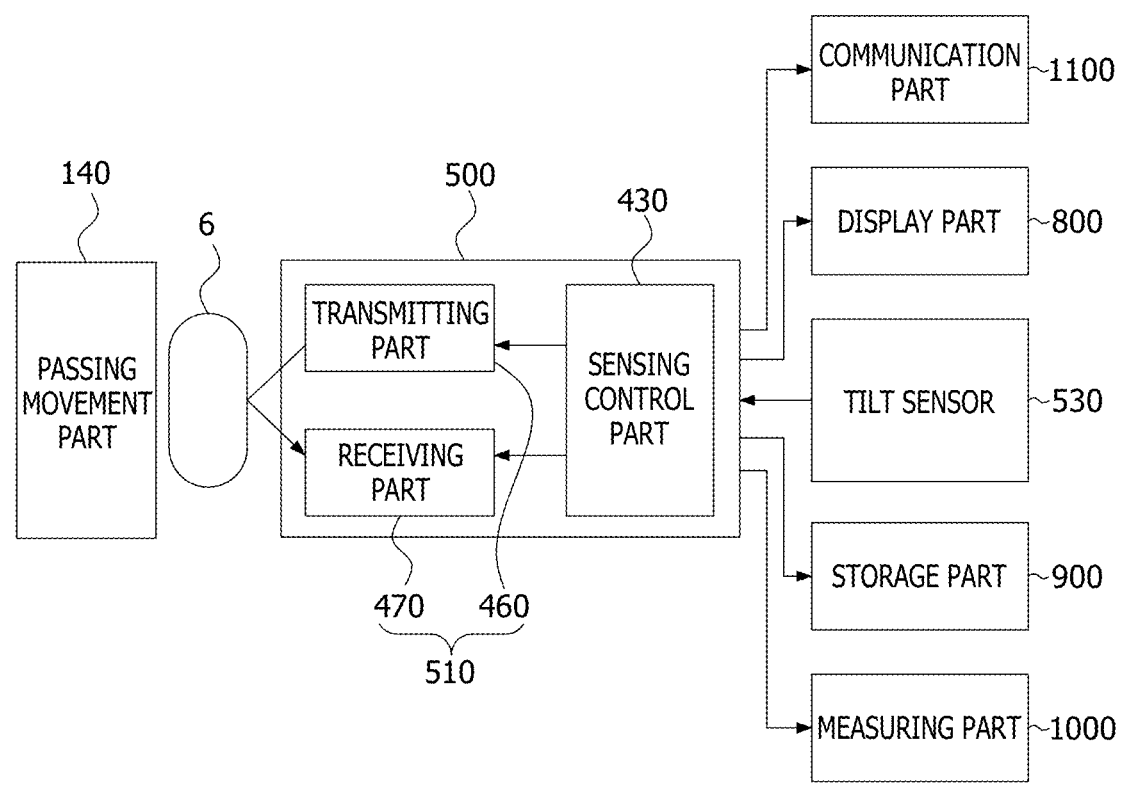
FIG. 18 is a block diagram of a passing device configured to sense movement of contents according to a fifth embodiment of the present invention.
Figure 19:
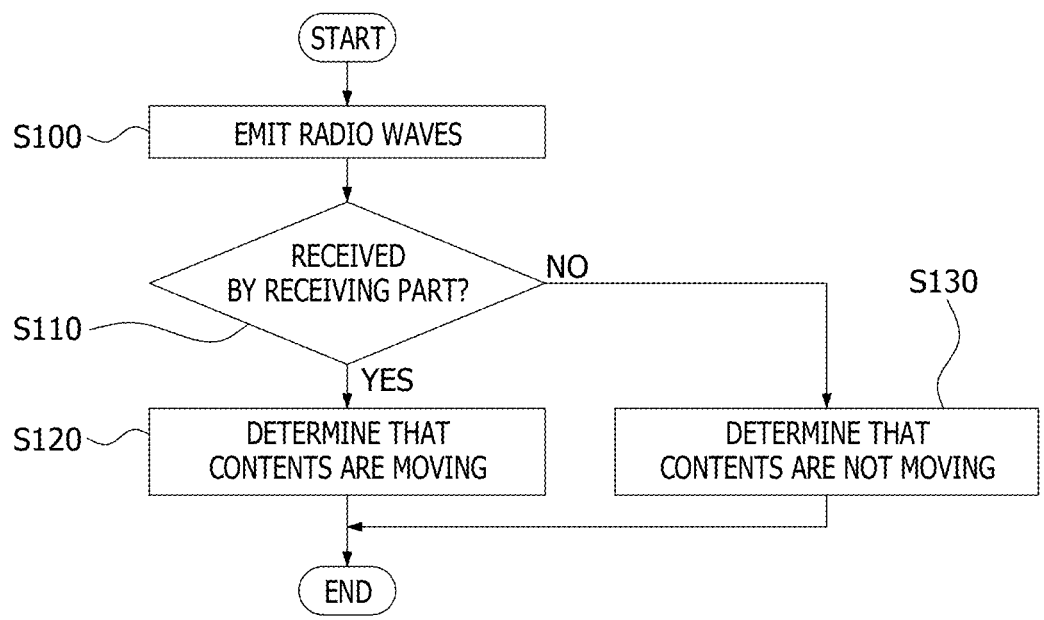
FIG. 19 is a flowchart illustrating an operational process of the passing device according to the fifth embodiment of the present invention.

FIG. 18 is a block diagram of a passing device configured to sense movement of contents according to a fifth embodiment of the present invention, and FIG. 19 is a flowchart illustrating an operational process of the passing device according to the fifth embodiment of the present invention.

Referring to FIG. 18, the passing device that senses discharge of contents 5 according to the fifth embodiment of the present invention includes a sensing part 500, a display part 800, a storage part 900, a measuring part 1000, and a communication part 1100. The sensing part may also be referred to as "sensor module" herein.

The storage part 900 stores information on contents detected by the sensor module 500.

The measuring part 1000 calculates a cumulative discharge amount of contents by period on the basis of the information stored in the storage part 900.

The display part 800 outputs the information on the contents detected by the sensor module 500, the information stored in the storage part 900, or the information measured by the measuring part 1000.

The communication part 1100 transmits the information on the contents detected by the sensor module 500, the information stored in the storage part 900, or the information measured by the measuring part 1000 to an external device through wired or wireless communication.

The sensor module 500 is disposed in a passing operation part and senses contents discharged due to free rotation of one end of a passing movement part.

The sensor module or sensing part 500 includes a sensor part 510, a tilt sensor 530, and a sensing control part 430. The sensor part 510 is configured to sense whether contents 5 are discharged and includes a transmitting part 460 and a receiving part 470.

The tilt sensor 530 senses a slope of the housing 1.

The transmitting part 460 is installed in a passing operation part 120 and emits radio waves toward a passing movement part 140 which guides discharge of contents 5. The radio waves emitted by the transmitting part 460 may be reflected by the passing movement part 140 or may be reflected by or reacted with the contents 5 discharged by the passing movement part 140.

Here, the transmitting part 460 may be installed at the movement guide part 180 of the passing operation part 120 as described above. However, the technical scope of the present invention is not limited thereto, and the transmitting part 460 may be installed at various position at which discharge of the contents 5 can be sensed.

Further, the transmitting part 460 may be installed at the support part 440 formed to protrude from the movement guide part 180.

In this case, the penetrating part 450 is formed at the movement guide part 180 so that light emitted from the transmitting part 460 can be emitted to the passing movement part 140. Thus, the radio waves emitted through the transmitting part 460 may be reflected by the passing movement part 140 or the contents 5 through the penetrating part 450.

The receiving part 470 is installed at the movement guide part 180 and receives the radio waves reflected by the passing movement part 140 or the contents 5.

The receiving part 470 may be installed parallel to the transmitting part 460 at a position adjacent to the transmitting part 460. The receiving part 470 is not limited to being installed at the movement guide part 180 of the passing operation part 120 as described above and may be installed at various positions at which discharge of the contents 5 can be sensed.

Particularly, the receiving part 470 may be installed at the support part 440 formed to protrude from the movement guide part 180.

Therefore, the radio waves emitted from the transmitting part 460 are reflected by the passing movement part 140 or the contents 5 through the penetrating part 450, and the radio waves reflected by the passing movement part 140 or the contents 5 are received again by the receiving part 470 through the penetrating part 450.

The sensing control part 430 controls the light emitting part 410 at every predetermined period to emit light and senses the contents 5 discharged through the passing movement part 140 on the basis of the radio waves received by the receiving part 470.

Because the sensing control part 430 controls the transmitting part 460 at every predetermined period to emit radio waves, the sensing control part 430 may immediately detect discharge of the contents 5 even when a user discharges the contents 5 at irregular intervals. The predetermined period may be adjusted. The discharge of the contents 5 may be detected more thoroughly as the predetermined period is shortened.

The contents 5 are not discharged by the passing operation part 120 in a state in which the housing 110 is placed so that the contents 5 are not discharged.

Conversely, when the housing 110 is tilted and the contents 5 are discharged, because the contents 5 are discharged through the passing operation part 120, the radio waves emitted by the transmitting part 460 are reflected by the contents 5 and received by the receiving part 470.

When the radio waves are received by the receiving part 470, the sensing control part 430 uses the radio waves received by the receiving part 470 and senses the contents 5.

Also, when the radio waves reflected by the contents 5 are received by the receiving part 470 and then not received by the receiving part 470 again, the sensing control part 430 may determine that the contents 5 have been discharged by the passing operation part 120.

Further, the sensing control part 430 may determine that the contents 5 have been discharged when the radio waves are not received by the receiving part 470 in a state in which a slope of the housing 1 sensed by the tilt sensor 530 is within a predetermined slope and may determine that the contents 5 have not been discharged when the radio waves are not received by the receiving part 470 in a state in which the slope of the housing 1 sensed by the tilt sensor 530 is beyond the predetermined slope. In this way, a case in which the contents 5 are erroneously determined as having been discharged even when the contents 5 actually have not been discharged due to being jammed in the process of discharging the contents 5 may be prevented.

Here, the predetermined slope is a slope of the housing 1 at which the contents 5 can be discharged.

Next, an operational process of the passing device according to the fifth embodiment of the present invention will be described with reference to FIG. 19.

Referring to FIG. 19, first, the sensing control part 430 controls the transmitting part 460 and emits radio waves (S100).

The radio waves emitted by the transmitting part 460 may be reflected by the contents 5 according to whether the contents 5 are discharged by the passing operation part 120.

Thus, the sensing control part 430 determines whether the radio waves emitted from the transmitting part 460 are received by the receiving part 470 (S110).

When, as a result of the determination in Operation S110, the radio waves emitted from the transmitting part 460 are determined as having been received by the receiving part 470, and the contents 5 are sensed, the sensing control part 430 determines that the contents 5 are being discharged through the passing operation part 120 (S120).

Conversely, when the radio waves emitted from the transmitting part 460 are reflected by the contents 5 and not received by the receiving part 470, the sensing control part 430 determines that the contents 5 are not being discharged through the passing operation part 120 (S130).

Meanwhile, in the above process, when the radio waves are received by the receiving part 470 and then not received by the receiving part 470 again, the sensing control part 430 may determine that the contents 5 have been discharged by the passing operation part 120.

Further, the sensing control part 430 may determine that the contents 5 have been discharged when the radio waves are not received by the receiving part 470 in the state in which the slope of the housing 1 sensed by the tilt sensor 530 is within the predetermined slope and may determine that the contents 5 have not been discharged when the radio waves are not received by the receiving part 470 in a state in which the slope of the housing 1 sensed by the tilt sensor 530 is beyond the predetermined slope.

Figure 20:
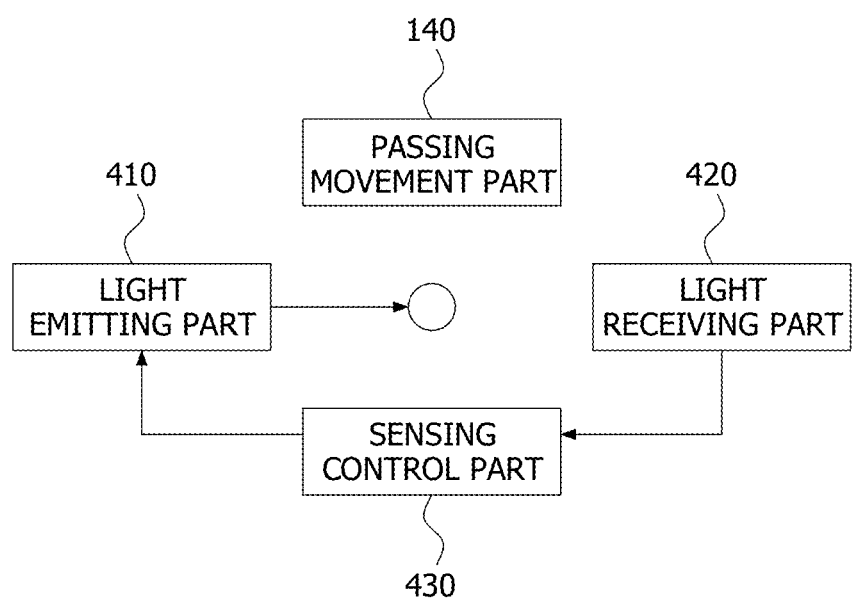
FIG. 20 is a block diagram of a passing device configured to sense movement of contents according to a sixth embodiment of the present invention.

FIG. 20 is a block diagram of a passing device configured to sense discharge of contents according to a sixth embodiment of the present invention.

Referring to FIG. 20, the passing device configured to sense discharge of contents 5 according to the sixth embodiment of the present invention includes a sensor module 500.

The sixth embodiment of the present invention may be applied to the above-described embodiment illustrated in FIGS. 1 to 12.

The sensor module 500 includes a sensor part 510, a tilt sensor 530, and a sensing control part 430. The sensor part 510 is configured to sense whether contents 5 are discharged and includes a light emitting part 410 and a light receiving part 420.

The tilt sensor 530 senses a slope of the housing 1.

The light emitting part 410 is installed at the movement guide part 180 of the passing operation part 120 and emits light in the axial direction of the movement member 125 disposed in the passing movement part 140 that guides discharge of the contents 5. The light emitted by the light emitting part 410 may be reflected by the contents 5 according to whether the contents 5 are discharged through the passing movement part 140. That is, the light emitted by the light emitting part 410 may be reflected by the contents 5 and not received by the light receiving part 420 when the contents 5 are discharged through the passing movement part 140 and may be received by the light receiving part 420 formed at the other side when the contents 5 are not discharged through the passing movement part 140.

Here, an installation position of the light emitting part 410 is not particularly limited to the above, and the light emitting part 410 may be installed at various positions at which discharge of the contents 5 can be sensed.

Particularly, the light emitting part 410 may be installed at the support part 440 formed to protrude from the movement guide part 180.

In this case, the penetrating part 450 is formed in the passing operation part 120 so that the light emitted from the light emitting part 410 may be emitted to the passing movement part 140. Thus, the light emitted through the light emitting part 410 is reflected by the contents 5 or received by the light receiving part 420 at the other side through the penetrating part 450.

The light receiving part 420 is installed at the movement guide part 180 at the other side of the light emitting part 410 and receives light emitted from the light emitting part 410.

The light receiving part 420 is not limited to being installed at the movement guide part 180 as described above and may be installed at various positions at which discharge of the contents 5 can be sensed.

In this case, the penetrating part 450 is formed in the passing operation part 120 so that the light emitted from the light emitting part 410 may be emitted to the passing movement part 140. Thus, the light emitted through the light emitting part 410 may be received by the light receiving part 420 through the penetrating part 450.

Therefore, light emitted from the light emitting part 410 may be reflected by the contents 5 or received by the light receiving part 420 according to whether the contents 5 are discharged through the penetrating part 450.

The sensing control part 430 controls the light emitting part 410 at every predetermined period to emit light and senses the contents 5 discharged through the passing operation part 120 according to whether the light emitted from the light emitting part 410 is received by the light receiving part 420.

Because the sensing control part 430 controls the light emitting part 410 at every predetermined period to emit light, the sensing control part 430 may immediately detect discharge of the contents 5 even when a user discharges the contents 5 at irregular intervals. The predetermined period may be adjusted. The discharge of the contents 5 may be detected more thoroughly as the predetermined period is shortened.

Here, the contents 5 are not discharged by the passing operation part 120 in the state in which the housing 110 is placed so that the contents 5 are not discharged.

Conversely, when the housing 110 is tilted and the contents 5 are discharged, because the contents 5 are discharged through the passing operation part 120, the light emitted by the light emitting part 410 is partially or entirely blocked by the contents 5, and the quantity of light received by the light receiving part 420 is smaller as compared to when the contents 5 do not pass.

Thus, the sensing control part 430 may determine that the contents 5 are being moved by the passing operation part 120 when light is not received by the light receiving part 420 or the quantity of light received by the light receiving part 420 is small and may determine that the contents 5 are not being discharged by the passing operation part 120 when light is received by the light receiving part 420.

Also, when, after a state in which light is not received by the light receiving part 420 is reached, light is received by the light receiving part 420 again, the sensing control part 430 may determine that the contents 5 have been discharged by the passing operation part 120.

Further, the sensing control part 430 may determine that the contents 5 have been discharged when light is not received by the light receiving part 420 in a state in which a slope of the housing 1 sensed by the tilt sensor 530 is within a predetermined slope and may determine that the contents 5 have not been discharged when light is not received by the light receiving part 420 in a state in which the slope of the housing 1 sensed by the tilt sensor 530 is beyond the predetermined slope. In this way, a case in which the contents 5 are erroneously determined as having been discharged even when the contents 5 actually have not been discharged due to being jammed in the process of discharging the contents 5 may be prevented.

Here, the predetermined slope is a slope of the housing 1 at which the contents 5 can be discharged.

Also, when, after a state in which light is not received by the light receiving part 420 is reached, light is received by the light receiving part 420 again, the sensing control part 430 may determine that the contents 5 have been discharged by the passing operation part 120

Further, the sensing control part 430 may determine that the contents 5 have been discharged when light is not received by the light receiving part 420 in a state in which a slope of the housing 1 sensed by the tilt sensor 530 is within a predetermined slope and may determine that the contents 5 have not been discharged when light is not received by the light receiving part 420 in a state in which the slope of the housing 1 sensed by the tilt sensor 530 is beyond the predetermined slope. In this way, a case in which the contents 5 are erroneously determined as having been discharged when the contents 5 actually have not been discharged due to being jammed in the process of discharging the contents 5 may be prevented.

Here, the predetermined slope is a slope of the housing 1 at which the contents 5 can be discharged.

Figure 21:
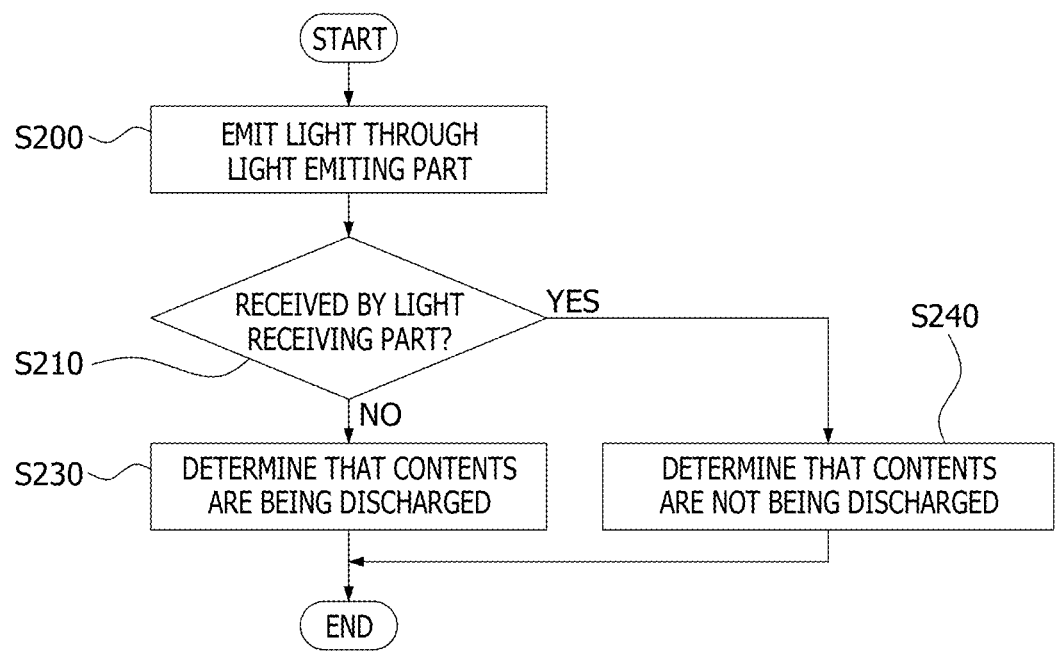
FIG. 21 is a flowchart illustrating an operational process of the passing device according to the sixth embodiment of the present invention.

Next, an operational process of the passing device according to the sixth embodiment of the present invention will be described with reference to FIG. 21.

First, the sensing control part 430 controls the light emitting part 410 and emits light (S200).

The light emitted by the light emitting part 410 may be blocked by the contents 5 according to whether the contents 5 are discharged by the passing operation part 120.

Thus, the sensing control part 430 determines whether the light emitted from the light emitting part 410 is received by the light receiving part 420 (S210).

When, as a result of the determination in Operation S210, the light emitted from the light emitting part 410 is determined as not having been received by the light receiving part 420, the sensing control part 430 determines that the contents 5 are being discharged through the passing operation part 120 (S220).

Conversely, when the light is received by the light receiving part 420, the sensing control part 430 determines that the contents 5 are not being discharged through the passing operation part 120 (S230).

Also, when, after a state in which light is not received by the light receiving part 420 is reached, light is received by the light receiving part 420 again, the sensing control part 430 may determine that the contents 5 have been discharged by the passing operation part 120

Further, the sensing control part 430 may determine that the contents 5 have been discharged when light is not received by the light receiving part 420 in a state in which a slope of the housing 1 sensed by the tilt sensor 530 is within a predetermined slope and may determine that the contents 5 have not been discharged when light is not received by the light receiving part 420 in a state in which the slope of the housing 1 sensed by the tilt sensor 530 is beyond the predetermined slope.

Meanwhile, in the above process, when, after the state in which light is not received by the light receiving part 420 is reached, light is received by the light receiving part 420 again, the sensing control part 430 may determine that the contents 5 have been discharged by the passing operation part 120.

Further, the sensing control part 430 may determine that the contents 5 have been discharged when light is not received by the light receiving part 420 in the state in which the slope of the housing 1 sensed by the tilt sensor 530 is within the predetermined slope and may determine that the contents 5 have not been discharged when light is not received by the light receiving part 420 in a state in which the slope of the housing 1 sensed by the tilt sensor 530 is beyond the predetermined slope.

Figure 22:
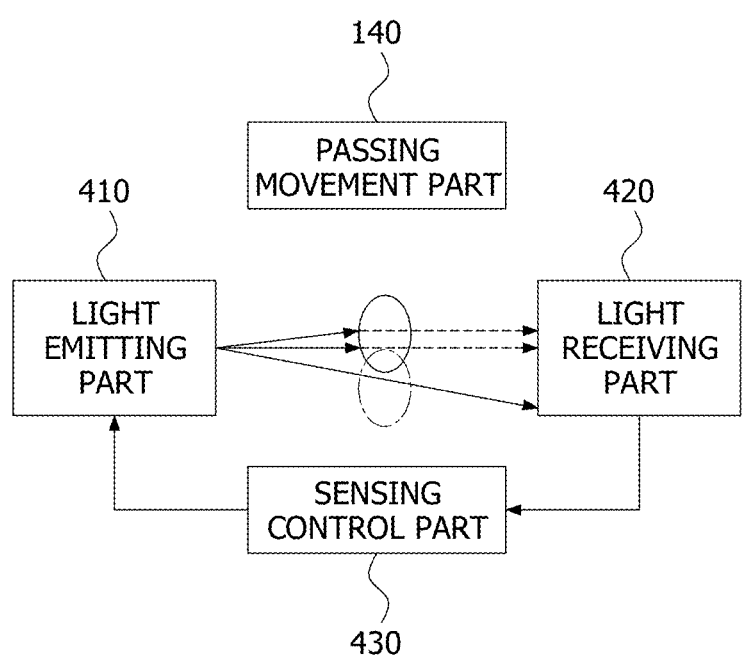
FIG. 22 is a block diagram of a passing device configured to sense movement of contents according to a seventh embodiment of the present invention.
Figure 23:
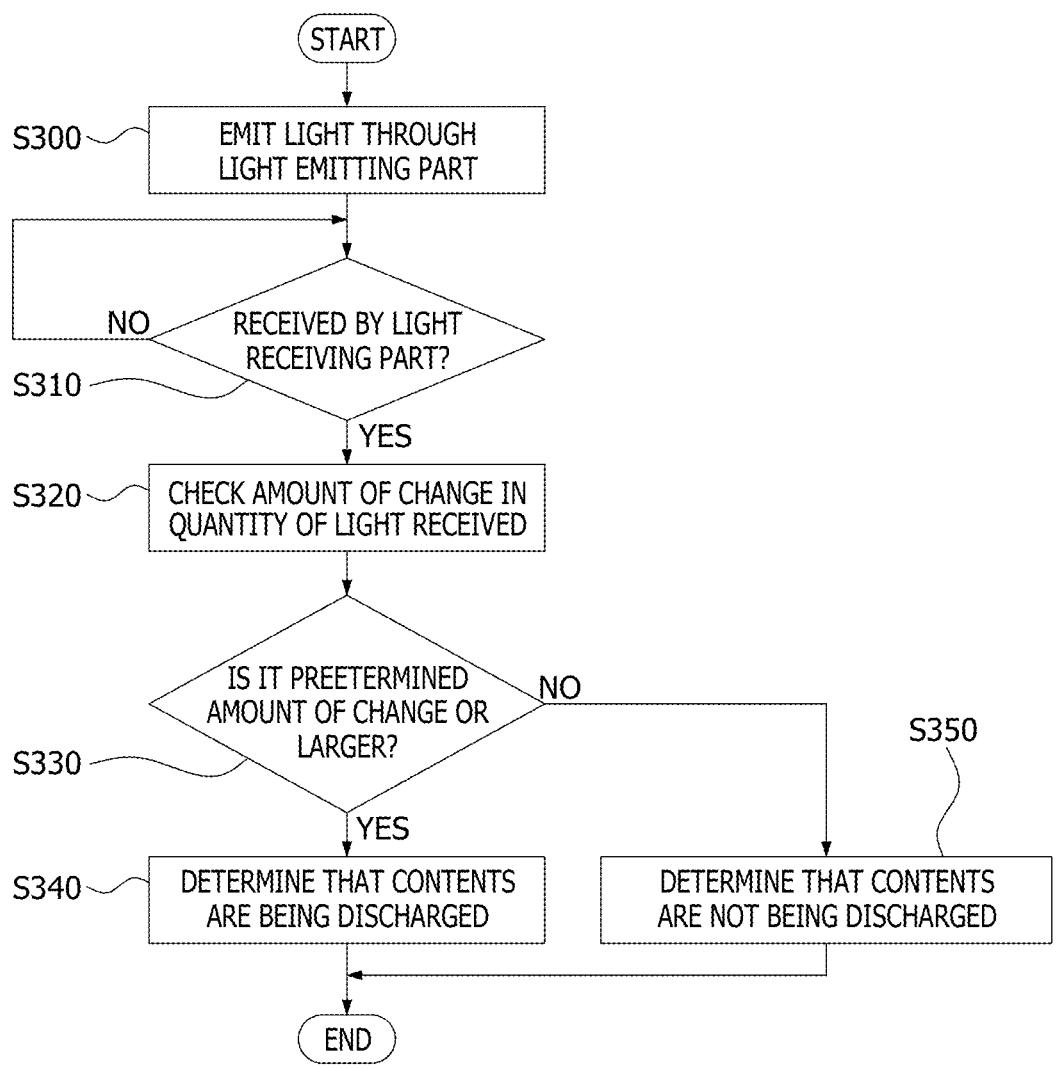
FIG. 23 is a flowchart illustrating an operational process of the passing device according to the seventh embodiment of the present invention.

FIG. 22 is a block diagram of a passing device configured to sense discharge of contents according to a seventh embodiment of the present invention, and FIG. 23 is a flowchart illustrating an operational process of the passing device according to the seventh embodiment of the present invention.

Referring to FIG. 22, the passing device configured to sense discharge of contents 5 according to the seventh embodiment of the present invention includes a sensor module 500.

The seventh embodiment of the present invention may be applied to the embodiment illustrated in FIGS. 4 and 5.

The sensor module 500 includes a sensor part 510, a tilt sensor 530, and a sensing control part 430. The sensor part 510 is configured to sense whether contents 5 are discharged and includes a light emitting part 410 and a light receiving part 420.

The tilt sensor 530 senses a slope of the housing 1.

Because an installation structure of the light emitting part 410 and the light receiving part 420 is the same as that according to the third embodiment described above, detailed description thereof will be omitted.

The sensing control part 430 controls the light emitting part 410 at every predetermined period to emit light and senses the contents 5 discharged through the passing operation part 120 according to an amount of change in the quantity of light received by the light receiving part 420. Because the sensing control part 430 controls the light emitting part 410 at every predetermined period to emit light, the sensing control part 430 may immediately detect discharge of the contents 5 even when a user discharges the contents 5 at irregular intervals. The predetermined period may be adjusted. The discharge of the contents 5 may be detected more thoroughly as the predetermined period is shortened.

Meanwhile, the contents 5 are not discharged by the passing operation part 120 in the state in which the housing 110 is placed so that the contents 5 are not discharged.

Conversely, when the housing 110 is tilted and the contents 5 are discharged, because the contents 5 are discharged through the passing operation part 120 and, in this case, the light emitted by the light emitting part 410 is partially reflected by the contents 5, the quantity of light received by the light receiving part 420 changes.

Thus, the sensing control part 430 determines whether the contents 5 are discharged through the passing operation part 120 according to the amount of change in the quantity of light received by the light receiving part 420.

That is, the sensing control part 430 compares the amount of change in the quantity of light received by the light receiving part 420 with a predetermined amount of change and, according to a result of the comparison, senses whether the contents 5 are discharged through the passing operation part 120. The sensing control part 430 determines that the contents 5 are being discharged by the passing operation part 120 when the amount of change in the quantity of light is the predetermined amount of change or larger and determines that the contents 5 are not being discharged by the passing operation part 120 when the amount of change in the quantity of light is less than the predetermined amount of change.

Here, the predetermined amount of change is an amount of change in the quantity of light from which the contents 5 may be determined as being discharged by the passing operation part 120. That is, when the contents 5 are not discharged by the passing operation part 120, because light emitted from the light emitting part 410 is not reflected by the contents 5, the amount of change in the quantity of light is very small. Conversely, when the contents 5 are discharged by the passing operation part 120, light emitted from the light emitting part 410 is partially or entirely reflected by the contents 5. As a result, the quantity of light received by the light receiving part 420 changes according to discharge of the contents 5. Thus, by presetting the amount of change in the quantity of light from which the contents 5 may be determined as being discharged by the passing operation part 120 as the predetermined amount of change, whether the contents 5 have been discharged through the passing operation part 120 may be accurately determined.

Also, when, after a state in which the amount of change in the quantity of light received by the light receiving part 420 is the predetermined amount of change or larger is reached, the amount of change in the quantity of light returns to a state before changing to be the predetermined amount of change or larger, the sensing control part 430 may determine that the contents 5 have been discharged by the passing operation part 120.

Further, the sensing control part 430 may determine that the contents 5 have been discharged when the quantity of light reaches a state in which the amount of change in the quantity of light is the predetermined amount of change or larger in a state in which a slope of the housing 1 sensed by the tilt sensor 530 is within a predetermined slope and may determine that the contents 5 have not been discharged when the quantity of light becomes a state in which the amount of change in the quantity of light is the predetermined amount of change or larger in a state in which the slope of the housing 1 sensed by the tilt sensor 530 is beyond the predetermined slope. In this way, a case in which the contents 5 are erroneously determined as having been discharged even when the contents 5 actually have not been discharged due to being jammed in the process of discharging the contents 5 may be prevented.

Here, the predetermined slope is a slope of the housing 1 at which the contents 5 can be discharged.

An operational process of the passing device according to the seventh embodiment of the present invention will be described in detail with reference to FIG. 23.

Referring to FIG. 23, first, the sensing control part 430 controls the light emitting part 410 and emits light (S300).

The light emitted by the light emitting part 410 may be partially or entirely blocked by the contents 5 according to whether the contents 5 are discharged through the passing operation part 120, and, as a result, the quantity of light received by the light receiving part 420 changes according to discharge of the contents 5.

Thus, the sensing control part 430 determines whether the light emitted from the light emitting part 410 is received by the light receiving part 420 (S310), and, when, as a result of the determination, the light emitted from the light emitting part 410 is determined as having been received by the light receiving part 420, the sensing control part 430 checks the quantity of light received by the light receiving part 420 (S320).

As the quantity of light received by the light receiving part 420 is checked, the sensing control part 430 compares the quantity of light with a predetermined amount of change and determines whether the quantity of light is equal to or larger than the predetermined amount of change (S330).

The sensing control part 430 determines that the contents 5 are being discharged by the passing operation part 120 when, as a result of the determination in Operation S330, the quantity of light is determined as being the predetermined amount of change or larger (S340) and determines that the contents 5 are not being discharged by the passing operation part 120 when the quantity of light is less than the predetermined amount of change (S350).

Meanwhile, in the above process, when, after a state in which the amount of change in the quantity of light received by the light receiving part 420 is the predetermined amount of change or larger is reached, the quantity of light reaches the state in which the amount of change in the quantity of light is the predetermined amount of change or larger, the sensing control part 430 may determine that the contents 5 have been discharged by the passing operation part 120.

Further, the sensing control part 430 may determine that the contents 5 have been discharged when the quantity of light reaches a state in which the amount of change in the quantity of light is the predetermined amount of change or larger in a state in which the slope of the housing 1 sensed by the tilt sensor 530 is within the predetermined slope and may determine that the contents 5 have not been discharged when the quantity of light reaches a state in which the amount of change in the quantity of light is the predetermined amount of change or larger in a state in which the slope of the housing 1 sensed by the tilt sensor 530 is beyond the predetermined slope.

Figure 24:
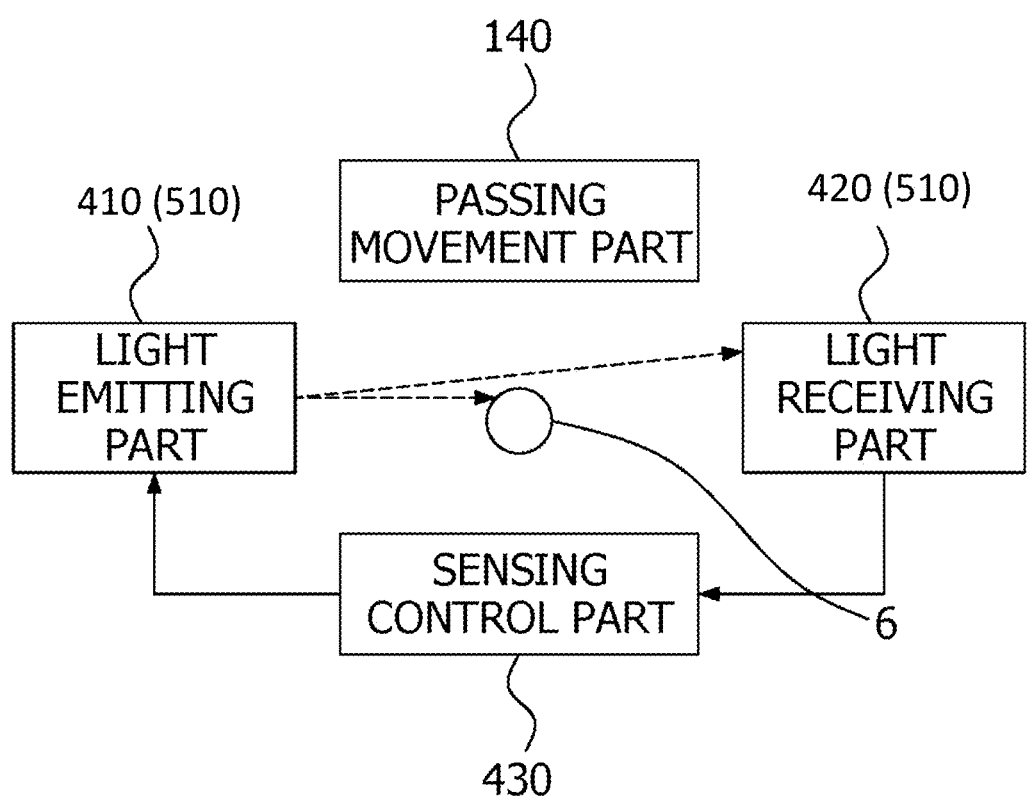
FIG. 24 is a block diagram of a passing device configured to sense movement of contents according to an eighth embodiment of the present invention.
Figure 29:
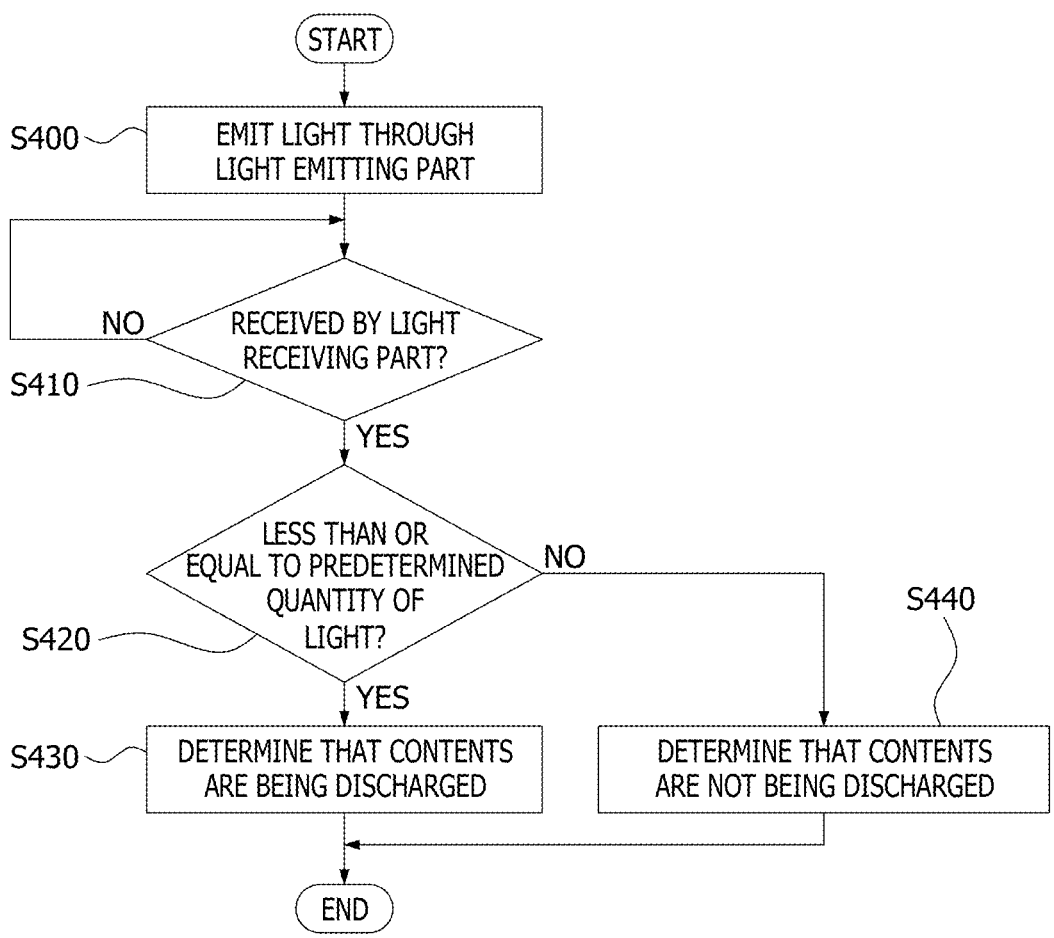
FIG. 29 is a flowchart illustrating an operational process of the passing device according to the eighth embodiment of the present invention.

FIG. 24 is a block diagram of a passing device configured to sense discharge of contents according to an eighth embodiment of the present invention, and FIG. 29 is a flowchart illustrating an operational process of the passing device according to the eighth embodiment of the present invention.

Referring to FIG. 24, the passing device configured to sense discharge of the contents 5 according to the eighth embodiment of the present invention includes a sensor module 500.

The eighth embodiment of the present invention may be applied to the embodiment illustrated in FIGS. 4 and 5.

The sensor module 500 includes a sensor part 510, a tilt sensor 530, and a sensing control part 430. The sensor part 510 is configured to sense whether contents 5 are discharged and includes a light emitting part 410 and a light receiving part 420.

The tilt sensor 530 senses a slope of the housing 1.

Because an installation structure of the light emitting part 410 and the light receiving part 420 is the same as that according to the third embodiment described above, detailed description thereof will be omitted.

The sensing control part 430 controls the light emitting part 410 at every predetermined period to emit light and senses the contents 5 discharged through the passing operation part 120 according to the quantity of light received by the light receiving part 420.

Because the sensing control part 430 controls the light emitting part 410 at every predetermined period to emit light, the sensing control part 430 may immediately detect discharge of the contents 5 even when a user discharges the contents 5 at irregular intervals. The predetermined period may be adjusted. The discharge of the contents 5 may be detected more thoroughly as the predetermined period is shortened.

Meanwhile, the contents 5 are not discharged by the passing operation part 120 in the state in which the housing is placed so that the contents 5 are not discharged.

Conversely, when the housing is tilted and the contents 5 are discharged, because the contents 5 are discharged through the passing operation part 120 and, in this case, the light emitted by the light emitting part 410 is partially reflected by the contents 5, the quantity of light received by the light receiving part 420 is reduced.

Thus, the sensing control part 430 determines whether the contents 5 are discharged through the passing operation part 120 according to quantity of light received by the light receiving part 420.

That is, the sensing control part 430 compares the quantity of light received by the light receiving part 420 with a predetermined quantity of light and, according to a result of the comparison, senses whether the contents 5 are discharged through the passing operation part 120. The sensing control part 430 determines that the contents 5 are being discharged by the passing operation part 120 when the quantity of light is less than or equal to the predetermined quantity of light and determines that the contents 5 are not being discharged by the passing operation part 120 when the quantity of light exceeds the predetermined quantity of light.

Here, the predetermined quantity of light is a quantity of light from which the contents 5 may be determined as being discharged by the passing operation part 120. That is, when the contents 5 are not discharged by the passing operation part 120, because light emitted from the light emitting part 410 is not reflected by the contents 5, the quantity of light is very large. Conversely, when the contents 5 are discharged by the passing operation part 120, light emitted from the light emitting part 410 is partially or entirely reflected by the contents 5, and, as a result, the quantity of light received by the light receiving part 420 is reduced as compared with before the contents 5 are discharged. Thus, by presetting the quantity of light from which the contents 5 may be determined as being discharged by the passing operation part 120 as the predetermined quantity of light, whether the contents 5 have been discharged through the passing operation part 120 may be accurately determined.

Also, when, after a state in which the quantity of light received by the light receiving part 420 is the predetermined quantity of light or larger is reached, the quantity of light reaches a state of being less than the predetermined quantity of light, the sensing control part 430 may determine that the contents 5 have been discharged by the passing operation part 120.

Further, the sensing control part 430 may determine that the contents 5 have been discharged when the quantity of light reaches a state of being less than the predetermined quantity of light in a state in which a slope of the housing 1 sensed by the tilt sensor 530 is within a predetermined slope and may determine that the contents 5 have not been discharged when the quantity of light reaches a state of being less than the predetermined quantity of light in a state in which the slope of the housing 1 sensed by the tilt sensor 530 is beyond the predetermined slope. In this way, a case in which the contents 5 are erroneously determined as having been discharged even when the contents 5 actually have not been discharged due to being jammed in the process of discharging the contents 5 may be prevented.

Here, the predetermined slope is a slope of the housing 1 at which the contents 5 can be discharged.

Figure 25:
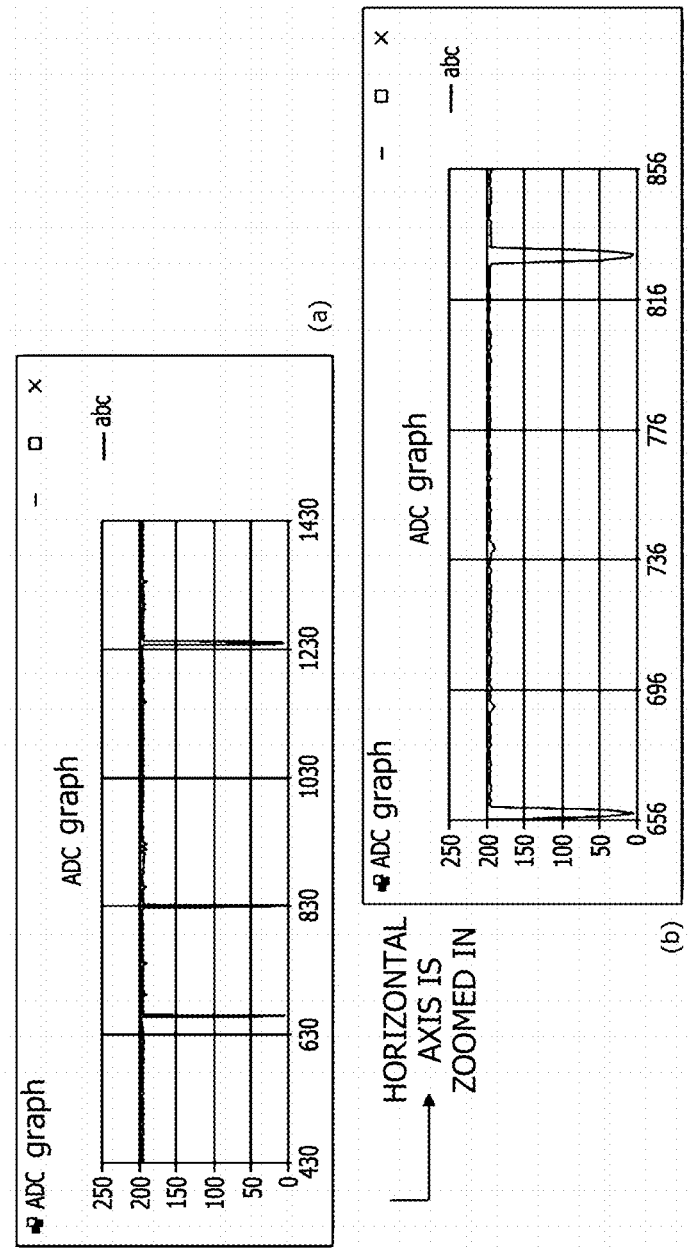
FIG. 25 is a view illustrating changes in a quantity of light when a relatively small, flat pill passes a sensor portion and is discharged to the outside due to tilting of a container according to the eighth embodiment of the present invention.
Figure 26:
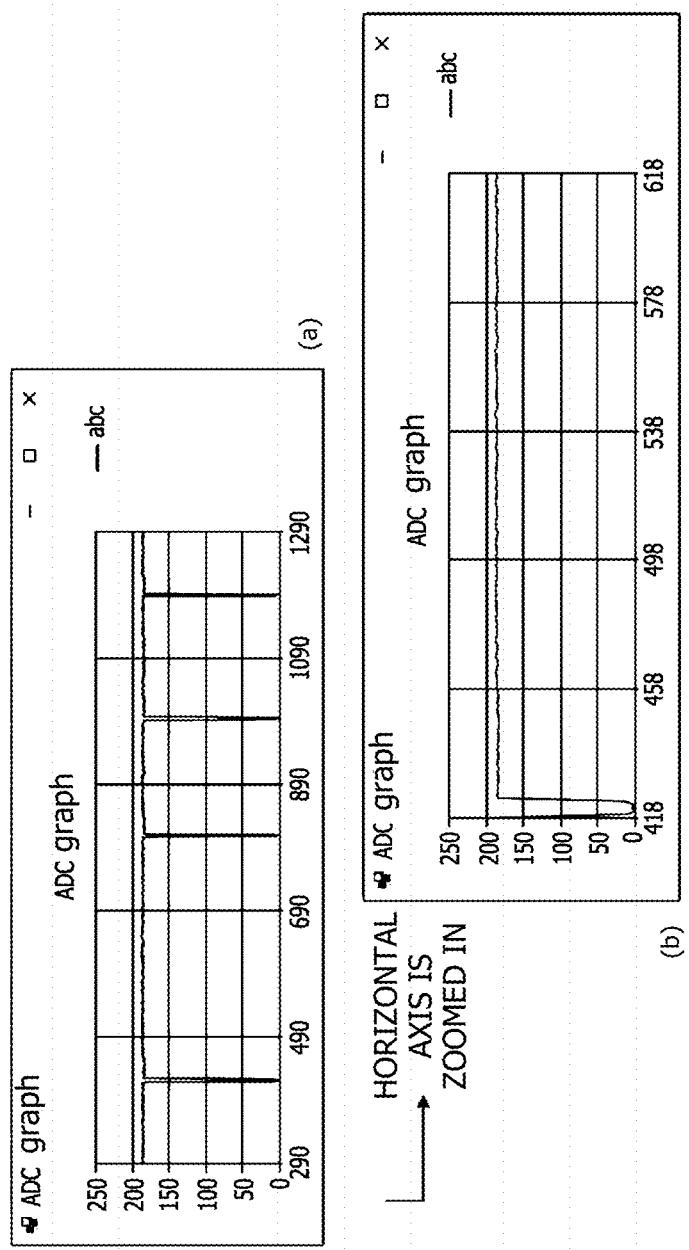
FIG. 26 is a view illustrating changes in a quantity of light when a relatively large, long pill passes the sensor portion and is discharged to the outside due to the tilting of the container according to the eighth embodiment of the present invention.
Figure 27:
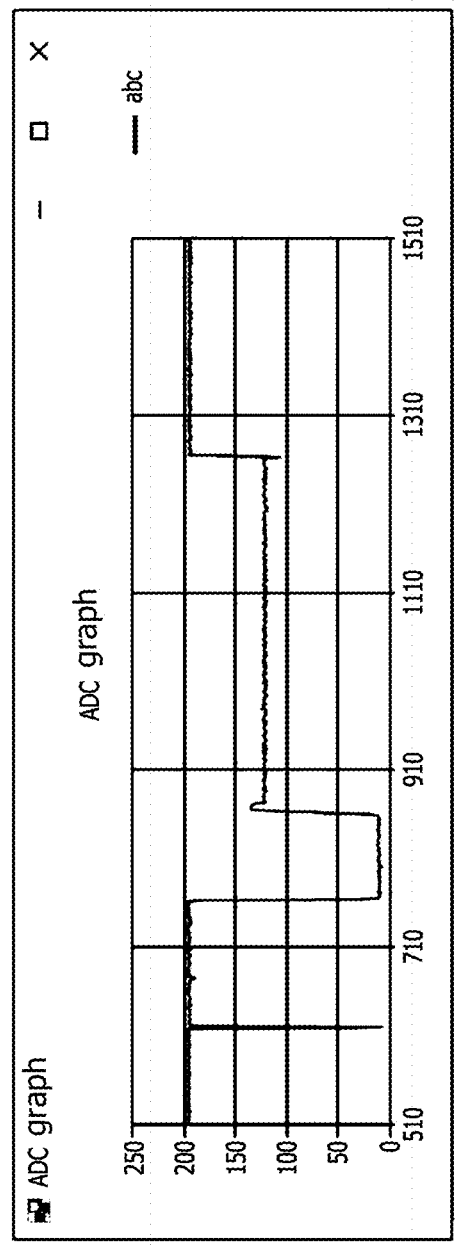
FIG. 27 is a view illustrating changes in a quantity of light in a case in which a relatively small, flat pill is stuck at a container inlet passing device due to the tilting of the container according to the eighth embodiment of the present invention and then re-enters the container due to making the container stand upright again.
Figure 28:
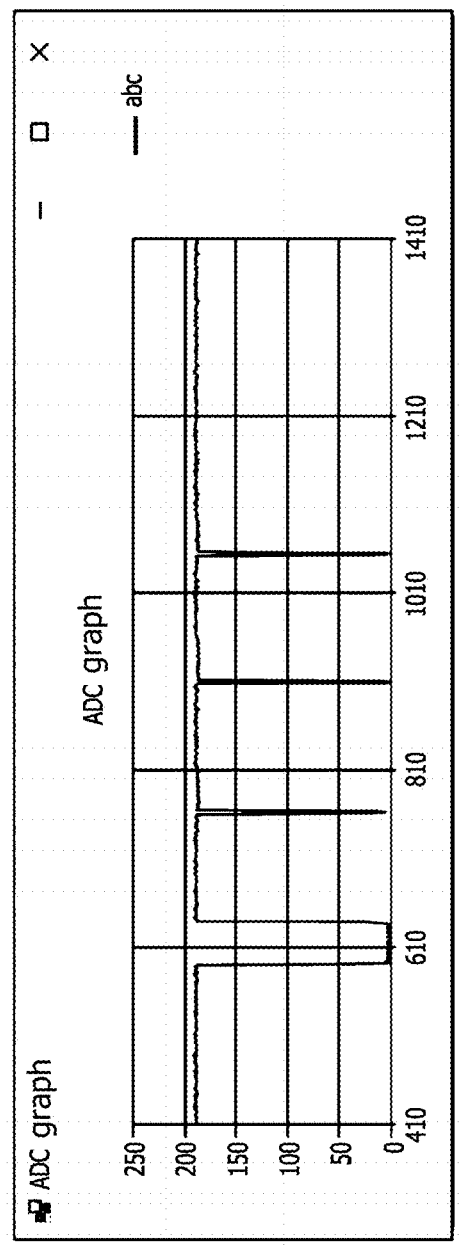
FIG. 28 is a view illustrating changes in a quantity of light in a case in which a relatively large, long pill is stuck at the container inlet passing device due to the tilting of the container according to the eighth embodiment of the present invention and then re-enters the container due to making the container stand upright again.

FIG. 25 is a view illustrating changes in the quantity of light when a relatively small, flat pill passes a sensor portion and is discharged to the outside due to tilting of a container according to the eighth embodiment of the present invention. FIG. 26 is a view illustrating changes in the quantity of light when a relatively large, long pill passes the sensor portion and is discharged to the outside due to the tilting of the container according to the eighth embodiment of the present invention. FIG. 27 is a view illustrating changes in the quantity of light in a case in which a relatively small, flat pill is stuck at a container inlet passing device due to the tilting of the container according to the eighth embodiment of the present invention and then re-enters the container due to making the container stand upright again. FIG. 28 is a view illustrating changes in the quantity of light in a case in which a relatively large, long pill is stuck at the container inlet passing device due to the tilting of the container according to the eighth embodiment of the present invention and then re-enters the container due to making the container stand upright again.

FIG. 25 illustrates a change in the quantity of light in the case in which a relatively small, flat pill is discharged. FIG. 25A illustrates a change in the quantity of light when a relatively small, flat pill is discharged, and FIG. 25B illustrates the change in the quantity of light with the horizontal axis zoomed in. It can be seen that, when light emitted from the light emitting part 410 is detected by the light receiving part 420, because the light emitted from the light emitting part 410 is reflected by the pill, the light receiving part 420 receives a relatively small quantity of light. For reference, FIG. 25 shows results of sampling fifty times per second when the pill is discharged.

A pill discharge sensing principle is as follows. The light emitting part 410 emits light, and the light receiving part 420 detects an amount of passed light using a light detection element. An analog value detected by the light receiving part 420 may be converted using an analog-to-digital converter (ADC) to obtain a sampling value, and whether a pill passes may be detected using the sampling value. FIG. 25 is a graph showing results of sampling fifty times per second when a relatively small, flat pill is discharged.

FIG. 26 illustrates a change in the quantity of light in the case in which a relatively large, long pill is discharged. FIG. 26A illustrates a change in the quantity of light when a relatively large, long pill is discharged, and FIG. 26B illustrates the change in the quantity of light with the horizontal axis zoomed in. It can be seen that, when light emitted from the light emitting part 410 is detected by the light receiving part 420, because the light emitted from the light emitting part 410 is reflected by the pill, the light receiving part 420 receives a relatively small quantity of light. For reference, FIG. 26 shows results of sampling fifty times per second when the pill is discharged. Here, the horizontal axis represents a sampling time (time interval, 1=20 msec), and the vertical axis represents a sampling value.

A pill discharge sensing principle is as follows. The light emitting part 410 emits light, and the light receiving part 420 detects an amount of passed light using a light detection element. An analog value detected by the light receiving part 420 may be converted using an ADC to obtain a sampling value, and whether a pill passes may be detected using the sampling value. FIG. 25 is a graph showing results of sampling fifty times per second when a relatively small, flat pill is discharged.

FIG. 27 illustrates a change in the quantity of light in the case in which a relatively small, flat pill is stuck at a container inlet and then re-discharged. That is, FIG. 27 relates to the case in which a relatively small, flat pill is stuck at a container inlet passing device due to the tilting of the container and then re-enters the container due to making the container stand upright again.

Referring to FIG. 27, in a state in which the relatively small, flat pill is stuck at the container inlet, light emitted from the light emitting part 410 is detected in a relatively small quantity by the light receiving part 420, and such a state continues. Then, when a user makes the housing 110 stand upright, because the light emitted from the light emitting part 410 is received as it is by the light receiving part 420, the quantity of light received by the light receiving part 420 is relatively increased again.

The horizontal axis represents a sampling time (time interval, 1=20 msec), and the vertical axis represents a sampling value. The case in which the pill re-enters is checked using a value of a motion sensor (using a z-axis value).

In this case, in the state in which the relatively small, flat pill is stuck at the container inlet, because the light emitted from the light emitting part 410 is detected in a relatively small quantity by the light receiving part 420, and such a state continues for a predetermined amount of time, on the basis of this, it can be recognized that the pill is stuck in the passing device 100 in the process of being discharged.

Meanwhile, when the user tilts the housing 110 again to discharge the pill, and thus the pill is discharged, as illustrated in FIG. 25, the light emitted by the light emitting part 410 is reflected by the pill, and the light receiving part 420 receives a relatively small quantity of light.

FIG. 28 illustrates a change in the quantity of light in the case in which a relatively large, long pill is stuck at a container inlet and then re-discharged. That is, FIG. 28 relates to the case in which a relatively large, long pill is stuck at a container inlet passing device due to the tilting of the container and then re-enters the container due to making the container stand upright again.

Referring to FIG. 28, in a state in which the relatively large, long pill is stuck at the container inlet, light emitted from the light emitting part 410 is detected in a relatively small quantity by the light receiving part 420, and such a state continues. Then, when a user makes the housing 110 stand upright, because the light emitted from the light emitting part 410 is received as it is by the light receiving part 420, the quantity of light received by the light receiving part 420 is relatively increased again.

In this case, in the state in which the relatively large, long pill is stuck at the container inlet, because the light emitted from the light emitting part 410 is detected in a relatively small quantity by the light receiving part 420, and such a state continues for a predetermined amount of time, on the basis of this, it can be recognized that the pill is stuck in the passing device 100 in the process of being discharged.

Meanwhile, when the user tilts the housing 110 again to discharge the pill, and thus the pill is discharged, as illustrated in FIG. 28, the light emitted by the light emitting part 410 is reflected by the pill, and the light receiving part 420 receives a relatively small quantity of light.

The horizontal axis represents a sampling time (time interval, 1=20 msec), and the vertical axis represents a sampling value. The case in which the pill re-enters is checked using a value of a motion sensor (using a z-axis value).

An operational process of the passing device according to the eighth embodiment of the present invention will be described in detail with reference to FIG. 29.

Referring to FIG. 29, first, the sensing control part 430 controls the light emitting part 410 and emits light (S400).

The light emitted by the light emitting part 410 may be partially or entirely blocked by the contents 5 according to whether the contents 5 are discharged by the passing operation part 120, and, as a result, the quantity of light received by the light receiving part 420 is reduced according to discharge of the contents 5.

Thus, the sensing control part 430 determines whether the light emitted from the light emitting part 410 is received by the light receiving part 420 (S410), and, when, as a result of the determination, the light emitted from the light emitting part 410 is determined as having been received by the light receiving part 420, the sensing control part 430 determines whether the quantity of light received by the light receiving part 420 is less than or equal to the predetermined quantity of light (S420).

The sensing control part 430 determines that the contents 5 are being discharged by the passing operation part 120 when, as a result of the determination in Operation S420, the quantity of light is determined as being less than or equal to the predetermined quantity of light (S430) and determines that the contents 5 are not being discharged by the passing operation part 120 when the quantity of light exceeds the predetermined quantity of light (S440).

Meanwhile, in the above process, when, after a state in which the quantity of light received by the light receiving part 420 is the predetermined quantity of light or larger is reached, the quantity of light reaches the state of being less than the predetermined quantity of light, the sensing control part 430 may determine that the contents 5 have been discharged by the passing operation part 120.

Further, the sensing control part 430 may determine that the contents 5 have been discharged when the quantity of light reaches a state of being less than the predetermined quantity of light in a state in which the slope of the housing 1 sensed by the tilt sensor 530 is within the predetermined slope and may determine that the contents 5 have not been discharged when the quantity of light reaches a state of being less than the predetermined quantity of light in a state in which the slope of the housing 1 sensed by the tilt sensor 530 is beyond the predetermined slope.

For reference, the technical scope of the present invention is not limited to the above. The sensor part configured to determine whether the contents pass through the passing device may further include a distance sensor, a speed sensor, a magnetic sensor, a vision sensor, an acceleration sensor, an angular velocity sensor, a rotation sensor, an infrared sensor, a temperature sensor, an ultrasonic sensor, a touch sensor, an inclination sensor, a load sensor, a pressure sensor, a tension sensor, and a vibration sensor.

Also, the sensor part 510 may have a transmission/reception medium of the transmitting part 460 and the receiving part 470 arranged at one side or both sides so that passage of the contents 5 is sensed without an apparatus coming into contact with the passing movement part 140, which is moving, or may come into contact with the passing movement part 140 and sense physical rotation operation of the passing movement part 140 in order to sense whether the passing device rotates or moves.

Further, when the tilt sensor 530 reaches a predetermined slope or more, the sensing control part 430 may control the sensor part 510 and minimize power consumption required to sense discharge of the contents 5.

Figure 30:
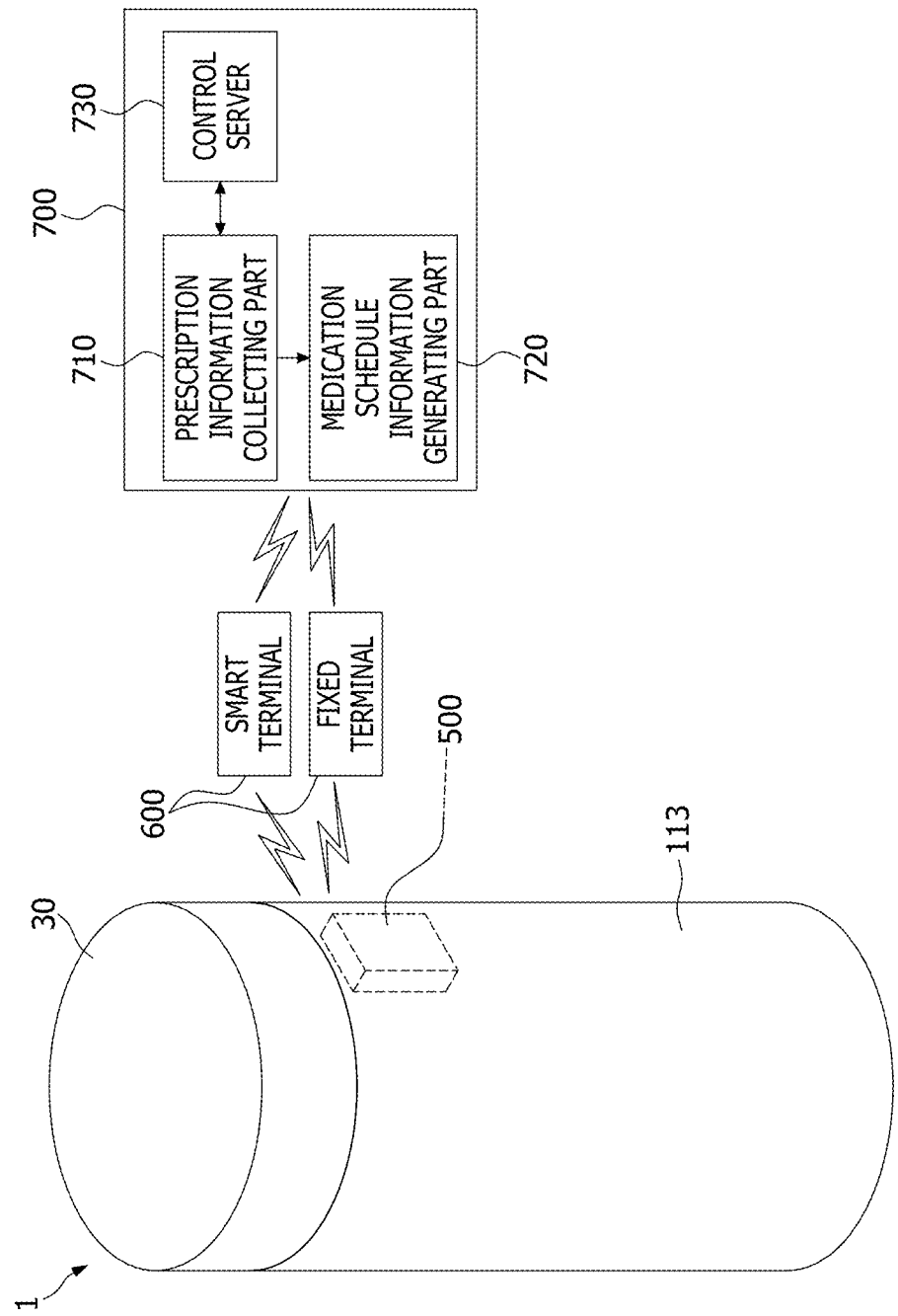
FIG. 30 is a block diagram of a medication management device according to a ninth embodiment of the present invention.
Figure 31:
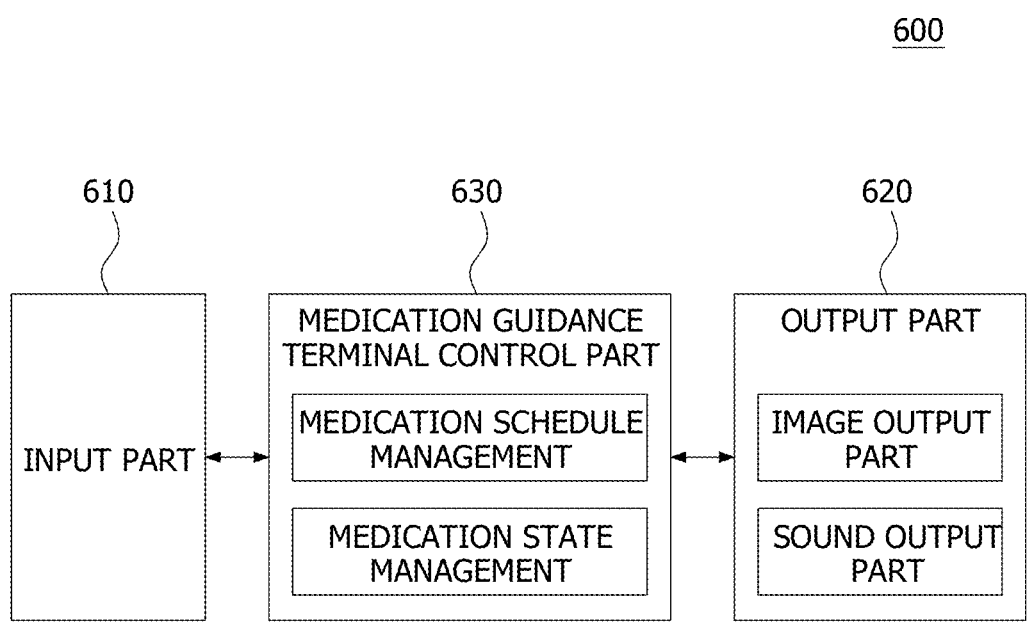
FIG. 31 is a block diagram of a medication guidance terminal of the medication management device according to the ninth embodiment of the present invention.
Figure 32:
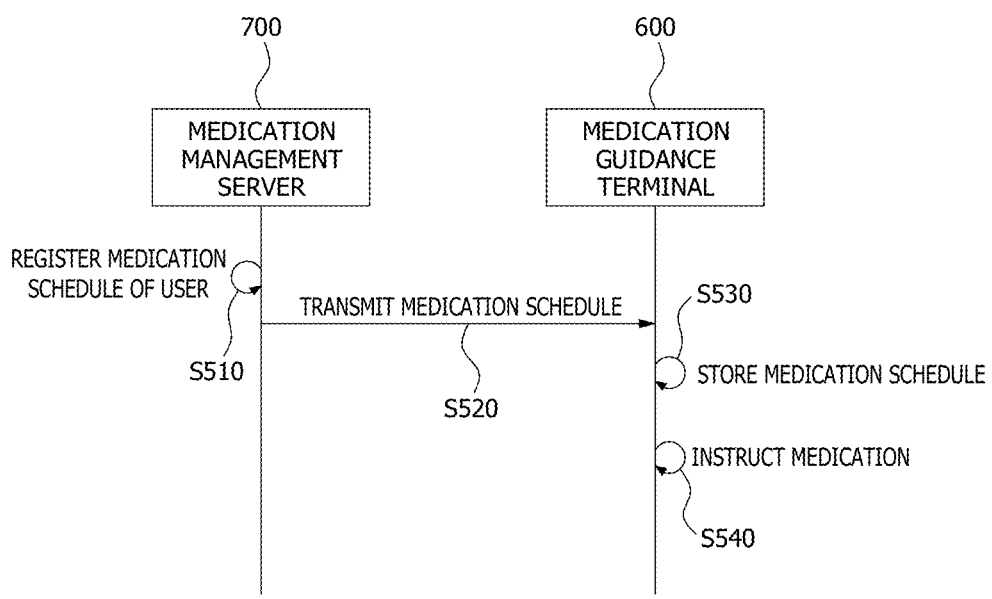
FIG. 32 is a block diagram of the medication guidance terminal according to the ninth embodiment of the present invention.
Figure 33:
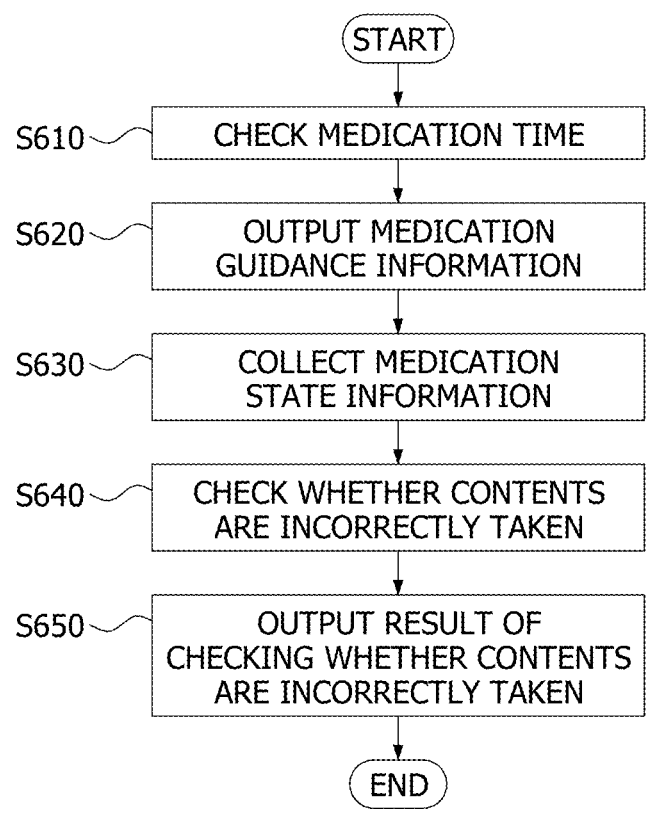
FIG. 33 is a flowchart illustrating an operational process of the medication management device according to the ninth embodiment of the present invention.
Figure 34:
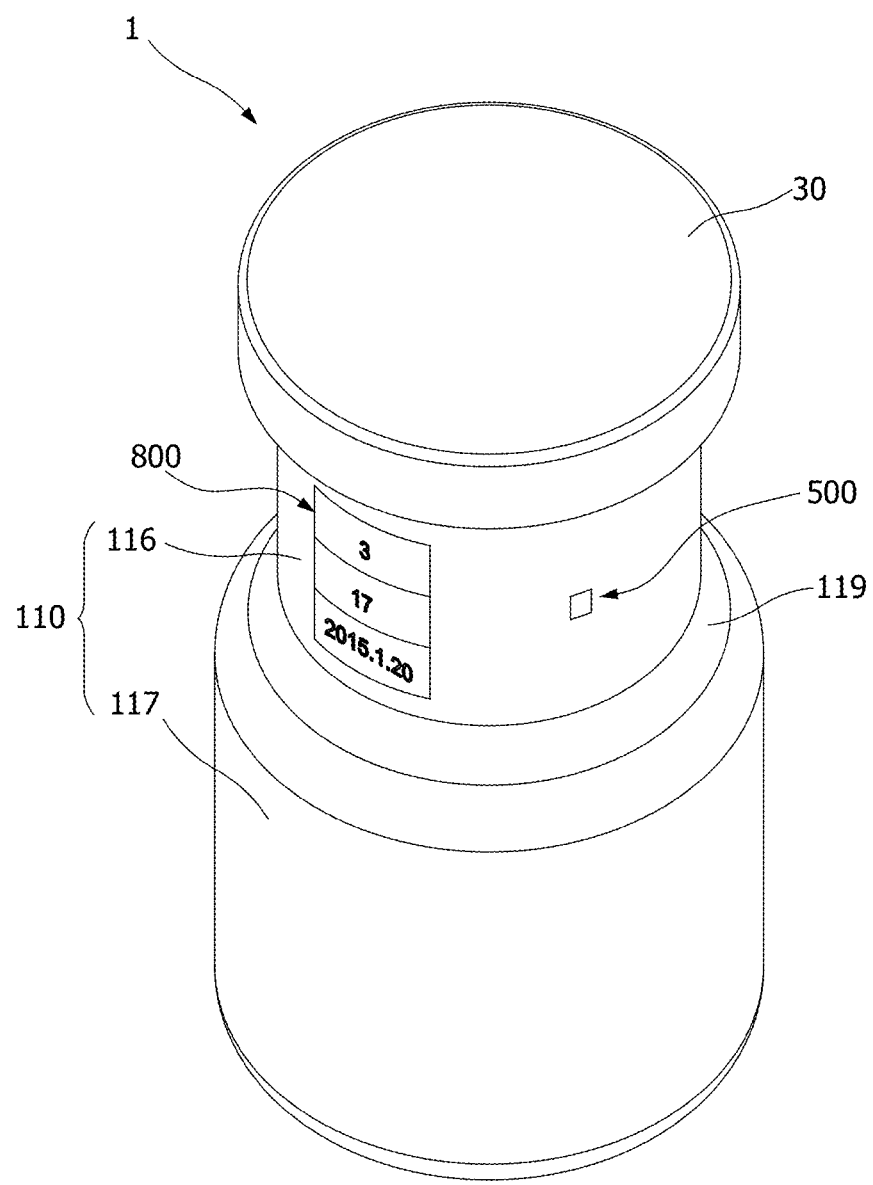
FIG. 34 is a perspective view of a housing having the medication management device according to the ninth embodiment of the present invention.
Figure 35:
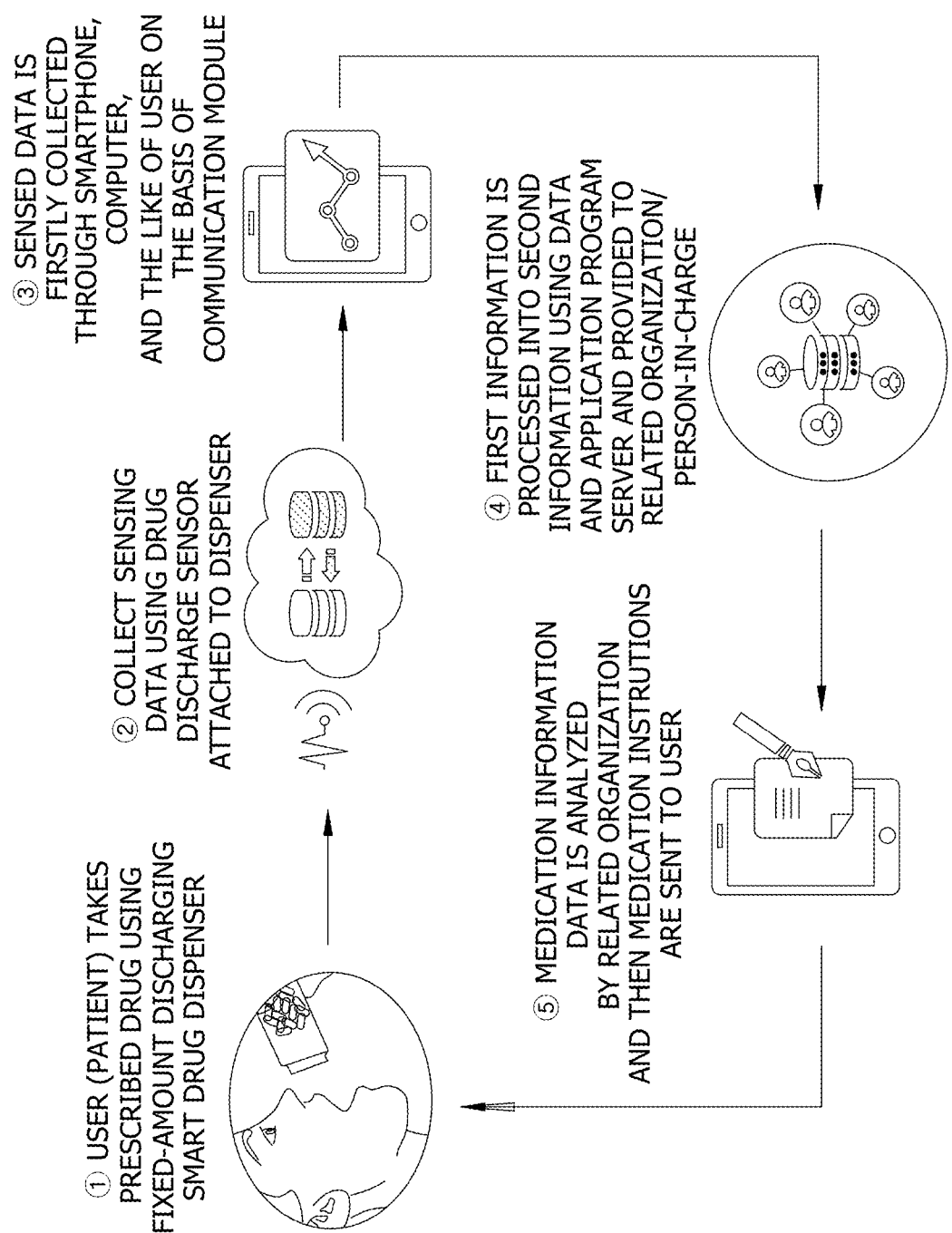
FIG. 35 illustrates a communication system of the medication management device according to the ninth embodiment of the present invention.
Figure 36:
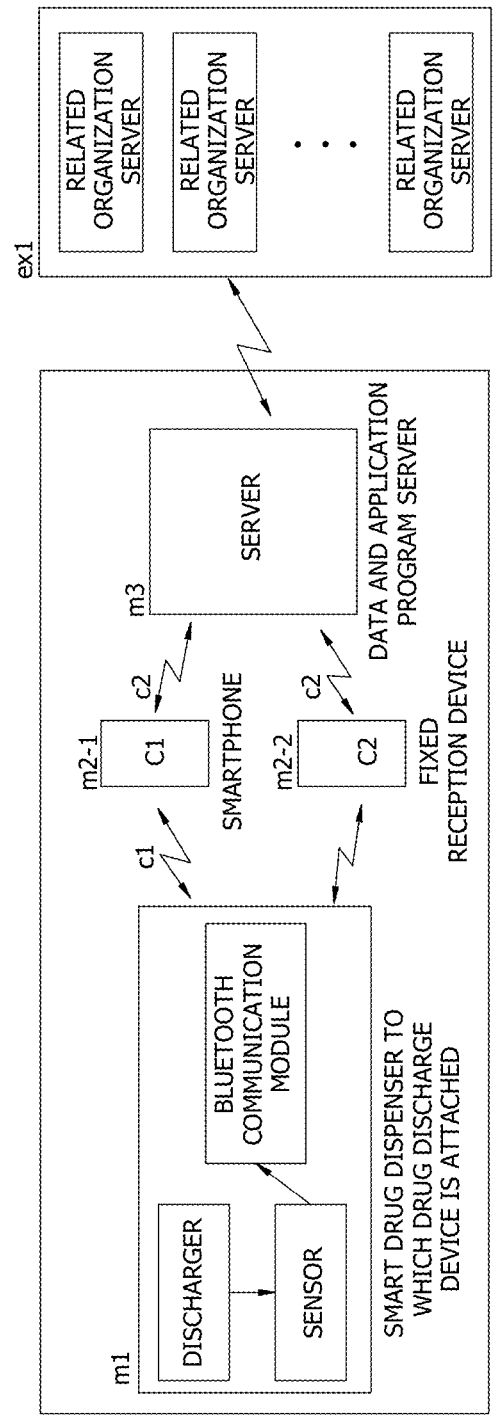
FIG. 36 is an operational view of communication of the medication management device according to the ninth embodiment of the present invention.

FIG. 30 is a block diagram of a medication management device according to a ninth embodiment of the present invention, FIG. 31 is a block diagram of a medication guidance terminal of the medication management device according to the ninth embodiment of the present invention, FIG. 32 is a block diagram of the medication guidance terminal according to the ninth embodiment of the present invention, FIG. 33 is a flowchart illustrating an operational process of the medication management device according to the ninth embodiment of the present invention, FIG. 34 is a perspective view of a housing having the medication management device according to the ninth embodiment of the present invention, FIG. 35 illustrates a communication system of the medication management device according to the ninth embodiment of the present invention, and FIG. 36 is an operational view of communication of the medication management device according to the ninth embodiment of the present invention.

As illustrated in FIGS. 30 to 36, the medication management device according to the ninth embodiment of the present invention includes a sensor module 500, a medication guidance terminal 600, and a medication management server 700.

The sensor module 500 senses contents 5 discharged by a passing operation part 120. Because a method of sensing discharge of the contents 5 by the sensor module 500 is the same as that according to the embodiments described above, the detailed description thereof will be omitted.

Meanwhile, a sensing control part 430 of the sensor module 500 senses the contents 5, generates medication state information according to a result of the sensing, and transmits the generated medication state information to the medication guidance terminal 600.

The sensing control part 430 generates the medication state information on the basis of the result of sensing the contents 5 and transmits the generated medication state information to the medication guidance terminal 600.

The medication state information includes information on the contents 5, whether the contents 5 are sensed, and information on a sensing time at which the contents 5 are sensed. The information on the contents 5 may be preset by the sensing control part 430 or the like, and whether the contents 5 are sensed and the sensing time may be detected in real time according to whether the contents 5 are detected by the sensor part 510.

Referring to FIG. 31, the medication guidance terminal 600 receives the medication state information from the sensor module 500, receives medication schedule information from the medication management server 700, generates medication management information using the medication schedule information and the medication state information, and then outputs the generated medication management information.

The medication schedule information includes one or more of information on the contents 5, a medication time, a medication interval, and a medication dose of each content 5. The medication schedule information may be generated by the medication management server 700 on the basis of a prescription made up by a doctor or a pharmacist.

Here, a smart terminal, a computer, a laptop, a fixed terminal, a personal digital assistant (PDA), or the like may be employed as the medication guidance terminal 600. A medication device or the like may be employed as the fixed terminal.

The medication guidance terminal 600 includes an input part 610, an output part 620, and a medication guidance terminal control part 630.

The input part 610 receives various pieces of information and control commands from a user. The pieces of information and control commands input through the input part 610 may include any information and control command related to usage, operations, and settings of the medication guidance terminal 600, such as user information, an application execution command, and a menu settings command. A mechanical button, a touchscreen, or the like may be employed as the input part 610.

The output part 620 outputs various pieces of information in response to control signals from the medication guidance terminal control part 630. The various pieces of information may include medication state information, medication schedule information, medication management information, and the like. Also, the output part 620 warns, by an image or sound, of incorrectly taking the contents 5.

The output part 620 includes both an image output part and a sound output part that respectively output the information or warning using an image and sound.

The medication guidance terminal control part 630 receives medication state information from the sensor module 500, receives medication schedule information from the medication management server 700, generates medication management information related to a user by using the medication schedule information and the medication state information, and outputs the generated medication management information through the output part 620.

That is, when the medication guidance terminal control part 630 receives the medication state information from the sensor module 500 and receives the medication schedule information from the medication management server 700, the medication guidance terminal control part 630 compares the medication state information and the medication schedule information, generates the medication management information according to a result of the comparison, and outputs the generated medication management information. In this case, the medication guidance terminal control part 630 may warn, through the output part 620, of incorrectly taking the contents.

In the present embodiment, incorrectly taking the contents includes any circumstances in which the contents 5 are not taken or the contents 5 are not taken according to a prescription, such as not taking the contents 5 by a prescribed amount, not taking the contents 5 at a prescribed medication time, and not taking the contents 5.

Meanwhile, the medication state information includes information on the contents 5, whether contents 5 are sensed, and information on a sensing time at which the contents 5 are sensed, and the medication schedule information includes information on the contents 5, a medication time, a medication interval, and a medication dose of each content 5. The medication guidance terminal control part 630 compares and analyzes the pieces of information, checks whether the user incorrectly takes the contents 5, generates medication management information for managing the contents 5 to be accurately taken, and outputs the generated medication management information.

For example, the medication guidance terminal control part 630 may output text or sound that guides the user to take the contents 5 at a prescribed medication time when the user does not take the contents 5 at the medication time and may output text or sound that guides the user to take the contents 5 by a prescribed amount when the user does not take the contents 5 by the prescribed amount.

Also, when, as described above, the medication guidance terminal control part 630 receives the medication schedule information from the medication management server 700, the medication guidance terminal control part 630 outputs one or more of the information on the contents 5 and the medication dose of each content 5 via the output part 620 according to one or more of the medication time and the medication interval.

That is, the medication guidance terminal control part 630 checks the medication time or the medication interval and, when the medication time at which the user should take the contents 5 comes, outputs information on the contents 5 that should be taken and the medication dose of the corresponding contents 5 through the output part 620 so that the user takes the corresponding contents 5 by a fixed amount at an accurate time.

Further, when, as described above, the medication guidance terminal control part 630 receives the medication state information from the sensor module 500, the medication guidance terminal control part 630 accumulates and stores the medication state information and generates medication history information by using the medication state information. The medication history information includes a date and time of mediation, the contents 5 taken and a dose thereof, and the like.

Then, the medication guidance terminal control part 630 outputs the medication history information, e.g., a date and time of mediation, the contents 5 taken and a dose thereof, and the like, according to a control command input through the input part 610.

Therefore, the user may easily recognize, in chronological order, his or her past medication time, contents 5 taken and dose thereof, and the like.

The medication management server 700 collects prescription information from a terminal of a doctor or a pharmacist, generates medication schedule information using the collected prescription information, and then transmits the generated medication schedule information to the medication guidance terminal 600.

The medication management server 700 includes a prescription information collecting part 710, a medication schedule information generating part 720, and a control server 730.

The prescription information collecting part 710 collects prescription information for each user from a terminal of a doctor or a pharmacist.

The medication schedule information generating part 720 uses the prescription information collected by the prescription information collecting part 710 and generates and updates medication schedule information for each user.

The control server 730 controls the prescription information collecting part 710 and collects the prescription information from a terminal (not illustrated) of a doctor or a pharmacist. Then, the control server 730 controls the medication schedule information generating part 720 and generates medication schedule information.

When the medication schedule information is generated as above, the control server 730 detects user information of a corresponding user and transmits medication schedule information to the medication guidance terminal 600 of the corresponding user on the basis of the user information, e.g., contact information.

Hereinafter, a medication management method according to the ninth embodiment of the present invention will be described with reference to FIGS. 32 and 33.

Referring to FIG. 32, first, the control server 730 of the medication management server 700 uses the prescription collecting part and collects prescription information for each user from a terminal of a doctor or a pharmacist.

When the prescription information is collected, the control server 730 controls the medication schedule information generating part 720 to generate medication schedule information using the prescription information, and, when the medication schedule information is generated by the medication schedule information generating part 720, the control server 730 stores the generated medication schedule information of a user (S510).

Further, as the medication schedule information is generated, the control server 730 detects user information of the corresponding user and transmits the medication schedule information to the medication guidance terminal 600 of the corresponding user by using contact information of the user information (S520).

When the medication schedule information is transmitted, the medication guidance terminal 600 stores the corresponding medication schedule information (S530) and performs a medication management process related to the user by using the medication state information received from the sensor module 500 and the medication schedule information (S540).

Referring to FIG. 33, first, upon receiving medication schedule information from the medication management server 700, the medication guidance terminal control part 630 of the medication guidance terminal 600 stores the medication schedule information.

Then, the medication guidance terminal control part 630 checks a medication time of the medication schedule information (S610) and determines whether the current time coincides with the medication time.

When, as a result of the determination, the current time coincides with the medication time, the medication guidance terminal control part 630 outputs medication guidance information, e.g., one or more of information on the contents 5 and a medication dose of each content 5, through the output part 620 according to the medication time (S620).

Accordingly, the user recognizes that the medication time has come and takes the contents 5 by referring to the information on the contents 5 and the medication dose of each content.

In this case, the user tilts a contents moving apparatus 1 to discharge the contents, and because of this, the contents 5 are discharged by a passing operation part 120.

In this case, the sensing control part 430 determines, using the sensor part 510, whether the contents 5 are discharged.

In this way, the sensing control part 430 generates medication state information on the basis of whether the contents 5 are discharged and transmits the generated medication state information to the medication guidance terminal 600.

Meanwhile, the medication guidance terminal control part 630 continuously collects the medication state information transmitted from the sensing control part 430 (S630), generates medication management information related to a user by using the medication state information and the medication schedule information received from the medication management server 700, and outputs the generated medication management information through the output part 620.

That is, the medication guidance terminal control part 630 compares the medication state information with the medication schedule information and generates and outputs the medication management information according to a result of the comparison. The medication guidance terminal control part 630 checks whether the user incorrectly takes the contents 5, e.g., does not take the contents 5 by a prescribed amount, does not take the contents 5 at a prescribed medication time, or does not take the contents 5, and outputs a result of the checking (S640, S650).

Further, when, as described above, the medication guidance terminal control part 630 receives the medication state information from the sensing control part 430, the medication guidance terminal control part 630 accumulates and stores the medication state information and generates medication history information using the medication state information.

Meanwhile, the sensor module 500 may further include a display part 800 so that data sensed or measured or whether the contents passed through the passing operation part 120 by operation of the contents passing means 123 may be recognized using one or more senses such as visual sense, auditory sense, and sense of touch of a user. The display part 800 may display one or more of numbers, text, symbols, braille, emitted light, turned-on light, and colors.

Meanwhile, the sensing control part 430 may output text or sound that guides a user to take the contents 5 at a prescribed medication time when the user does not take the contents 5 at the medication time and may output text or sound that guides the user to take the contents 5 by a prescribed amount when the user does not take the contents 5 by the prescribed amount.

The sensing control part 430 may detect one or more of the number of passed contents, and a date, day, and time at which the contents are passed.

Figure 45:
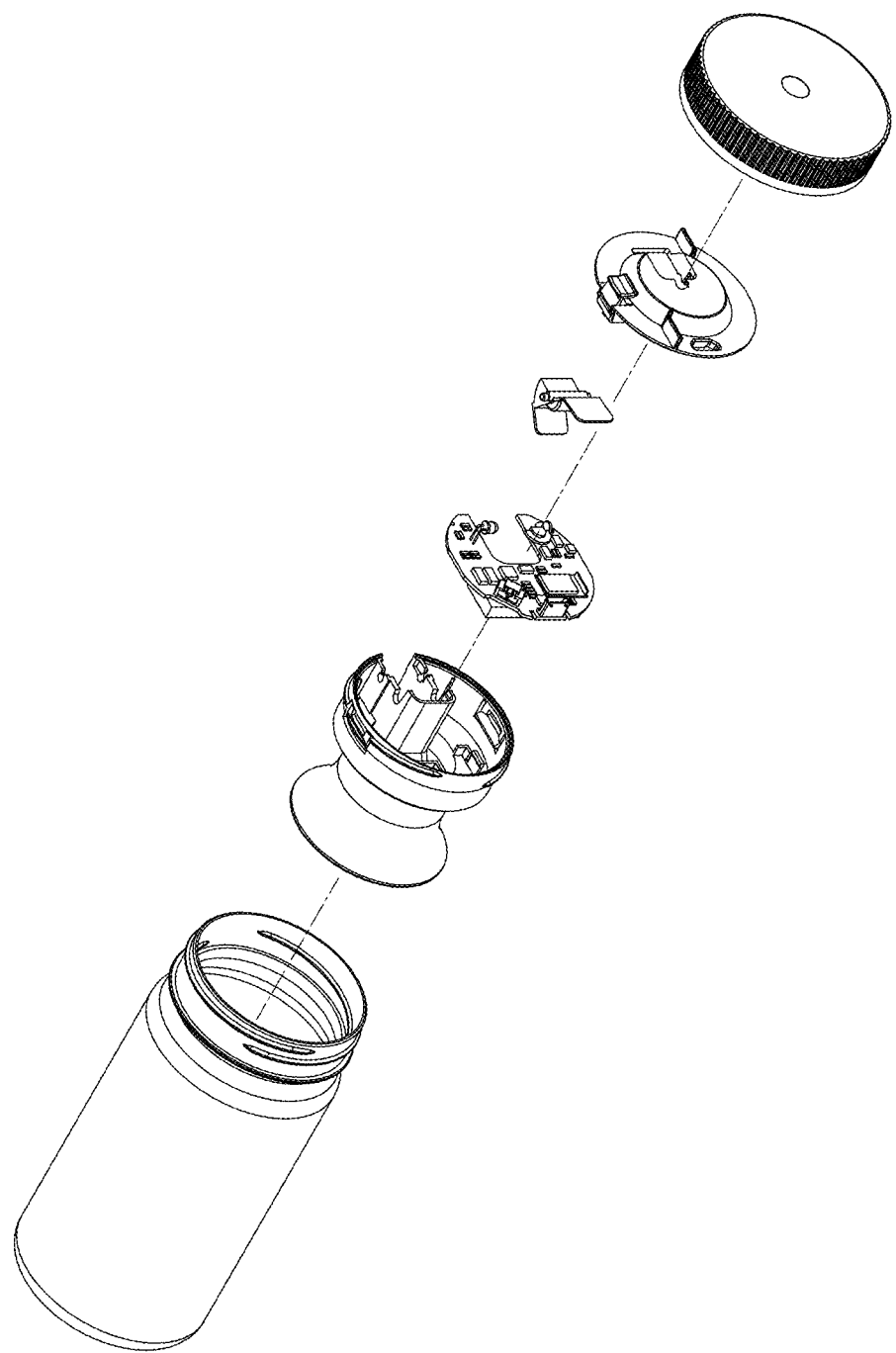
FIG. 45 is an overall exploded perspective view of a dispenser connected to a management terminal according to an embodiment of the present invention.

That is, as illustrated in FIG. 45, the sensing control part 430 displays data sensed or measured or whether the contents passed through the passing operation part 120 by operation of the contents passing means 123 on the display part 800 so that the data sensed or measured or whether the contents passed through the passing operation part 120 by operation of the contents passing means 123 can be recognized using one or more senses such as visual sense, auditory sense, and sense of touch of the user. The display part 800 may display one or more of numbers, text, symbols, braille, emitted light, turned-on light, and colors.

Meanwhile, upon sensing that a prescribed amount of contents passes through the contents passing means 123 during a predetermined period or time or sensing that contents exceeding the prescribed amount pass through the contents passing means 123, the sensing control part 430 may limit contents moving operation of the contents passing means 123.

The sensor module 500 configured to sense passage of contents when the contents pass through the contents passing means 123 may be included, whether the contents passed or the number of contents passed that is sensed by the sensor module 500 may be determined, and whether the contents passed or the number of contents passed determined above, or one or more data of a date, day, and time of the passage of the contents in addition to the whether the contents passed or the number of contents passed determined above may be displayed on the display part 800. The display part 800 may display one or more of numbers, text, symbols, and signals using a liquid crystal display (LCD) or a light emitting diode (LED).

The sensing control part 430 may include a communication part configured to transmit the data sensed or measured. The sensing control part 430 may determine whether the contents passed or the number of the contents passed, which have been sensed, and transmit whether the contents passed or the number of contents passed determined above or transmit one or more data of a date, day, and time of the passage of the contents in addition to the whether the contents passed or the number of contents passed determined above, in proximity or remotely through the communication part.

Also, the sensing control part 430 may include a locking part configured to prevent passage of more contents through the passing device when the sensing control part 430 senses contents passed through the contents passing means 123 and it is determined that a designated amount of contents has passed. The locking part is disposed in the passing device to prevent movement of the contents passing means 123 or block a movement path of the contents in the passing operation part 120.

In this case, the prevention of the movement of the contents passing means 123 may be performed by contact resistance with a movement portion of the contents passing means, and the blocking of the movement path in the passing operation part 120 may be performed by blocking or resisting contents by a passing passage part disposed at a passing entry side and a passing discharge side of the contents. When regulation is required in cases of a drug that requires to be taken in a limited dose by patients or a food that requires restricted intake of normal people, the locking part may maintain a locked state at a designated time or before a situation ends.

Also, one or more of numbers, text, and symbols may be marked on a surface of the contents or inside the contents so that the marks on the contents that passed through the contents passing means 123 or the contents that did not pass through the contents passing means 123 may be observed.

FIG. 35 is a data flowchart of a medication data management system according to the ninth embodiment of the present invention. 1) when a user takes a prescription drug using a fixed-amount discharging smart drug dispenser, a patient who takes the drug passes only a fixed amount of contents in a container just by tilting the drug container and discharges medicine or health supplement in the form of a pill one at a time so that it is convenient, sanitary, and spoilage of contents is prevented; 2) as sensing data can be collected by a drug discharge sensor attached to a dispenser, a drug dispenser for systematic medication management of a patient is developed by attaching a sensor configured to check discharge of drugs to the dispenser; 3) sensed data is firstly collected through a smartphone, a computer, and the like of a user on the basis of a communication module; 4) first information is processed into second information using data and an application program server and provided to a person concerned; and 5) the medication information data is analyzed by a related organization, and then medication instructions are sent to a user. A remote medication management system that utilizes the above may be constructed.

Particularly, a drug discharge check sensor may be attached for medication management. The drug discharge check sensor for checking a medication state, which is an obligation of a patient, and a communication device using Bluetooth or the like may be attached. Also, for cost reduction and efficiency of manufacturing, an integrated type sensor and an integrated type communication device may be designed and applied.

To maximize a therapeutic effect for a disease, in addition to medical staff (doctors and pharmacists), who are the subject of medical treatment, patients, who are medical service users, should also actively fulfill their obligations related to the medical treatment. This is possible through the remote medication management system as in the present embodiment.

Data collected by a sensor attached to a drug dispenser may be firstly collected using a smartphone or a specialized device using a one-board computer by using a communication module. The firstly collected information may be transmitted to a server, and second information collected by the server may be processed and provided to doctors, pharmacists, National Health Insurance Service, and the like.

The smartphone or the specialized device may notify a patient of medication obligations, continuously notify the patient of a medication time and a medication dose, and may continuously send out warnings when the patient does not take the drug. The specialized device using a one-board computer (e.g., Raspberry Pi) with built-in Bluetooth and Wi-Fi may be configured for elderly patients who cannot use smartphones.

FIG. 36 is a flowchart illustrating application of medication data management technology according to the ninth embodiment of the present invention. As in m1, a smart drug dispenser to which a drug discharge device is attached includes a discharger, a sensor, and a Bluetooth communication module. m1 may communicate with m2-1 (mobile device: smartphone) or m2-2 (fixed device: one-board computer) through c1 (Bluetooth communication). Also, m2-1 and m2-2 may communicate with m3 (server) through c2 (network).

m3 communicates with Ex1 (related organization server) through c3 (connected by open-api or EAI). Here, a discharge amount is transmitted and an error or confirmation signal is transmitted through c1. Through c2, m2 transmits a discharge amount to m3, and m3 transmits medication management content to m2. Through c3, m3 may transmit discharge amount statistics to Ext, and Ext may transmit medication management content to m3. The c3 communication is connected by open api or EAI, which is a different-type DB connection protocol.

Figure 37:
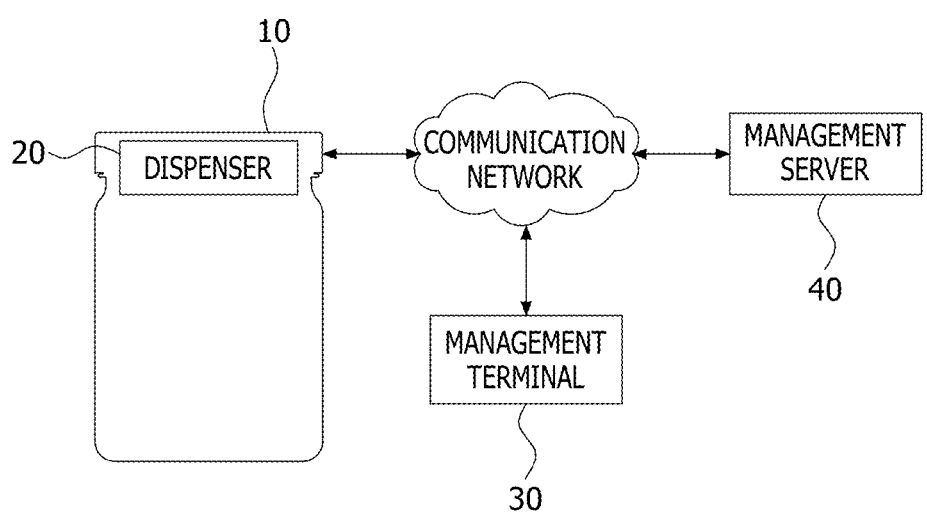
FIG. 37 is a block diagram of a medication management device according to a tenth embodiment of the present invention.
Figure 38:
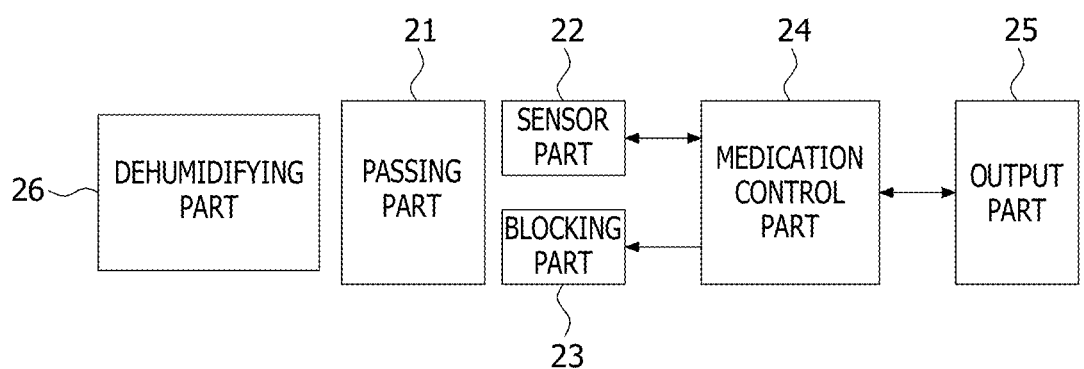
FIG. 38 is a block diagram of a dispenser according to the tenth embodiment of the present invention.
Figure 39:
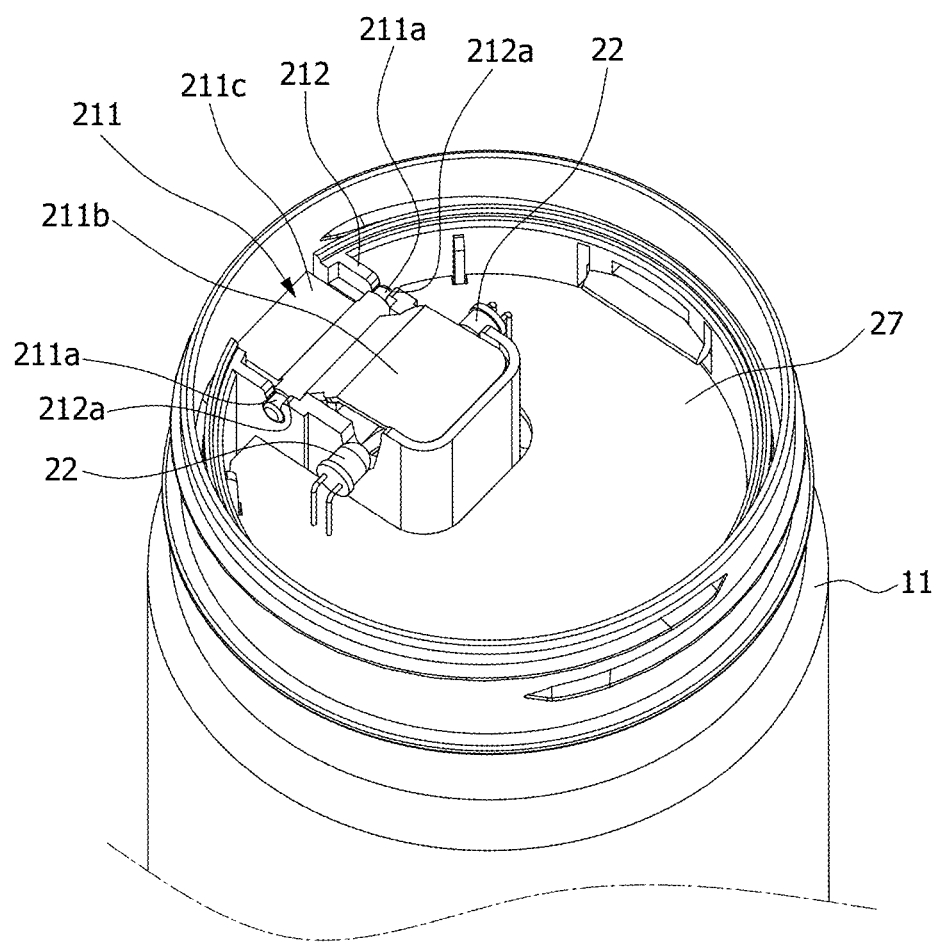
FIG. 39 is a perspective view of a substrate according to the tenth embodiment of the present invention.
Figure 40:
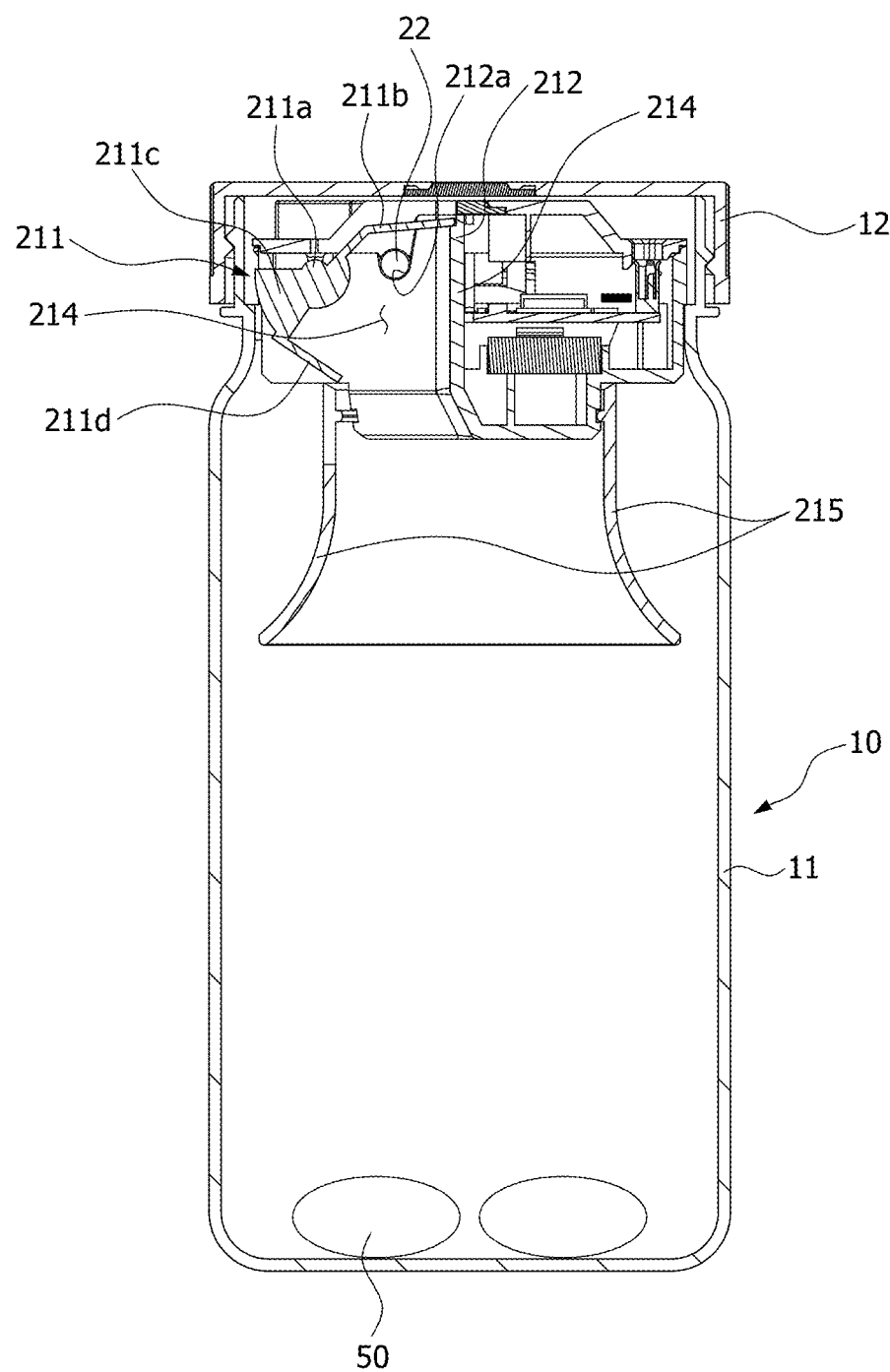
FIG. 40 is a cross-sectional view of the dispenser according to the tenth embodiment of the present invention.
Figure 41:
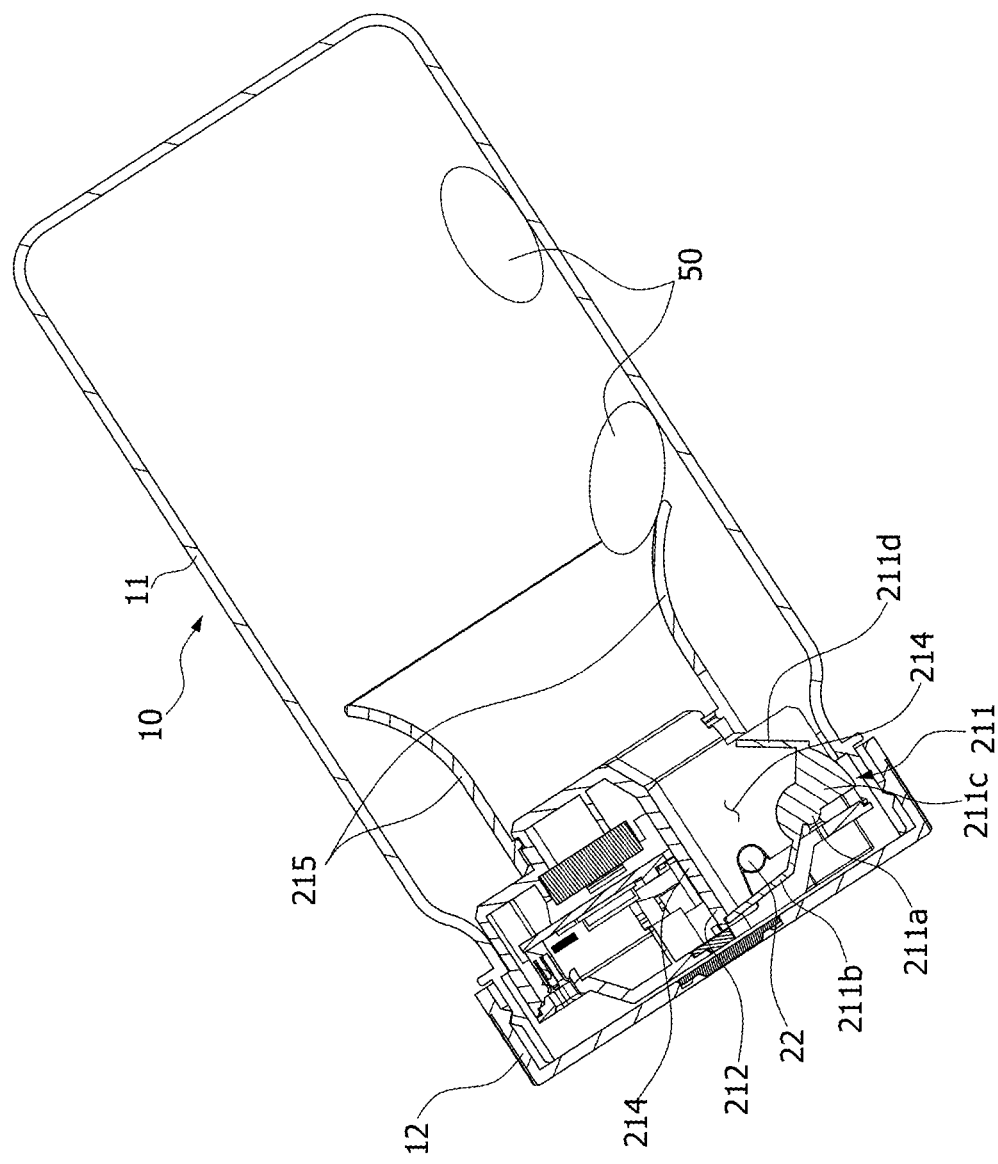
FIGS. 41 to 43 are views illustrating a contents discharging process of the dispenser according to the tenth embodiment of the present invention.
Figure 42:
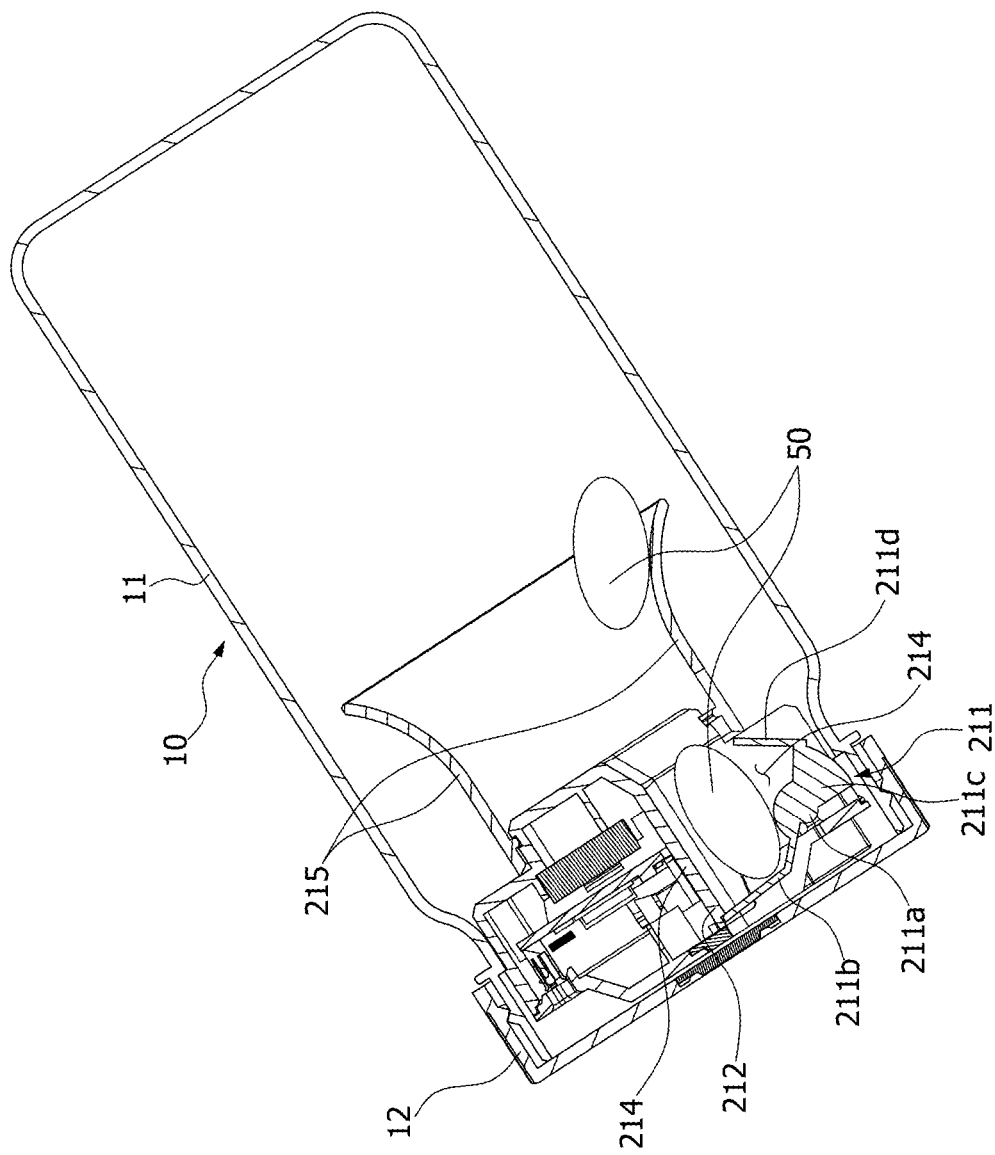
Figure 43:
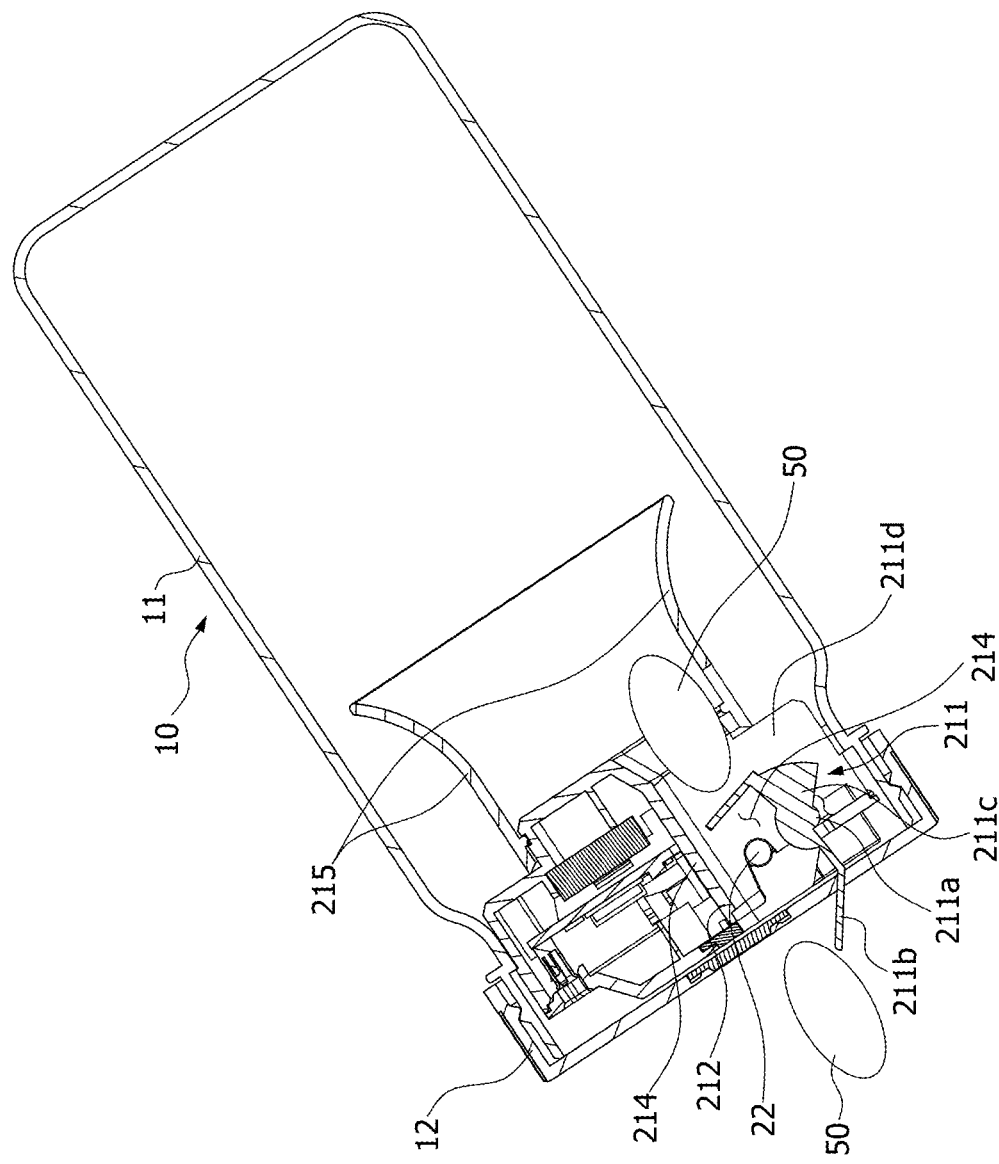
Figure 44:
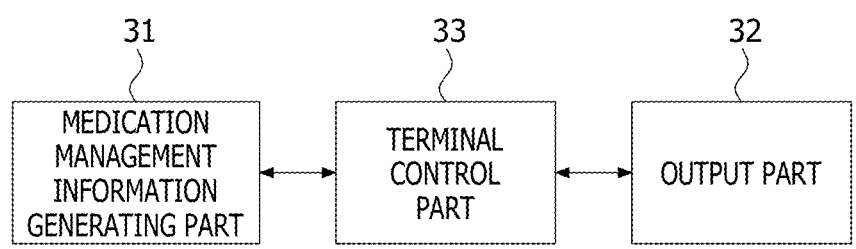
FIG. 44 is a block diagram of a management terminal according to the tenth embodiment of the present invention.

FIG. 37 is a block diagram of a medication management device according to a tenth embodiment of the present invention, FIG. 38 is a block diagram of a dispenser according to the tenth embodiment of the present invention, FIG. 39 is a perspective view of a substrate according to the tenth embodiment of the present invention, FIG. 40 is a cross-sectional view of the dispenser according to the tenth embodiment of the present invention, FIGS. 41 to 43 are views illustrating a contents discharging process of the dispenser according to the tenth embodiment of the present invention, an FIG. 44 is a block diagram of a management terminal according to the tenth embodiment of the present invention.

Referring to FIG. 37, the medication management device according to the embodiment of the present invention includes a container 11, a dispenser 20, a management terminal 30, and a management server 40.

A housing 10 holds contents 50 and includes the container 11 and a cover 12.

The contents 50 are in the form of solid, powder, or liquid that can pass.

The container 11 is formed in a cylindrical shape with an open upper portion and holds the container 11 therein. The dispenser 20 is installed at the upper portion of the container 11. The dispenser 20 allows the contents 5 inside the container 11 to be discharged by a predetermined fixed amount at a time. This will be described in detail below.

The cover 12 is installed at an upper end portion of the container 11 and protects the dispenser 20.

The dispenser 20 is installed in the container 11 and manages discharge of the contents 50 inside the container 11.

The dispenser 20 is installed in the container 11 and causes the contents 50 inside the container 11 to be discharged only by the predetermined amount at a predetermined medication time so that a user is guided to take the contents 50 by a fixed amount at a fixed medication time.

The amount of the contents 50 discharged by the dispenser 20 may be set to various amounts according to characteristics of the contents 50. When the contents 50 are in a solid form, only a single content 50 may be set to be discharged per each operation.

The dispenser 20 generates medication information by sensing whether the contents 50 are actually discharged while discharging the contents 50 to the outside and transmits the medication information to the management terminal 30 or the management server 40. The dispenser 20 manages, on the basis of the medication information, whether the user takes the contents 50 according to medication schedule information. In this case, the dispenser 20 outputs medication guidance information according to an operation scenario set for allowing the user to take the contents 50 by a fixed amount at a fixed time.

Referring to FIG. 38, the dispenser 20 includes a passing part 21, a sensor part 22, a blocking part 23, a medication control part 24, a dispenser output part 25, and a dehumidifying part 26.

The passing part 21 is installed in the container 11 of the housing 10 and causes the contents 50 to be discharged to the outside of the container 11 only by a predetermined amount. That is, the passing part 21 serves to lead movement of the contents 50 by a fixed amount or a demand amount. Here, "fixed amount" refers to the same number or amount or the amount or number varying within an error range. "Demand amount" is an amount (number) required by a user and belongs to the category of "fixed amount."

As illustrated in FIG. 50, the passing part 21 is installed on a substrate 27. The substrate 27 is disposed between the cover 12 and another cover 12 which will be described below.

The passing part 21 includes a valve part 211 and a support part 212.

The support part 212 supports the valve part 211. The support part 212 is formed to correspond to an inner circumferential surface of the upper end portion of the container 11, and the support part 212 includes a seating part 212a formed to support the passing part 21.

The seating part 212a is formed at the support part 212 so as to be rounded and supports the valve part 211. A movement member 211a of the valve part 211, which will be described below, is seated on the seating part 212a and rotates within a predetermined angle range.

The valve part 211 is disposed at an inner side of the container 11, guides movement of the contents 50, and allows the contents 50 to be discharged only by a predetermined amount.

The valve part 211 includes the movement member 211a, an opening member 211b, a blocking member 211d, and a guide part 215.

A movement control member 211c rotates the opening member 211b and the blocking member 211d by the self-weight. The movement member 211a is formed at both side end portions of the movement control member 211c. The movement member 211a is installed at the seating part 212a and rotates counterclockwise due to the self-weight, and thus the opening member 211b and the blocking member 211d rotate.

The opening member 211b is formed to protrude in the shape of a plate from the movement control member 211c. The opening member 211b may be linearly bent or formed as a curved surface. The opening member 211b blocks discharge of the contents 50 to the outside.

However, when the container 11 is tilted to the extent that the contents 50 therein may be discharged to the outside, the movement control member 211c rotates due to its self-weight, and, in this case, the opening member 211b also rotates and is opened such that the contents 50 in an opening 214 are discharged to the outside.

The blocking member 211d is linearly bent or formed as a curved surface and blocks at least a portion of the opening 214 so as to prevent the contents 50 beyond a fixed amount from being introduced into the opening 214.

That is, when the container 11 rotates, due to the blocking member 211d, the fixed amount of contents 50 is located in the opening 214 formed in the opening member 211b and the blocking member 211d, and then, when the container 11 continues to rotate, the opening member 211b also rotates and thus the opening 214 is opened such that the contents 50 in the opening 214 are discharged to the outside.

The guide part 215 guides the contents 50 to be introduced into the opening 214. The shape of the guide part 215 is not particularly limited, and the guide part 215 may be formed in various shapes and structures that allow the contents 50 to be introduced into the opening 214.

That is, in a state in which the container 11 stands upright as illustrated in FIG. 40, the blocking member 211d blocks the contents 50.

However, when the container 11 is tilted to the extent that the contents 50 therein may be discharged to the outside, as illustrated in FIG. 42, the contents 50 are guided along the guide part 215, and, in this case, the movement control member 211c rotates due to its self-weight such that the contents 50 are located in the opening 214 through the guide part 215. In this case, as other contents 50 are blocked by the blocking member 211d, only the fixed amount of contents 50 is located in the opening 214.

Then, when the container 11 is completely tilted such that the contents 50 may be completely discharged, the movement control member 211c is also tilted further. In this case, the opening 214 is opened to the outside by the opening member 211b, and thus the contents 50 located in the opening 214 are discharged to the outside as illustrated in FIG. 43.

Meanwhile, because the blocking member 211d is formed to be bent as described above, subsequently-introduced contents 50 are blocked.

As a result, even when the container 11 is tilted at an angle at which the contents 50 therein may be discharged, only a single content 50, i.e., the fixed amount of contents 50, is discharged to the outside. Then, when the container 11 is made to stand upright, the contents 50 therein fall down due to the self-weight. In this case, due to the self-weight of the movement control member 211c, the opening member 211b also rotates such that the opening 214 is closed.

As illustrated in FIG. 39, the sensor part 22 is installed on the substrate 27 and senses the contents 50 actually passing through the passing part 21.

For example, the sensor part 22 may sense the contents 50 using light, radio waves, or the like. The sensor part 22 may use any other things that allow the contents 50 to be sensed.

The blocking part 23 blocks operation of the passing part 21 on the basis of a passing time of the contents 50 passing through the passing part 21.

For example, when the container 11 is tilted to an angle at which the contents 50 may be discharged before a medication interval elapses from the time the contents 50 previously passed, or when the container 11 is tilted to an angle at which the contents 50 may be discharged before a predetermined medication time comes, the blocking part 23 blocks operation of the passing part 21.

A hinge or a pivot that blocks rotation of the valve part 211 may be employed as the blocking part 23, or a locking member (not illustrated) that blocks rotation of the opening member 211b or the blocking member 211d may be employed as the blocking part 23. The locking member may be operated by driving of a motor, an electromagnet, or the like.

Here, the blocking part 23 may include a tilt sensor therein configured to sense a slope of the container 11. When the slope of the container 11 sensed by the tilt sensor becomes equal to or larger than an angle at which the contents 50 may be discharged, the blocking part 23 may block operation of the passing part 21.

By the blocking part 23 adjusting a medication interval as described above, a user is guided to take a fixed amount of drug or take drug at a fixed time, and the user is prevented from taking an overdose of drug or being addicted to the drug.

The dehumidifying part 26 is installed inside the container 11 and removes moisture from inside the container 11. The dehumidifying part 26 may be installed inside the container 11 using a clip (not illustrated).

The dispenser output part 25 outputs medication guidance information for guiding a user to take drug at a fixed time and take drug by a fixed amount. The medication guidance information may include a medication time and a medication dose.

That is, the dispenser output part 25 outputs medication guidance information according to an operation scenario preset for allowing the user to take drug by a fixed amount at a fixed time. When the current time matches a medication time, the dispenser output part 25 informs the user, by an image or sound, of the fact that the medication time has come.

An LED or a display device may be employed as the dispenser output part 25.

When the dispenser output part 25 is an LED, the LED blinks green when the medication time comes and blinks red when the contents 50 are not sensed by the sensor part 22 even after the medication time. Then, when the contents 50 are sensed by the sensor part 22, the LED blinks one time or a plurality of times and then is turned off. On the other hand, the dispenser output part 25 may also adjust a blinking interval to inform of the fact that the medication time has come.

When the dispenser output part 25 is a display device, the display device may output an image, text, or the like to inform of the fact that the medication time has come.

Further, the dispenser output part 25 may also output an amount of contents 50 remaining inside the container 11.

The dispenser output part 25 is may be installed at an outer side surface of the container 11 and allow the user to easily recognize medication guidance information.

The medication control part 24 generates sensing information on the basis of whether the contents 50 are sensed by the sensor part 22 and manages medication of the user on the basis of the generated sensing information.

First, the medication control part 24 pre-stores medication schedule information including a user name, a medication time, a number of medications, and the like and manages to allow the user to abide by the medication time and the number of medications according to the medication schedule information.

When the contents 50 are sensed by the sensor part 22, the medication control part 24 accumulates and stores a sensing time at which the contents 50 are sensed and a number of times of sensing the contents 50 and generates medication information on the basis of the sensing time and the number of times of sensing. The medication information may include a medication time and a number of medications.

When the medication information is generated as described above, the medication control part 24 transmits the medication information to the management terminal 30 or the management server 40 through a communication network. When transmitting the medication time and the number of medications to the management terminal 30 or the management server 40, communication between the medication control part 24 and the management terminal 30 or communication between the medication control part 24 and the management server 40 may not be performed normally. Thus, the medication control part 24 may also transmit a plurality pieces of medication information at once. In this way, the medication control part 24 may transmit medication information in real time and may also transmit a plurality of pieces of medication information at once according to a communication state or the like.

Various communication networks such as Bluetooth, Wi-Fi, wireless internet, and long term evolution (LTE) may be employed as the communication network.

The medication control part 24 controls the dispenser output part 25 and outputs medication guidance information for guiding a user to take a fixed amount of drug at a fixed time.

That is, the medication control part 24 outputs medication guidance information according to an operation scenario preset for allowing the user to take drug by a fixed amount at a fixed time. When the current time matches a medication time, the medication control part 24 controls the dispenser output part 25 and informs the user, by an image or sound, of the fact that the medication time has come. The medication control part 24 may also output an amount of contents 50 remaining inside the container 11.

Further, when the blocking part 23 operates as described above, the medication control part 24 transmits, to a carer's terminal (not illustrated), the fact that there has been an abnormal attempt to take drug or controls the blocking part 23 according to the medication schedule information so that drug may be taken according to the medication schedule information. That is, when the current time is included in medication times, the medication control part 24 may release the blocking part 23 and allow the user to take drug, and, when the current time is not included in the medication times, the medication control part 24 may control the corresponding blocking part 23 and block operation of the valve part 211 to prevent the user from taking the drug. In this way, the medication control part 24 allows the user to take the drug correctly.

The management terminal 30 generates medication information on the basis of whether the contents 50 are discharged according to operation of the dispenser 20 and transmits the generated medication information to the management server 40.

The management terminal 30 includes a terminal output part 32, a medication management information generating part 31, and a terminal control part 33.

The terminal output part 32 outputs medication management information.

The medication management information generating part 31 analyzes the medication information of the passing part 21 and generates the medication management information. That is, the medication management information generating part 31 compares the medication information of the passing part 21 with preset medication schedule information and generates medication guidance information. The medication management information generating part 31 may compare operation information of the passing part 21 with the pre-stored medication schedule information and generate the medication management information according to whether the operation information of the passing part 21 matches the medication schedule information.

The medication guidance information is information that guides the user to take drug by a fixed amount at a fixed time.

When medication information is transmitted from the dispenser 20, the terminal control part 33 generates medication management information using the medication information through the medication management information generating part 31 and outputs the generated medication management information through the terminal output part 32. Accordingly, the user may recognize the medication management information and take drug according to the preset medication schedule information.

Also, when the medication management information is generated using the medication information, the terminal control part 33 controls the dispenser 20 according to the medication management information, and the dispenser 20 guides the user to take drug according to the corresponding control command.

For example, when a preset medication time comes, the terminal control part 33 controls the dispenser 20 and limits operation of the blocking part 23, and, when the current time does not match the preset medication time, the terminal control part 33 controls the dispenser 20 and blocks operation of the passing part 21 through the blocking part 23 to prevent incorrect medication.

Further, the terminal control part 33 transmits the medication management information to the management server 40, and the management server 40 allows the corresponding medication information to be used in various fields.

Here, a smart terminal or the like of a user may be employed as the management terminal 30, but any other separate repeater having a repeating function may also be employed.

The management server 40 collects medication information of the dispenser 20 from at least one of the dispenser 20 and the management terminal 30 and processes the collected medication information so that the medication information is used in public welfare elderly care, clinical trials, a comparison between a supply amount and a medication dose, inventory management of pharmaceutical companies, inventory management of distributors, a doctor's consultation in hospitals, insurance operation of insurance companies, medical device companies, and the like.

Figure 46:
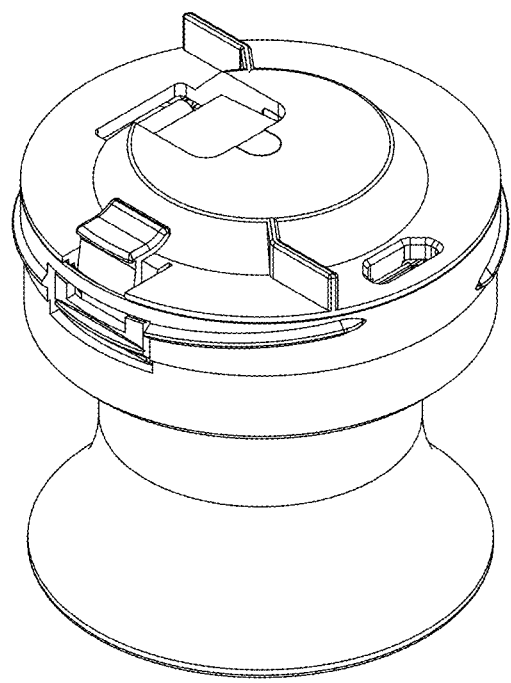
FIG. 46 is a perspective view of a plug cap of the dispenser connected to the management terminal according to an embodiment of the present invention.
Figure 47:
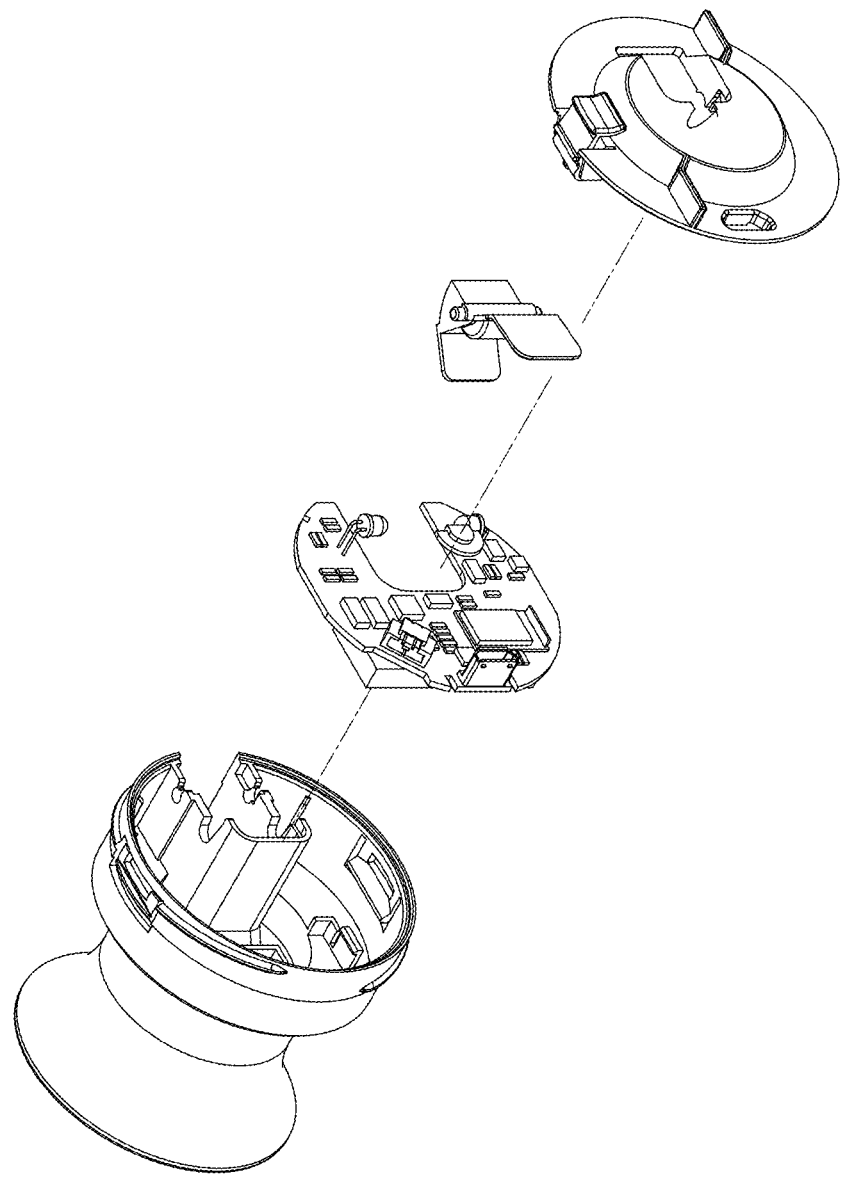
FIG. 47 is an exploded perspective view of the plug cap of the dispenser connected to the management terminal according to an embodiment of the present invention.

Referring to FIGS. 45 to 47, the overall structure and a plug cap structure of a dispenser connected to a management terminal according to an embodiment are illustrated.

The present invention has been described above with reference to embodiments illustrated in the drawings, but the embodiments are merely illustrative, and one of ordinary skill in the art to which the present invention pertains should understand that various modifications and other equivalent embodiments are possible from the above-described embodiments. Therefore, the actual technical scope of the present invention should be defined based on the claims below.

INDUSTRIAL APPLICABILITY

According to the present invention, the amount of contents discharged from a containing apparatus can be accurately sensed, and the user can be allowed to take a fixed amount of contents on the basis of the accurately-sensed amount of contents discharged.

The invention claimed is:
1. A passing device comprising:
a passing operation part having a passing passage to guide movement of content;
a passing movement part having a rotatable structure from which an opening member and a closing member protrudes in different directions from each other, rotatably disposed in the passing operation part and configured to move so that the content is passed;
a sensing part disposed in the passing operation part and configured to sense content discharged due to free rotation of one end of the passing movement part; and
a tilt sensor configured to sense a slope of the passing device,
wherein the sensing part detects information on the sensed content, and
wherein the sensing part includes at least one light emitter configured to emit light toward content discharged due to rotation of the passing movement part, at least one light receiver configured to receive the light emitted from the light emitter, and a sensing controller configured to sense the content discharged through the passing operation part by using the light received by the light receiver and determine that the content has been discharged by the passing movement part according to whether a slope of a container sensed by the tilt sensor is within a predetermined slope range.

2. The passing device of claim 1, wherein the passing movement part further includes a blocking member configured to obstruct passage of content beyond a predetermined amount.

3. The passing device of claim 1, wherein the sensing controller determines that the content has been discharged by the passing operation part if an amount of change in the quantity of light received by the light receiver is equal to and greater than a predetermined amount of change.

4. The passing device of claim 1, wherein if a light quantity detected by the light receiver becomes smaller than a predetermined quantity from the predetermined quantity or more, and then equals to or greater than the predetermined quantity within a predetermined time, it is determined that the content has been discharged by the passing operation part.

5. The passing device of claim 1, wherein the sensing controller determines that the content is discharged by the passing operation part when the quantity of light received by the light receiver reaches a state of being a predetermined light quantity or larger and then reaches a state of being less than the predetermined light quantity.

6. The passing device of claim 1, wherein a rotary motion of passing movement part is restrained or delayed by difference a position of center of gravity of the passing movement part and a position of center of rotation of the passing movement part when the passing operation part is tilted.

7. The passing device of claim 1, wherein if a light quantity detected by the light receiver is smaller than a predetermined quantity and such a state is maintained for a predetermined time duration, it is determined that the content is stuck in the passing device, and
wherein the predetermined time duration is longer than a time duration during which the quantity of light is relatively small when the content is discharged.

8. The passing device of claim 1, further comprising a communication part configured to transmit the information on the content detected by the sensing part, the information stored in the storage part, or the information calculated by the measuring part to an external device through wired or wireless communication.

9. The passing device of claim 1, wherein the sensing controller determines, on the basis of the information stored in the storage part, whether the cumulative discharge amount of the content by period exceeds or is less than a predetermined amount by period.

10. The passing device of claim 3, wherein the sensing controller determines that the content is discharged by the passing operation part when an amount of change in the quantity of light received by the light receiver is equal to and greater than a predetermined amount of change and then returns to a state before changing to the predetermined amount of change or larger.

11. The passing device of claim 1, wherein the rotatable structure of the passing movement part has a hollow cylinder shape in which a rotation axis is disposed so that the rotatable structure of the passing movement part is rotatable around the rotatable axis.

12. The passing device of claim 1, wherein the sensing controller determines that the content is discharged when an amount of change in the quantity of light is equal to or greater than a predetermined amount of change in a state in which the slope of the housing sensed by the tilt sensor is within the predetermined slope range and determines that the content is not discharged when the amount of change in the quantity of light is equal to or greater than the predetermined amount of change in a state in which the slope of the housing sensed by the tilt sensor is outside the predetermined slope.

13. The passing device of claim 3, wherein the light emitter is installed at one side of the passing movement part, and the light receiver is installed at another side of the passing movement part.

14. The passing device of claim 1, wherein the passing operation part comprises a fixing member configured to form an opening to pass content and a movement guide part having an inclined surface to guide introduction of the content, and
wherein the light emitter is installed in a support part protruding from the movement guide part and a through hole is formed in the passing operation part so that light emitted from the light emitter can be emitted to the passing movement part.

* * * * *